US005986568A

United States Patent [19]

Suzuki et al.

[11] Patent Number: 5,986,568

[45] Date of Patent: *Nov. 16, 1999

[54] INFORMATION TRANSFER METHOD, INFORMATION TRANSFER SYSTEM, INFORMATION INPUTTING METHOD, INFORMATION INPUT DEVICE, AND SYSTEM FOR SUPPORTING VARIOUS OPERATIONS

[75] Inventors: Takuji Suzuki, Kawasaki; Masafumi Kondo, Sagamihara, both of Japan

[73] Assignee: Kabushiki Kaisha Toshiba, Kawasaki, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/722,983

[22] Filed: Sep. 30, 1996

[30] Foreign Application Priority Data

| | | | |
|---|---|---|---|
| Sep. 29, 1995 | [JP] | Japan | 7-253285 |
| Jul. 19, 1996 | [JP] | Japan | 8-191051 |

[51] Int. Cl.$^6$ .................................................. G06F 17/30

[52] U.S. Cl. ............................ 340/825.52; 340/825.19; 455/517; 707/104; 707/10; 370/392

[58] Field of Search ...................... 340/825.52, 825.19, 340/825.15, 825.44; 128/903, 904; 455/507, 557, 517; 345/333, 326, 168; 395/893, 894; 707/104, 1, 10; 370/392, 395

[56] References Cited

U.S. PATENT DOCUMENTS

| | | | |
|---|---|---|---|
| 5,146,439 | 9/1992 | Jackmann et al. | 369/29 X |
| 5,522,089 | 5/1996 | Kikinis et al. | 395/893 |
| 5,561,446 | 10/1996 | Montlick | 455/517 X |
| 5,564,070 | 10/1996 | Want et al. | 455/507 |
| 5,566,291 | 10/1996 | Boulton et al. | 345/326 |
| 5,584,025 | 12/1996 | Keithley et al. | 707/104 |
| 5,625,880 | 4/1997 | Goldburg et al. | 455/507 X |

OTHER PUBLICATIONS

Computer Graphics Animations of Talking Faces Based on Stochastic Models, N.M. Brooks et al., ISSIPNN '94, 1994 International Symposium on Speech, Image Processig and Neural Networks Proceedings, Apr. 1994, pp. 73–76.

Welsh W.J. et al., "Facial Feature Image Coding Using Principal Components", Electronics Letters, vol. 28, No. 22, Oct. 22, 1992, pp. 2066–2067.

*Primary Examiner*—Brian Zimmerman
*Assistant Examiner*—William H. Wilson, Jr.
*Attorney, Agent, or Firm*—Oblon, Spivak, McClelland, Maier & Neustadt, P.C.

[57] ABSTRACT

Information inputted from an information terminal and destination information of a third person added to specific information which should be transferred to the third person and which is included in the information inputted are transferred to an information processing unit through a communication unit and are accumulated in a data base of the information processing unit, the specific information is extracted from the information accumulated in the data base on the basis of the destination information, thereby preparing a file and the specific information accumulated in the file is transmitted to the third person.

8 Claims, 50 Drawing Sheets

PATIENT INFORMATION WORK SHEET

| MAIN MENU | SUBMENU | DATA STRUCTURE |
|---|---|---|
| BASIC INFORMATION | PATIENT ID | NUMERIC VALUE |
| | NAME | TEXT |
| | THE DISTINCTION OF SEX | TEXT OR NUMERIC VALUE (ID) |
| | ADDRESS | TEXT |
| | TELEPHONE NUMBER | NUMERIC VALUE |
| | THE DATE OF BIRTH | NUMERIC VALUE |
| | MAIN INJURY DISEASE NAMES | NUMERIC VALUE (SELECTED FROM INJURY DISEASE DATA BASE) |
| | DISEASE SITUATION, MEDICAL TREATMENT STATE | NUMERIC VALUE (DEGREE SELECTION)+TEXT |
| ASSESSMENT | PREVIOUS ILLNESS | NUMERIC VALUE (SELECTED FROM INJURY DISEASE DATA BASE) |
| | LIFE HISTORY | TEXT |
| | FAMILY CONSTRUCTION AND SITUATION | FAMILY DATA BASE (NAME, FAMILY RELATION, ETC.) |
| | MAIN INTERPOSING PROTECTOR | TEXT (NAME) |
| | LIVING ENVIRONMENT | NUMERIC VALUE (CLASSIFICATION SELECTION) |

FIG. 5A

| | | |
|---|---|---|
| | REQUEST OBJECT | TEXT |
| | ADL SITUATION | NUMERIC VALUE (DEGREE SELECTION IN EACH ITEM) |
| | CLASSIFICATION OF INSURANCE | NUMERIC VALUE (CLASSIFICATION SELECTION, NUMBER) |
| INSTRUCTIONS OF DOCTOR | DISEASE SITUATION, MEDICAL TREATMENT STATE | NUMERIC VALUE (GRADE SELECTION)+TEXT |
| | GIVEN MEDICINE | NUMERIC VALUE (SELECTED FROM MEDICINE DATA BASE) |
| | DOMENTIA SITUATION | NUMERIC VALUE (GRADE SELECTION) |
| | BEDRIDDEN DEGREE | NUMERIC VALUE (GRADE SELECTION) |
| | MOUNTING MEDICAL INSTRUMENT, ETC. | NUMERIC VALUE (CLASSIFICATION SELECTION) |

FIG. 5B

| | | |
|---|---|---|
| | ATTENTION MATTERS ON MEDICAL CARE LIFE GUIDANCE | TEXT |
| | TREATMENT OF BEDSORE, ETC. | TEXT |
| | OPERATING SUPPORT AND MANAGEMENT OF MOUNTING MEDICAL INSTRUMENT, ETC. | TEXT |
| | METHOD FOR COPING WITH ABSENT TIME | NUMERIC VALUE (CLASSIFICATION SELECTION) |
| | SPECIAL MENTION MATTERS | TEXT |
| SUMMARY | VISITING DATE | NUMERIC VALUE |
| | MONTHLY DISEASE SITUATION | TEXT |
| | MONTHLY NURSING CONTENTS | NUMERIC VALUE (CLASSIFICATION SELECTION) OR TEXT |
| | SITUATION OF INTERPOSING PROTECTOR | TEXT |

FIG. 5C

| | | |
|---|---|---|
| COMMUNICATION DESTINATION | INFORMATION OF FAMILY DOCTOR | FAMILY DOCTOR DATABASE (NAME, ADDRESS, ETC.) |
| | COMMUNICATION METHOD AT EMERGENCY TIME | NUMERIC VALUE (CLASSIFICATION SELECTION) |
| | COMMUNICATION DESTINATIONS OF RELATED ORGANS | DATABASE OF RELATED ORGANS |
| SYNTHESIS | GENERAL OPINION | TEXT |
| | INFORMATION WHICH SOULD BE TRANSFERRED | TEXT |

FIG. 5D

VISITING RECORD WORK SHEET

| MAIN MENU | SUBMENU | DATA STRUCTURE |
|---|---|---|
| HEADER | PATIENT ID | NUMERIC VALUE |
| | PATIENT NAME | TEXT |
| | VISITOR NAME | TEXT OR ID (NUMERIC VALUE) |
| | VISITING DATE | NUMERIC VALUE |
| | VISITING TIME | NUMERIC VALUE |
| VITAL SIGNS | BODY TEMPERATURE | NUMERIC VALUE |
| | PULSATION | NUMERIC VALUE |
| | BREATH | NUMERIC VALUE |
| | BLOOD PRESSURE | NUMERIC VALUE |
| | DISEASE SITUATION | TEXT (UNFIXED TYPE) |
| | STATE OF BEDSORE | NUMERIC VALUE (SELECT PART AND DEGREE FROM GRAPHIC) |
| MENTAL STATE | DEGREE OF STABILITY | NUMERIC VALUE (SELECT PART AND DEGREE FROM GRAPHIC) |
| | TASTE | TEXT (UNFIXED TYPE) |
| | TROUBLES, ETC. | TEXT (UNFIXED TYPE) |
| FAMILY STATE | STATE OF INTERPOSING PROTECTOR | TEXT (UNFIXED TYPE) |
| | PHYSICAL FATIGUE DEGREE OF INTERPOSING PROTECTOR | NUMERIC VALUE (SELECT PART AND DEGREE FROM GRAPHIC) |
| | MENTAL FATIGUE DEGREE OF INTERPOSING PROTECTOR | NUMERIC VALUE (SELECT PART AND DEGREE FROM GRAPHIC) |

FIG. 6A

| | OTHER FAMILY SITUATIONS | TEXT (UNFIXED TYPE) |
|---|---|---|
| CONTENTS OF TREATMENT | CLEANING-WIPING | NUMERIC VALUE (EXISTENCE OR NONEXISTENCE OF TREATMENT, EXISTENCE OR NONEXISTENCE OF GUIDANCE) |
| | HAIR WASHING | NUMERIC VALUE (EXISTENCE OR NONEXISTENCE OF TREATMENT, EXISTENCE OR NONEXISTENCE OF GUIDANCE) |
| | SHEET EXCHANGE | NUMERIC VALUE (EXISTENCE OR NONEXISTENCE OF TREATMENT, EXISTENCE OR NONEXISTENCE OF GUIDANCE) |
| | INTERPOSING ASSISTANCE OF MEAL | NUMERIC VALUE (EXISTENCE OR NONEXISTENCE OF TREATMENT, EXISTENCE OR NONEXISTENCE OF GUIDANCE) |
| | INTERPOSING ASSISTANCE OF EXCRETION | NUMERIC VALUE (EXISTENCE OR NONEXISTENCE OF TREATMENT, EXISTENCE OR NONEXISTENCE OF GUIDANCE) |

FIG. 6B

| | | |
|---|---|---|
| | BODY POSITION CONVERSION | NUMERIC VALUE (EXISTENCE OR NONEXISTENCE OF TREATMENT, EXISTENCE OR NONEXISTENCE OF GUIDANCE) |
| | TREATMENT OF BEDSORE | NUMERIC VALUE (PART SELECTION, EXISTENCE OR NONXISTENCE OF TREATMENT, EXISTENCE OR NONEXISTENCE OF GUIDANCE) |
| | REHABILITATION | NUMERIC VALUE (CLASSIFICATION, EXISTENCE OR NONEXISTENCE OF TREATMENT, EXISTENCE OR NONEXISTENCE OF GUIDANCE) |
| | TAKING MEDICINE | NUMERIC VALUE (CLASSIFICATION SELECTION, EXISTENCE OR NONEXISTENCE OF GUIDANCE) |
| | INSPECTION ASSISTANCE | NUMERIC VALUE (CLASSIFICATION SELECTION, EXISTENCE OR NONEXISTENCE OF GUIDANCE) |
| | ENVIRONMENTAL MAINTENANCE | TEXT (UNFIXED TYPE) |

FIG. 6C

| | | |
|---|---|---|
| | INTERPOSING GUIDANCE OF FAMILY | TEXT (UNFIXED TYPE, CONTENTS, ETC.) |
| | MANAGEMENT OF CATHETER | NUMERIC VALUE (PART SELECTION, EXISTENCE OR NONEXISTENCE OF TREATMENT, EXISTENCE OR NONEXISTENCE OF GUIDANCE) |
| | BLADDER WASHING | NUMERIC VALUE (EXISTENCE OR NONEXISTENCE OF TREATMENT, EXISTENCE OR NONEXISTENCE OF GUIDANCE) |
| | MANAGEMENT RELATIVE TO AT-HOME OXYGEN MEDICAL TREATMET | NUMERIC VALUE (EXISTENCE OR NONEXISTENCE OF TREATMENT, EXISTENCE OR NONEXISTENCE OF GUIDANCE) |
| | OTHER DIAGNOSIS AND TREATMENT ASSISTANCES | TEXT (UNFIXED TYPE) |
| | OTHERS | TEXT (UNFIXED TYPE) |
| SYNTHESIS | GENERAL OPINION | TEXT (UNFIXED TYPE) |
| | INFORMATION WHICH SHOULD BE TRANSFERRED | TEXT (UNFIXED TYPE) |

F I G. 6D

| COMMENT FILE | | |
|---|---|---|
| MAIN MENU | ITEM NAME | DATA STRUCTURE |
| HEADER PORTION | SERIAL NUMBER | NUMERIC VALUE |
| | PATIENT ID | NUMERIC VALUE |
| | PATIENT NAME | TEXT (AUTOMATIC INPUT FROM PATIENT ID) |
| | NAME OF INPUT PERSON | TEXT (AUTOMATIC INPUT FROM PERSON ID IN CHARGE) |
| | INPUT DATE | NUMERIC VALUE |
| | INPUT TIME | NUMERIC VALUE |
| | CORRESPONDING ITEM ADDRESS | NUMERIC VALUE (DATA SHOWING LINK POSITION, EX. (01. 01. 02)) |
| | CLASSIFICATION OF DATA | NUMERIC VALUE (SELECTION:BIT MAP/IMAGE/VOICE/TEXT) |
| | DATA SIZE | (THE NUMBERS OF LONGITUDINAL AND TRANSVERSAL BITS, EX. (160, 240)) |
| DATA PORTION (BITMAP/IMAGE/VOICE/TEXT) | | |

FIG. 7

| FILE WHICH SHOULD BE TRANSFERRED | | |
|---|---|---|
| MAIN MENU | ITEM NAME | DATA STRUCTURE |
| HEADER PORTION | SERIAL NUMBER | NUMERIC VALUE |
| | PATIENT ID | NUMERIC VALUE |
| | PATIENT NAME | TEXT (AUTOMATIC INPUT FROM PATIENT ID) |
| | NAME OF INPUT PERSON | TEXT (AUTOMATIC INPUT FROM PERSON ID IN CHARGE) |
| | INPUT DATE | NUMERIC VALUE |
| | INPUT TIME | NUMERIC VALUE |
| | CORRESPONDING ITEM ADDRESS | NUMERIC VALUE (DATA SHOWING LINK POSITION, EX. (01. 01. 02)) |
| | DESTINATION ID | NUMERIC VALUE (DESTINATION SELECTION:PLURAL) |
| | CLASSIFICATION OF DATA | NUMERIC VALUE (SELECTION:BIT MAP/IMAGE/VOICE/TEXT) |
| | DATA SIZE | (THE NUMBERS OF LONGITUDINAL AND TRANSVERSAL BITS, EX. (160, 240)) |
| DATA PORTION (BITMAP/IMAGE/VOICE/TEXT) | | |

FIG. 8

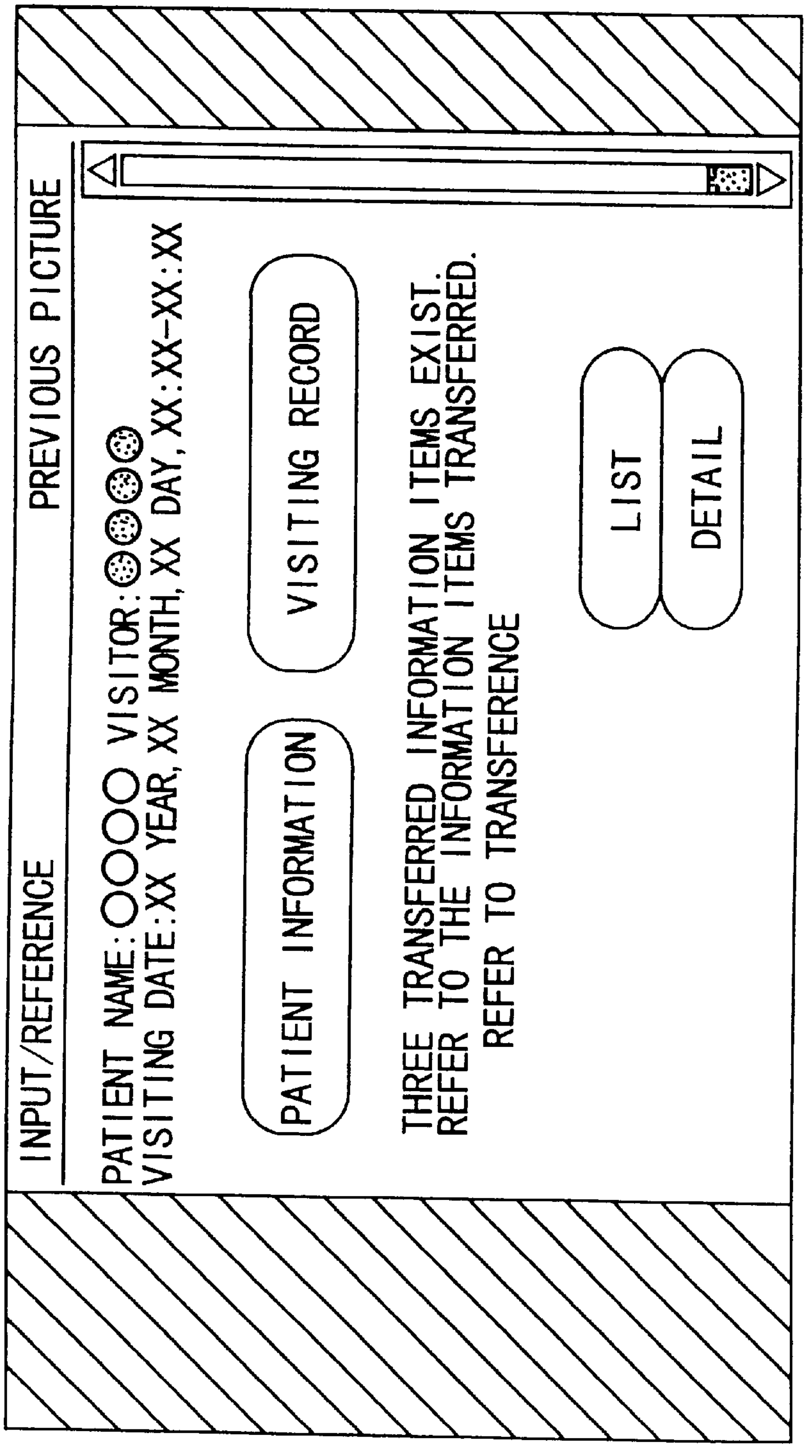
F I G. 1 2

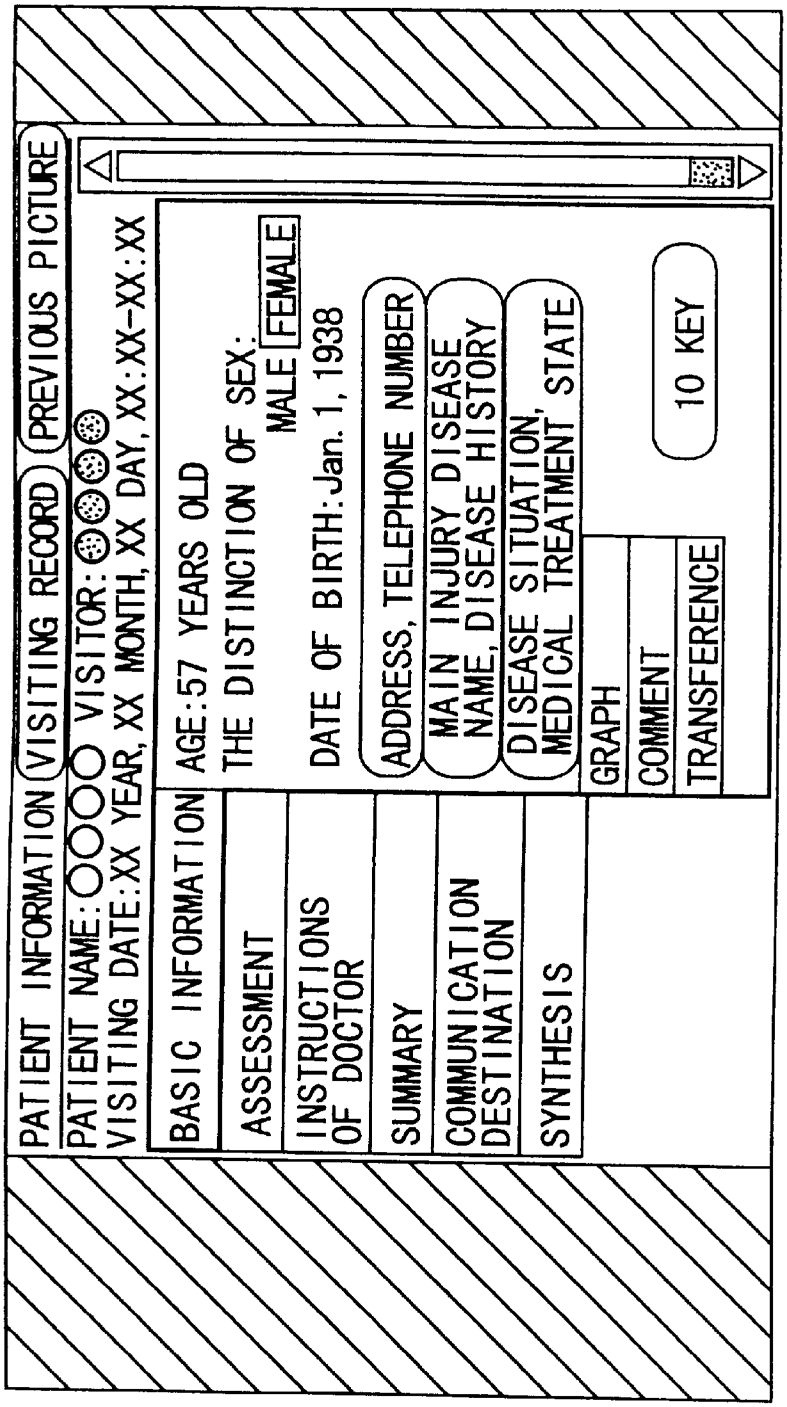

F I G. 13

PATIENT INFORMATION / VISITING RECORD / PREVIOUS PICTURE
PATIENT NAME: ○○○○ VISITOR: ⦿⦿⦿⦿
VISITING DATE: XX YEAR, XX MONTH, XX DAY, XX:XX-XX:XX

BASIC INFORMATION | AGE:57 YEARS OLD
THE DISTINCTION OF SEX: MALE / FEMALE
DATE OF BIRTH: Jan. 1, 1938
ADDRESS, TELEPHONE NUMBER
MAIN INJURY DISEASE NAME, DISEASE HISTORY
DISEASE SITUATION, MEDICAL TREATMENT STATE

ASSESSMENT
INSTRUCTIONS OF DOCTOR
SUMMARY
COMMUNICATION DESTINATION
SYNTHESIS

GRAPH
COMMENT
TRANSFERENCE

10 KEY

| VISITING RECORD | PATIENT INFORMATION | PREVIOUS PICTURE |

PATIENT NAME: ○○○○ VISITOR: ⊙⊙⊙⊙
VISITING DATE: XX YEAR, XX MONTH, XX DAY, XX:XX-XX:XX

| VITAL SIGNS | BODY TEMPERATURE: 36.5°C<br>PULSATION: 20/30 SECONDS<br>BREATH: 10/30 SECONDS<br>BLOOD PRESSURE:<br>(HIGHEST) 130 (LOWEST) 70 |
| --- | --- |
| MENTAL STATE | |
| FAMILY STATE | |
| CONTENTS OF TREATMENT | |
| SYNTHESIS | |

| GRAPH | COMMENT | TRANS-FERENCE |

| 7 | 8 | 9 | BACK-SPACE |
| 4 | 5 | 6 | |
| 1 | 2 | 3 | INPUT |
| 0 | 000 | . | |

TRANSFER: VISITING RECORD/
CONTENTS OF TREATMENT/
TREATMENT OF BEDSORE
PREVIOUS PICTURE
PATIENT INFORMATION
PATIENT NAME: ○○○○ VISITOR: ⊙⊙⊙⊙
VISITING DATE: XX YEAR, XX MONTH, XX DAY, XX:XX-XX:XX
INPUT PERSON: △△△△  PAGE: 1
TAKE-IN IMAGE  DESIGNATE AREA
DESTINATION: ALL | PERSON IN CHARGE | PERSON
FAMILY DOCTOR
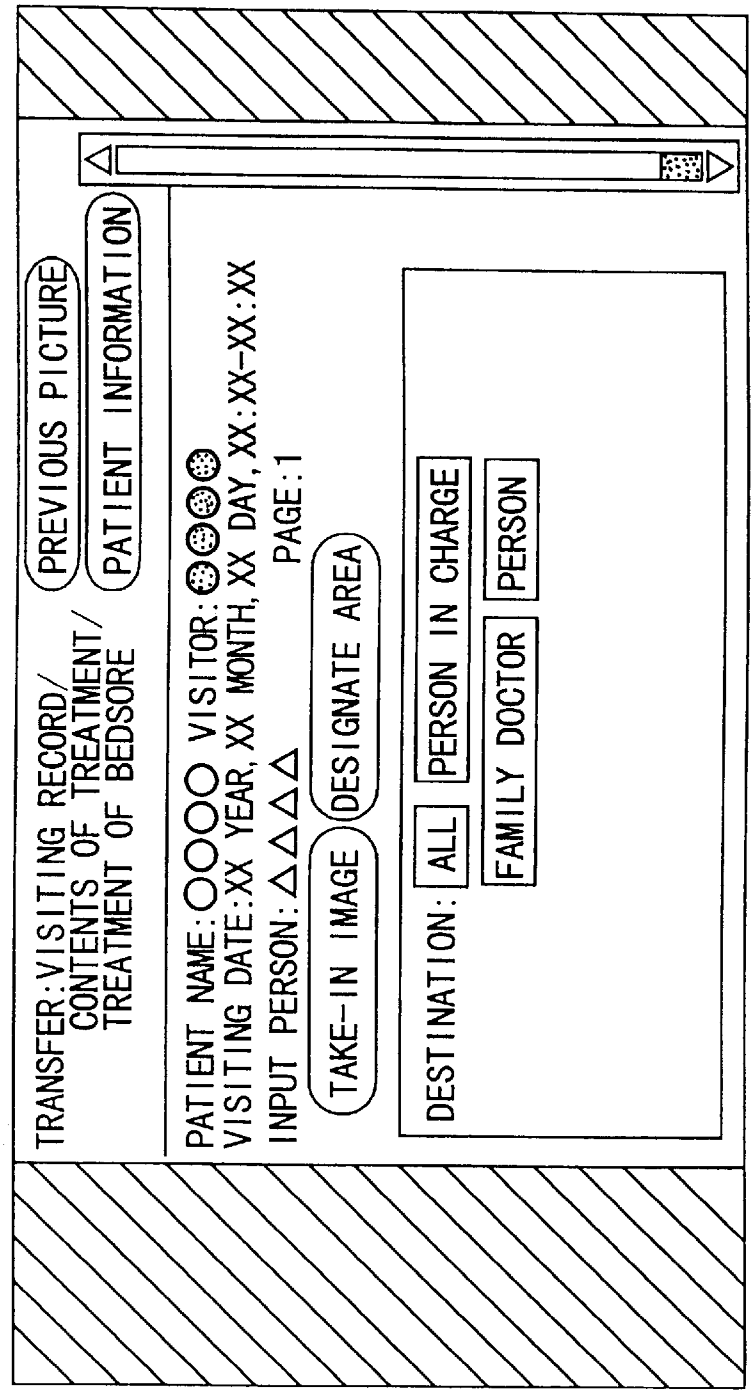
F I G. 1 6

COMMENT: VISITING RECORD/ CONTENTS OF TREATMENT/ TREATMENT OF BEDSORE

PREVIOUS PICTURE | PATIENT INFORMATION

PATIENT NAME: ○○○○ VISITOR: ◉◉◉◉
VISITING DATE: XX YEAR, XX MONTH, XX DAY, XX:XX-XX:XX
INPUT PERSON: △△△△    PAGE: 1

TAKE-IN IMAGE | DESIGNATE AREA

PRESENT PICTURE
IMAGE FILE
EXTERNAL INPUT

LIST OF FILES WHICH SHOULD BE TRANSFERRED (PREVIOUS PICTURE)
(PATIENT INFORMATION)

PATIENT NAME: ○○○○
VISITING DATE  VISITOR  ATTRIBUTE  CONTENTS OF TREATMENT  VITAL SIGNS
XX/XX XX:XX-XX:XX ●●●● ●●●● ●●●●
XX/XX XX:XX-XX:XX ●●●● ●●●●
. . . . . . . . . . . . . . . . . .

VISITING RECORD/
CONTENTS OF TREATMENT/
BATH

PREVIOUS PICTURE

PATIENT INFORMATION

PATIENT NAME: ○○○○  VISITOR: ◉◉◉◉
4/1XX:XX-XX:XX~4/30XX:XX-XX:XX

| 1 | 2 | 3 | 4 | 5 | 6 | 7 |
| 8 | 9 | 10 | 11 | 12 | 13 | 14 |
| 15 | 16 | 17 | 18 | 19 | 20 | 21 |
| 22 | 23 | 24 | 25 | 26 | 27 | 28 |
| 29 | 30 | | | | | |

☐ EXECUTION DAY
▨ COMMENT
● TRANSFER

| PATIENT NAME: ○○□□ | | |
|---|---|---|
| #1 | THERE IS A FEAR THAT MYOCARDIAL INFARCTION OCCURS AND RESULTS IN CARDIAC INSUFFICIENCY | GENERATING DAY 1996/01/22<br>SOLVING DAY 1996/01/29 |
| #2 | BLADDER DETAINING CATHETER IS EXPECTED | GENERATING DAY 1996/01/22<br>SOLVING DAY |
| #3 | CATHARTIC CONTROL IS DIFFICULT | GENERATING DAY 1996/01/22<br>SOLVING DAY |
| #4 | INTERPOSING PROTECTOR IS WIFE AT ADVANCED AGE | GENERATING DAY 1996/01/22<br>SOLVING DAY |
| #5 | IT IS NECESSARY TO INCREASE ADL WHILE LOOKING DISEASE | GENERATING DAY 1996/01/22<br>SOLVING DAY |
| #6 | | GENERATING DAY<br>SOLVING DAY |

ADDITION   SOLUTION

OTHERS

COMMENT   REGISTER   CANCEL   END

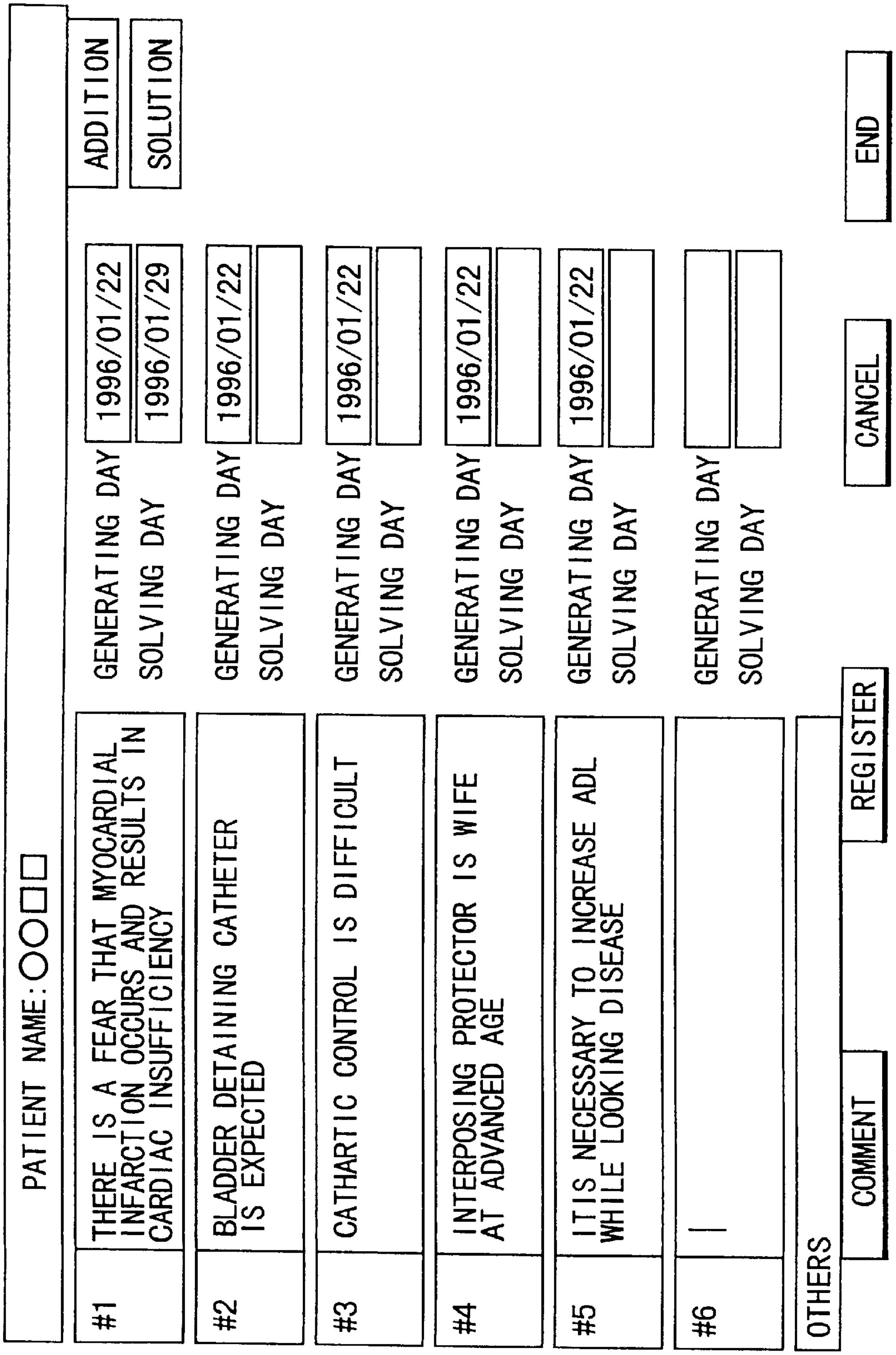

F I G. 2 2

| DESTINATION DESIGNATION | CODE |
|---|---|
| ALL | 1 |
| ALL PERSONS IN CHARGE | 2 |
| NEXT PERSON IN CHARGE | 3 |
| FAMILY DOCTOR | 4 |
| ⋮ | ⋮ |

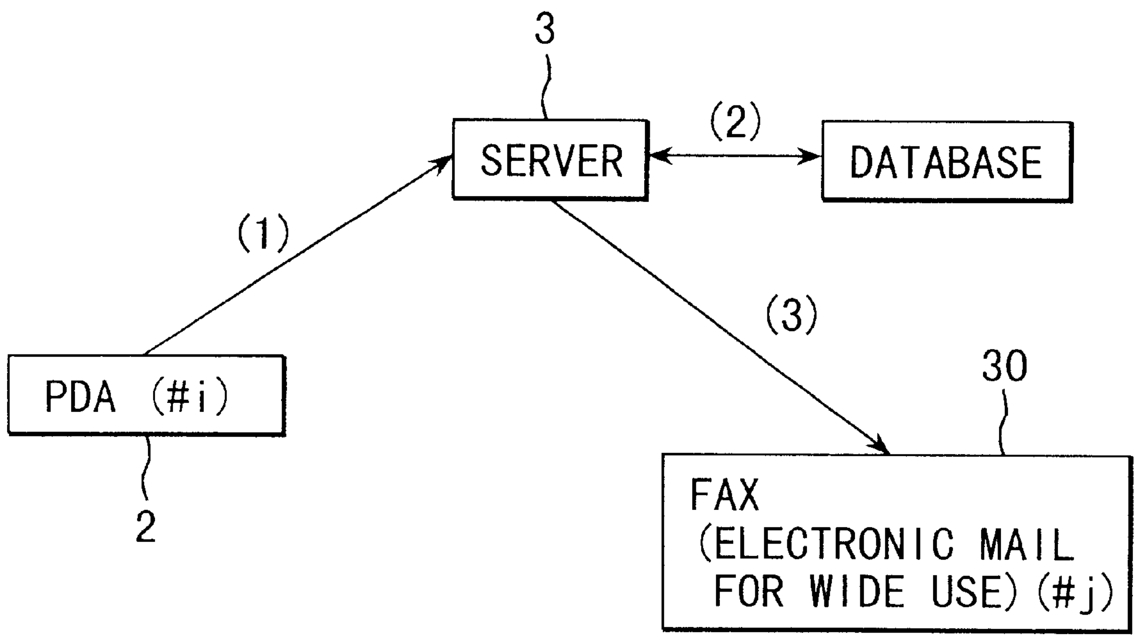
F I G. 27

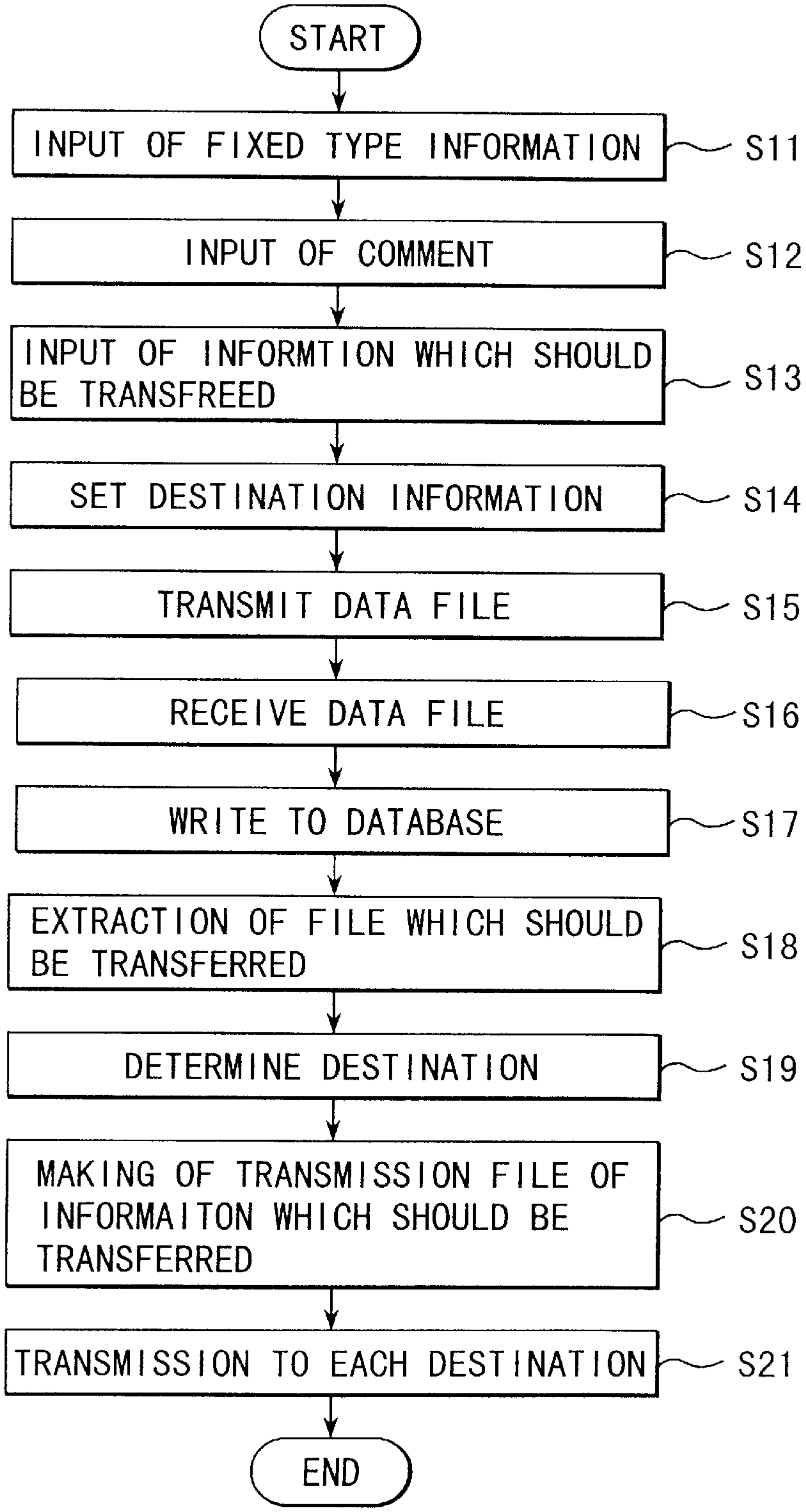
F I G. 28

| USER | PAGER | FAX | ELECTRONIC MAIL FOR WIDE USE |
|---|---|---|---|
| : | | | |
| h | NUMBER Ph | – | – |
| i | NUMBER Pi | – | – |
| j | NUMBER Pj | – | – |
| k | – | NUMBER Fk | – |
| l | NUMBER Pl | – | ADDRESS l |
| m | NUMBER Pm | NUMBER Fm | ADDRESS m |
| : | | | |

FIG. 32

| USER | ... | FAX | ... |
|---|---|---|---|
| :<br>y<br>: | ... | (:～:, NUMBER Fy1),<br>(:～:, NUMBER Fy2) | ... |

FIG. 33

| COMMENT FILE | | |
|---|---|---|
| MAIN MENU | ITEM NAME | DATA STRUCTURE |
| HEADER PORTION | SERIAL NUMBER | NUMERIC VALUE |
| | PATIENT ID | NUMERIC VALUE |
| | PATIENT NAME | TEXT (AUTOMATIC INPUT FROM PATIENT ID) |
| | NAME OF INPUT PERSON | TEXT (AUTOMATIC INPUT FROM PERSON ID IN CHARGE) |
| | INPUT DATE | NUMERIC VALUE |
| | INPUT TIME | NUMERIC VALUE |
| | CORRESPONDING ITEM ADDRESS | NUMERIC VALUE (DATA SHOWING LINK POSITION, EX. (01.01.02)) |
| | DESTINATION ID | NUMERIC VALUE OR NULL |
| | CLASSIFICATION OF DATA | NUMERIC VALUE (SELECTION:BIT MAP/IMAGE/VOICE/TEXT) |
| | DATA SIZE | (THE NUMBERS OF LONGITUDINAL AND TRANSVERSAL BITS, EX. (160, 240)) |
| DATA PORTION (BITMAP/IMAGE/VOICE/TEXT) | | |

FIG. 34

| VISITING RECORD | PATIENT INFORMATION | PREVIOUS PICTURE |

PATIENT NAME: ○○○○ VISITOR: ◉◉◉◉
VISITING DATE: XX YEAR, XX MONTH, XX DAY, XX:XX–XX:XX

| VITAL SIGNS | BODY TEMPERATURE: 36.5°C<br>PULSATION: 20/30 SECONDS<br>BREATH: 10/30 SECONDS<br>BLOOD PRESSURE:<br>(HIGHEST) 130 (LOWEST) 70 | 7 8 9 | BACK-SPACE |
| MENTAL STATE | | 4 5 6 | |
| FAMILY STATE | | 1 2 3 | INPUT |
| CONTENTS OF TREATMENT | | 0 000 . | |
| SYNTHESIS | GRAPH / COMMENT | | |

| COMMENT FILE | | |
|---|---|---|
| MAIN MENU | ITEM NAME | DATA STRUCTURE |
| HEADER PORTION | SERIAL NUMBER | NUMERIC VALUE |
| | PATIENT ID | NUMERIC VALUE |
| | PATIENT NAME | TEXT (AUTOMATIC INPUT FROM PATIENT ID) |
| | NAME OF INPUT PERSON | TEXT (AUTOMATIC INPUT FROM PERSON ID IN CHARGE) |
| | INPUT DATE | NUMERIC VALUE |
| | INPUT TIME | NUMERIC VALUE |
| | CORRESPONDING ITEM ADDRESS | NUMERIC VALUE (DATA SHOWING LINK POSITION, EX. (01. 01. 02)) |
| | FLAG FOR SETTING TRANSFERENCE | NUMERIC VALUE OR NULL |
| | CLASSIFICATION OF DATA | NUMERIC VALUE (SELECTION:BIT MAP/IMAGE/VOICE/TEXT) |
| | DATA SIZE | (THE NUMBERS OF LONGITUDINAL AND TRANSVERSAL BITS, EX. (160, 240)) |
| DATA PORTION (BITMAP/IMAGE/VOICE/TEXT) | | |

FIG. 41

INFORMATION TRANSFER METHOD, INFORMATION TRANSFER SYSTEM, INFORMATION INPUTTING METHOD, INFORMATION INPUT DEVICE, AND SYSTEM FOR SUPPORTING VARIOUS OPERATIONS

BACKGROUND OF THE INVENTION

1. Field of the Invention

The present invention relates to a system for supporting a variety of operations, such as a home-based medical treatment such as house call, nursing, home-help, rehabilitation, and home-based cares, maintenance operations such as plants, and guarding operations.

2. Description of the Related Art

Recently, portable information communication terminals (Personal Digital Assistants; PDA) have been successively developed by manufacturers. The portable information communication terminals are compact and light enough to carry daily and can manage personal information and communicate information the user obtains at any place he is visiting, through a telephone line or the like. On the other hand, portable telephone have entered into common use in recent years, and simple portable telephones (Personal Handy-phone System; PHS) have just been developed. Generalization of radio telephones and data communication are thereby further accelerated. There is the trend that a function similar to that is imparted to the PHS, enabling the PHS to serve as a radio data communication terminal.

Among these communication terminals, a terminal developed recently which can treat various types of information such as image, voice and the like, as well as conventional character information. A color image can be recorded in full color with high definition, composed of about 410,000 pixels, by a compact digital still camera. The image information thus obtained can be inputted to said terminal. An illustration, memorandum and so forth can be written onto the image in a bit map format. The image can be linked to a memorandum or the like to which voice information is simultaneously written.

A rapid increase in the number of house patients is expected as the percentage of the elderly increases in the near future. In this case, it is anticipated that problems of an increase in burden of home-help and insufficiency of man power become serious. The Ministry of Health and Welfare of Japan made a “gold plan” and a “new gold plan” to enlarge facilities such as health facilities for the old, and to increase the number of home helpers. According to these plans, institutionalized visiting nursing stations function as bases of the home-based medical treatment. Enlargements of man power and supporting facilities such as 10,000 home helper stations are further expected.

The physical burden of a person in charge of the home-based care is heavy as long as the care is performed such that the person in charge visits the patient’s house. In particular, it is necessary that the home-based care is at least equal to the care which can be given to the patient who is in the hospital. Accordingly, a support in an all-day system is indispensable, but there is a physical limit in continuous attendance of one person in charge of the patient. Accordingly, rotational care and a rotation system of plural persons in charge are indispensable. At this time, if no information of the state of the patient, contents of treatment and so forth obtainable from visiting is shared by the persons in charge, each person in charge cannot obtain information of the patient when they are off duty. As a result, continuous and uniform care cannot sufficiently be given to the patient. In the case of nursing in a hospital, information can be shared attributable to periodical conference, cyclic transference of information and so forth. However, since the home-based care is performed such that a person in charge visits the patient’s home, conference cannot frequently be held, thus resulting in a problem to arise in that information cannot easily be shared. What is worse, in the case of the home-based care in which various persons such as a visiting nurse, a home helper, a doctor, etc. alternately visit the patient, information cannot easily be shared among the foregoing persons in charge.

Such problems are not limited to home-based care, but are common to a system for supporting various operations for mobile workers in which a team of persons in charge is organized and the persons in charge alternately go to a destination as in a maintenance operation of a plant or the like, a maintenance service operation, a guarding operation of a building or the like, business or the like, and persons other than the person in charge take charge of such operations in an emergency situation.

SUMMARY OF THE INVENTION

An object of the present invention is to provide an information input terminal device and a system for supporting various operations in which a mobile worker can simply input predetermined information at any time in an operation at a destination, and can simply refer to previous data relative to the same operation and messages of comments/information which should be transferred which have been inputted by another mobile worker.

Another object of the present invention is to provide an information transfer method, an information transfer system, an information inputting method and an information input device in which a message showing information which should be transferred or its existence can be transmitted to a required partner in a system for transferring and storing information generated in the operation of a mobile worker at a destination to a server device from a portable terminal device.

According to a first aspect of the present invention, an information transmitting method comprises the steps of: inputting, by an information terminal unit, information; arbitrarily designating, by the information terminal unit, specific information among the inputted information; appending, by the information terminal unit, destination address information to the designated specific information; transmitting, by the information terminal unit and to information processing unit through communication means, the information inputted by the information terminal and including the specific information with the destination address information appended; extracting, by the information processing unit, the specific information; and transmitting, by the information processing unit, the extracted specific information to a person according to the appended destination information.

According to a second aspect of the present invention, an information transmitting method comprises the steps of: inputting, by an information terminal unit, information; arbitrarily designating, by the information terminal unit, specific information among the inputted information; appending, by the information terminal unit, destination address information to the designated specific information; transmitting, to an information processing unit having data base through communication means, the information inputted by the information terminal unit and including the specific information with the destination address information appended; storing, by the information processing unit, the transmitted information in the data base; and transmitting, by the information processing unit, a message to a person according to the appended destination address information in order to inform the person of an existence of the specific information.

According to a third aspect of the present invention, an information transmitting system comprising: an information terminal unit connected to an information processing unit having a data base through communication means, for inputting information; means for arbitrarily designating specific information among the entire information inputted by the information terminal unit; means for appending destination address information to the specific information for transmitting the specific information to a person; transmission instructing means for instructing transmission of the specific information to the information processing unit; information transmitting means for, in response to the transmission instruction, transmitting the entire information inputted by the information terminal unit, the entire information including the specific information with the destination address information appended, thereby the information processing unit extracting the specific information from the transmitted entire information and transmitting the extracted specific information to the person according to the appended destination address information.

According to a fourth aspect of the present invention, information processing unit coupled to an information terminal unit through communication means comprises: a data base; means for storing, in the data base, information stream transmitted through the communication means from the information terminal unit, the information stream including specific information with destination address information appended, the specific information is to be transmitted to a person; means for extracting the specific information from the information stream stored in the data base and for preparing a file including the specific information to be transmitted to the person; and means for transmitting the specific information included in the file to the person in accordance with the appended destination address information.

According to a fifth aspect of the present invention, information processing unit coupled to an information terminal unit through communication means comprises: a data base; means for storing, in the data base, information stream transmitted through the communication means from the information terminal unit, the information stream including specific information with destination address information appended, the specific information is to be transmitted to a person; and means for transmitting a message indicating an existence of the specific information to the person in accordance with the appended destination address information.

According to a sixth aspect of the present invention, an information inputting method for inputting an information stream to be stored in a data base of an information processing unit coupled to communication means, the method comprises the steps of: arbitrarily designating a specific information in the information stream which is to be transmitted to the data base; instructing to append destination address information to the designated specific information, the destination address information being different from that of the data base; and instructing to transmit the information stream including the specific information with the destination address information appended to the communication means.

According to a seventh aspect of the present invention, an information input unit for inputting an information stream to be stored in a data base of an information processing unit coupled to the information input unit through communication means, the information input unit comprises: means for arbitrarily designating a specific information in the information stream which is to be transmitted to the information processing unit; means for appending destination address information to the designated specific information, the destination address information being different from that of the information processing unit; and means for transmitting the information stream including the specific information with the destination address appended to the information processing unit through the communication means.

According to an eighth aspect of the present invention, an information input device comprises: input means for inputting information; reference means for referring to the information; and memory means for storing fixed type information inputted to plural items constituting a data base, arbitrary information related to the items, and information for relating the arbitrary information and the items to each other, at least one portion of the arbitrary information being related to an item except for the items related to the arbitrary information, and can be stored into the memory means.

According to a ninth aspect of the present invention, a system for supporting various operations, comprises: an information terminal, having input means for inputting information; reference means for referring to the information; and memory means for storing fixed type information inputted to plural items constituting a data base, arbitrary information related to the items, and information for relating the arbitrary information and the items to each other; at least one information processor for managing information constituting the data base; and communication means for connecting the information terminal and the information processor to each other.

In accordance with the present invention, a menu of the data base is subdivided and the fixed type information is simply inputted to each item. The arbitrary information such as comments, information which should be transferred and which are related to each item is linked to each item, and then inputted. Accordingly, information unable to be represented by a fixed type input can be recorded and communicated (transferred) along an operating flow in a manner linked to the item of the data base without any burden. Further, such information can be rapidly referenced for each item.

For example, when a home-based care operation is performed by rotating plural persons in charge, a person in charge takes a treatment at a visiting time while the person in charge refers to previous information on the patient accumulated by another person in charge. The person in charge inputs simple information, etc. related to this treatment at any time. This information is transferred to a host personal computer and is collectively managed. The plural persons in charge in a rotation team refer to this information at any time so that the information can be shared between the persons in charge.

Further, in accordance with the present invention, it is possible to provide an information terminal in which this information terminal is carried in execution of a predetermined operation of a person in charge (home-based care, various maintenance operations, guard, etc.), and various fixed type information (a patient state and treatment contents, maintenance matters, etc.) can be simply inputted at any time, and arbitrary information (comments and data which should be transferred with respect to the patient, etc.) related to these fixed type information items can be suitably inputted, and past arbitrary information inputted by another person in charge can be simply referenced.

Further, it is possible to provide a system for supporting various operations in which the various operations can be efficiently performed by using such an information terminal.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 5A through 5D illustrate a diagram typically showing a work sheet structure of patient information in the patient data base.

FIGS. 6A through 6D illustrate a diagram typically showing a work sheet structure of a visiting record in the patient data base.

FIG. 7 is a diagram typically showing the file structure of a comment file.

FIG. 8 is a diagram typically showing the file structure of a file which should be transferred.

FIG. 12 is a diagram showing a display example of the initial picture of item "input/reference."

FIG. 13 is a diagram showing a display example of a basic picture of item "patient information."

FIG. 16 is a diagram showing a display example of a picture at a transference inputting time.

FIG. 17 is a diagram showing a submenu of image taking-in.

FIG. 22 is a diagram showing one example of a nursing record input picture.

FIG. 27 is a diagram for explaining transmission of data which should be transferred by a facsimile machine or an electronic mail for a wide use.

FIG. 28 is a flow chart showing a processing flow from a data file input to information transference.

FIG. 32 is a diagram showing one example of a data base to which a receiver is registered for each destination.

FIG. 33 is a diagram showing one example of a data base to which a receiver is registered for each destination.

FIG. 34 is a diagram typically showing the structure of a comment file (a file which should be transferred) according to another embodiment of the present invention.

FIG. 41 is a diagram typically showing the structure of a comment file (a file which should be transferred) according to still another embodiment of the present invention.

DETAILED DESCRIPTION OF THE PREFERRED EMBODIMENTS

With reference to the drawings, embodiments of the present invention will now be described.

The present invention can be applied to, for example, a home-based care operation, and can also be applied to a system for supporting various operations for mobile workers in which a team of persons in charge is organized and the persons in charge alternately go to a destination as in a maintenance operation of a plant or the like, a maintenance service operation, a guarding operation of a building or the like, sales or the like, and persons except for the predetermined persons in charge take charge of such operations in an emergency situation. However, in this embodiment, description will be performed about an operation supporting system adapted to the so-called home-based care operation as an example. In this operation supporting system, plural visiting nurses belonging to a visiting nursing station alternately visit a patient in a rotation system to perform a visiting nursing operation.

First, the visiting nursing operation and its operating supporting system according to this embodiment will schematically be described.

Figure 3:
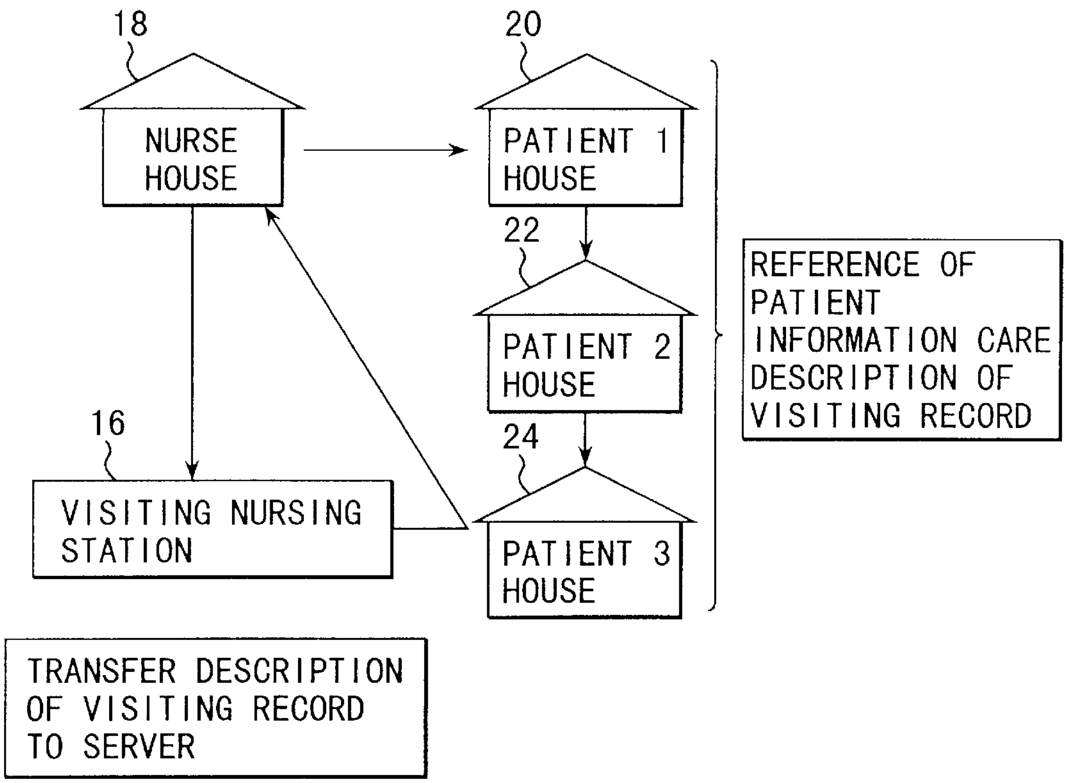
FIG. 3 is a diagram showing one example of the flow of a daily operation of a visiting nurse using this system.

FIG. 3 shows an example of the operation of a visiting nurse. A certain visiting nurse A carries a PDA (a portable information communication terminal) and visits a first patient house 20 from her house 18. The visiting nurse A then gives care to the patient in charge. The visiting nurse A next visits a second patient house 22 and finally visits a third patient house 24 and returns home. Further, the visiting nurse A goes to a visiting nursing station at any time, if necessary. On another day, there is a case in which another visiting nurse B visits the second patient house.

In general, a person in charge (visiting nurse) and a family doctor, etc. are determined for each patient and a schedule for making each visiting nurse visit each patient house is made, for example, each month.

In the visiting nursing operation, each visiting nurse carries the PDA and visits each patient house and gives care to the patient. In this embodiment, it is, as described above, assumed that some visiting nurses alternately give care to one patient (there is also a case in which one visiting nurse gives care to one patient). Further, it is also assumed that one visiting nurse gives care to plural patients (there is also a case in which the visiting nurse gives care to only one patient).

Data generated attributable to the care of a certain visiting nurse for a certain patient is collected from each PDA to a server device disposed in a visiting nursing station 16 or the like by data communication or the like at appropriate timing so that data items are concentrically managed as a data base. A file of these uploaded data items includes a patient ID, information relative to visiting date and hour (e.g., visiting year, month and day, and a visiting time), the ID of a visiting nurse (ID of the person in charge), a state of the patient and the contents of treatment. As will be described later, this file as well as includes comments, information which should be transferred to another nurse or doctor in charge (and information indicating the destination) and the like, if necessary.

In this embodiment, data to be inputted to the PDA is divided into fixed type information having fixed items and unfixed type information permitted to be written freely so that both operability and flexibility of the system are realized.

Information is managed by various data bases on a server device side. As for information peculiar to the patient, the data bases are managed by dividing these information items into information (patient information) unchanged or almost unchanged such as the date of patient's birth, a patient's address, etc., and information (visiting record) changed at each visit or often changed such as a patient's body temperature and contents treated at a visiting time. Data relative to the visiting record are mainly uploaded to the server device from the PDA.

When some visiting nurses alternately give care to one patient, data on this patient generated attributable to the care of another visiting nurse exists on the server device side (if these data items are uploaded). Accordingly, for example, when the previous visiting person in charge of a certain patient A is different in care from the present visiting person in charge of the same, the present visiting person in charge is able to obtain and read data on the patient A generated in the previous visit before the execution of care by downloading these data items from the server device.

In this embodiment, the person in charge giving care to a certain patient is permitted to transfer information which should be transferred to the next person or doctor or the like in charge. As for this information which should be transferred, data including this information is uploaded from the PDA side. Thereafter, "contents of information which should be transferred" and/or "a message showing existence of information which should be transferred" is transmitted to a predetermined receiver (a mail server within the system, a facsimile machine, an electronic mail for a wide use such as E-mail, a pager, etc.) of a person automatically addressed as a destination on the server side. Thus, for example, the person receiving the "contents of information which should be transferred" by the facsimile machine can rapidly and reliably read the contents of information which should be transferred. Further, the person receiving information of the "message showing that there is information which should be transferred" can similarly read the information which should be transferred by downloading the "contents of information which should be transferred" from the server device or the like of the visiting nurse station. In the case of an electronic mail for a wide use, a person gets access to a mail server (e.g., a mail server in personal computer communication) belonging to this person and reads the mail and checks the information which should be transferred.

First to third embodiments of the present invention will now be described.

As will be described later in detail, the first to third embodiments basically have similar structures. However, comment/information which should be transferred, a file format, an input picture, a basic transitional relation between pictures, making of the information which should be transferred, designation of a destination, processing for sending the information which should be transferred in the server device are slightly different from each other.

(First Embodiment)

A first embodiment of the present invention will now be described.

Initially, the basic structure of a home-based care operation supporting system according to the embodiment of the present invention will be described.

Figure 1:
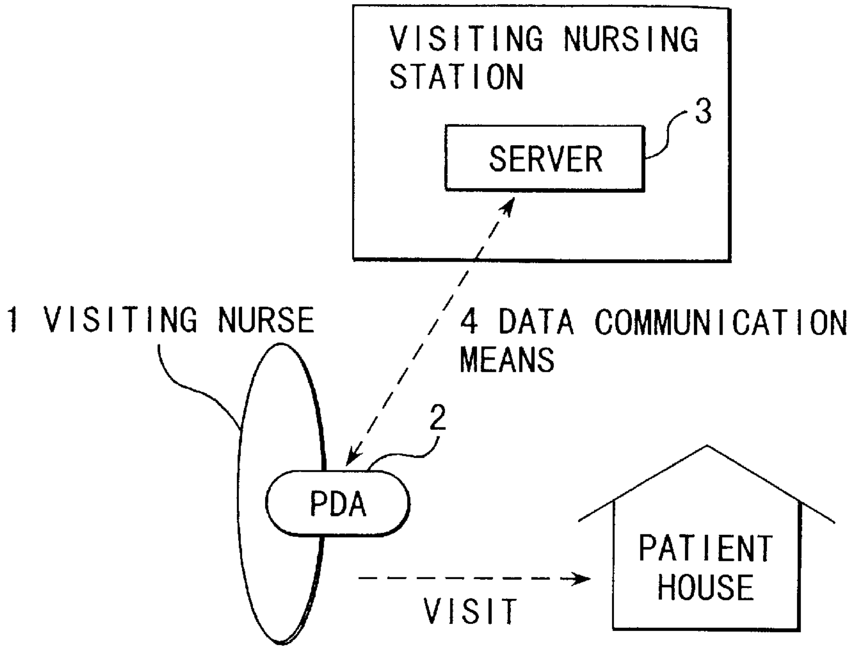
FIG. 1 is a diagram showing a first basic structural example of a home-based care operation supporting system according to an embodiment of the present invention.

FIG. 1 shows a first example of the basic structure of this operation supporting system.

This operation supporting system has a PDA (a portable information communication terminal) 2 carried by each visiting nurse (reference numeral 1 in FIG. 1) and also has a server device (information processing means) 3 disposed in a visiting nursing station to collect and process information inputted to the PDA 2.

In this embodiment, the server device 3 is disposed in the visiting nursing station, but is not limited to this arrangement. The server device 3 may be disposed in, for example, a home-based help supporting center, a hospital, a local self-governing body or the like. Namely, the server device 3 may be disposed in any place in which information can suitably concentrically managed.

When the visiting nurse 1 visits a patient's house and gives care to the patient, the visiting nurse 1, in the patient's house (and/or, thereafter, in another place such as a nurse's house) inputs various information items to the portable PDA 2. Then, the information inputted in the patent's house or the another place is transferred from the PDA 2 to the server device 3 through a predetermined data communication means 4.

The server device 3 adds the received data to an unillustrated data base and makes a file which should be transferred in accordance with instructions and transfers this file, which should be transferred.

The PDA downloads required data from the server device 3 through the predetermined data communication means 4.

The data communication means 4 may be realized by using any method such as (1) an off-line method using a floppy disk or an IC card, (2) a method using an ISDN line when a signal is transmitted through a modem on a usual telephone line, or (3) a method for transmitting a signal by wireless using a portable telephone or a simple portable telephone (PHS) on the PDA side, (4) a method for communicating data by directly connecting the carried PDA to the server device by optical communication or the like when a visiting nurse stops at the visiting nursing station. When the above methods (2) and (3) are used, it is possible to further reduce a time lag until data is completely uploaded to the server device 3 from a moment at which these data items have been generated and inputted to the PDA 2. As a matter of course, plural arbitrary data communication means may be provided.

(1) Each PDA 2 and the server device 3 have a floppy disk drive when a floppy disk is used, and have a card slot when an IC card is used. (2) Each PDA 2 and the server device 3 have a modem when a telephone line (both analog and ISDN lines) is used. As an alternative to this, (3) when wireless is used, each PDA 2 and the server device 3 have a portable telephone or a simple portable telephone (PHS) therein, or can be connected to these telephones. (4) When each PDA 2 and the server device 3 are directly connected by optical communication or the like, each PDA 2 and the server device 3 have a connecting device adaptable to an employed connecting method.

Figure 2:
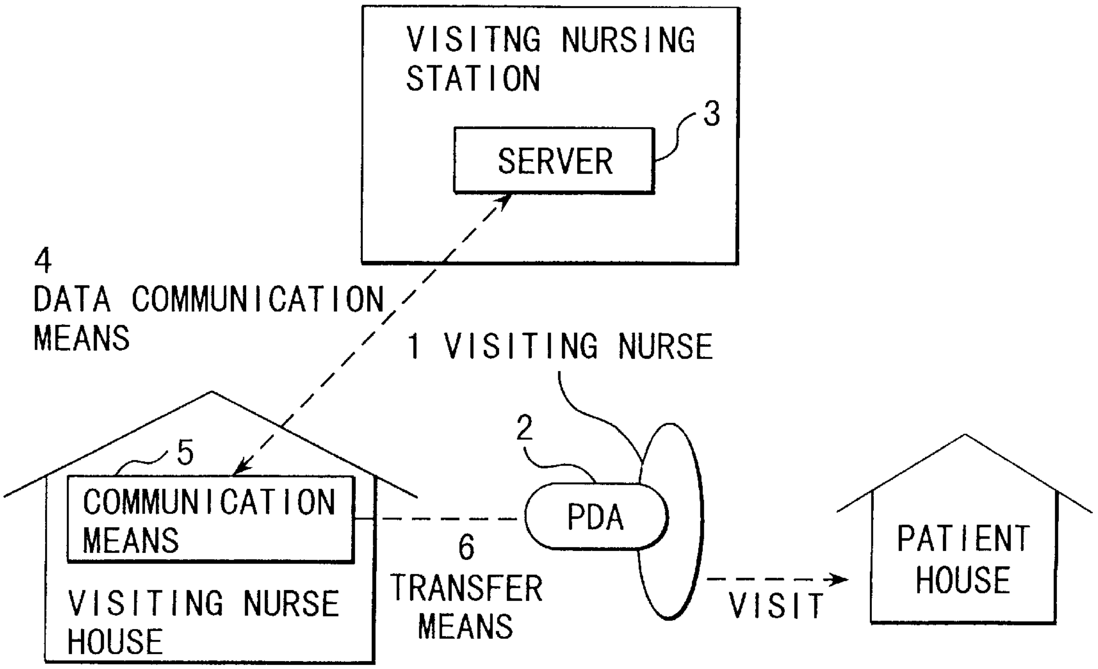
FIG. 2 is a diagram showing a second basic structural example of the home-based care operation supporting system according to the embodiment of the present invention.

FIG. 2 shows a second basic example of the structure of the operation supporting system.

This operation supporting system has a PDA 2 carried by a visiting nurse (reference numeral 1 in FIG. 2), a computer (first information processing means) 5 disposed in a house or the like of the visiting nurse 1, a server device (second information processing means) 3 disposed in a visiting nursing station or the like for collecting and processing information inputted to the PDA 2, and a data communication means 4 for connecting the server device 3 to the computer 5.

When the visiting nurse 1 visits a patient's house, the visiting nurse 1 inputs various information items to the carried PDA 2. When the visiting nurse 1 visits the patient's house and gives care to the patient, the visiting nurse 1 inputs various information items to the carried PDA 2 in the patient's house and/or thereafter, another place such as the nurse's house. The visiting nurse 1 returns home after this visit. Thereafter, the visiting nurse 1 transfers the visiting information previously inputted to the PDA 2 to the computer 5 from the PDA 2 by a predetermined data transfer means 6.

The information transferred to the computer 5 is transferred to the server device 3 by the above-mentioned predetermined data communication means 4.

The server device 3 adds the received data to a data base (not shown) and makes and transfers a file which should be transferred to follow instructions.

When data is downloaded from the server device 3 to the PDA 2, required data is temporarily downloaded to the computer 5 from the server device 3 through the predetermined data communication means 4 and are transferred to the PDA 2 from the computer 5 by the data transfer means 6.

The data communication means 4 may be constructed by personal computer communication or any method such as the above-mentioned methods. When the above methods (2) and (3) are used, it is possible to furthermore reduce a time lag until data have been completely uploaded to the server device 3 from a moment at which these data items have been generated and inputted to the PDA 2. As a matter of course, plural arbitrary data communication means may be provided.

The data transfer means 6 may be realized by (information transferred to a family doctor, a main person in charge or the like obtained for example, after a visit).

Data generated by the operation of a visiting nurse and uploaded from the PDA 2 to the server device 3 is mainly visiting record information. Comment and information which should be transferred are added to this visiting record information, if necessary.

The comment and the information which should be transferred correspond to any item of the patient information and the visiting record. The comment is a memorandum described in a free format. In contrast to this, destination information is added to the information which should be transferred, and contents of information which should be transferred or a message showing that there is information which should be transferred is transmitted to a destination through the server device.

The structure of patient data will now be described.

Figure 4:
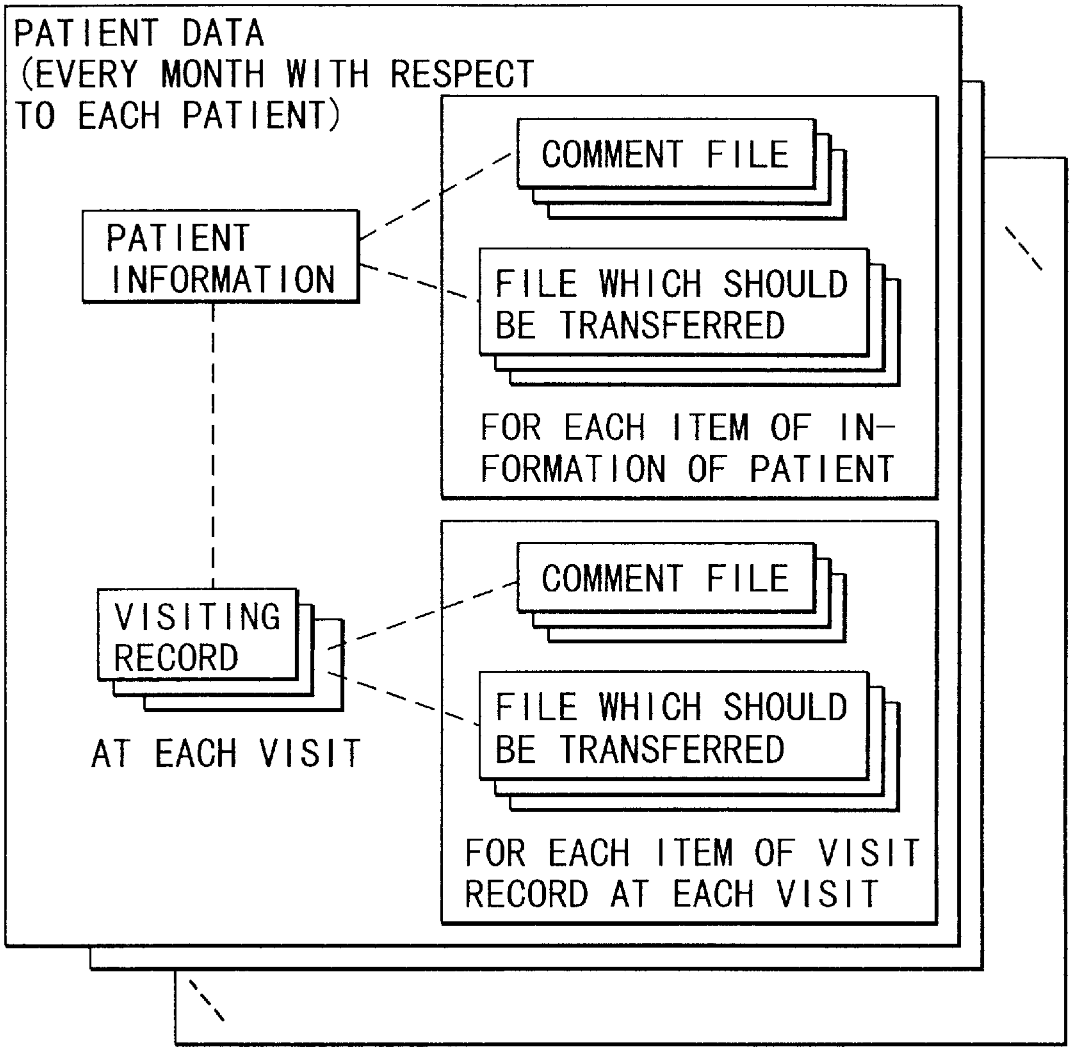
FIG. 4 is a diagram typically showing the basic structure of a patient data base.

FIG. 4 shows an example of the structure of the patient data.

In the patient data, fixed type information is divided into "patient information" and "visiting record." The patient information is described on a patient information work sheet and the visiting record is made on a visiting record work sheet. One patient information work sheet is made for each patient and each predetermined period (in this embodiment it is set for each month). One visiting record work sheet is made for each patient and each visiting time.

A comment file and a file which should be transferred are arbitrarily made as unfixed type information different from the above fixed type information. In these files, arbitrary information relative to a required item of the above fixed type information is recorded as comments or information which should be transferred. Each of these files is made whenever each file is opened.

A patient ID number is written to each of headers or the like of the patient information work sheet, the visiting record work sheet, the comment file and the file which should be transferred so that respective data items are linked to each other.

The visiting record work sheet, the comment file and the file which should be transferred are made at each visit so that these data items are linked to each other by information (visiting date information or visiting time ID) for specifying the visiting time).

An address in a corresponding item is written to each of the headers of the comment file and the file which should be transferred so that items corresponding to the respective files are linked to each other. a method using a floppy disk or an IC card, optical communication, or a method of wire communication using RS232C or the like. As a matter of course, plural arbitrary data transfer means may be provided.

In the structure of FIG. 2, the above-mentioned data communication means for connecting the PDA 2 and the server device 3 to each other may be provided, and data may be directly transferred from the PDA 2 to the server device 3 in the visiting nursing station. In this case, the computer 5 is used to mainly refer to patient data and add/correct the patient data.

Both means for directly communicating data between the PDA 2 and the server device 3 and a means for transferring data to the server device 3 from the PDA 2 through the computer 5 may be provided.

In this embodiment, the PDA 2 is set to have a pen inputting function by moving a pen on a display screen. The PDA 2 is realized by executing software on a CPU. This software performs predetermined information process and controls the operation of an input-output device, such as a pen input device and a display unit.

The server device 3 is realized by executing software on the CPU. This software performs predetermined information process and controls the operation of an input-output device such as a keyboard, a mouse, and the display unit.

A data base managed by the server device 3 is stored into, for example, a memory device such as a hard disk or the like built in the server device 3, or a memory device (not shown) such as a hard disk externally connected to the server device.

The PDA 2 has a function for inputting information and referring to information. In the visiting nursing operation, a recording format such as visiting nursing record documents I, II is determined at present and fixed type information is inputted/referred in accordance with this format.

In the following description, the PDA of a pen input type and having a card slot is taken as an example, and input/reference of information in this PDA will be described.

Initially, information treated in this operation supporting system will be described.

Main information treated in this operation supporting system is patient data, and patient data is composed of the following four types of data items.

(1) Patient information (static information such as a disease situation of each patient and a disease history)

(2) Visiting record (information recorded by a person in charge such as a nurse or the like at a visiting time).

(3) Comment (4) Information which should be transferred

FIGS. 5A through 5D show an example of the structure of the patient information work sheet.

As for the patient information work sheet, data in each item is not usually changed in a short after it has been inputted. Accordingly, here, these data items are stored for each month. These data items are updated/added when a state is changed and a monthly summary is inputted.

"Patient information" includes inputted contents of a visiting nursing record document I, a visiting nursing instruction document from a doctor, a monthly visiting nursing plan document and a visiting nursing plan document. Concretely, the patient information includes name, the distinction of sex, address, telephone number, the date of birth, main injury disease names, disease situation, medical treatment state, etc., present medical history, previous illness, life history, family construction and its situation, main helper, living environment, request object, ADL situation, information (name, medical organ name, place, telephone number) of a family doctor, etc., communication method at emergency time, communication destinations of related organs, utilization situation of health-welfare service, etc. [the visiting nursing record document I]. The patient information also includes disease situation, medical treatment state, given medicine, dementia situation, bedridden degree, mounting medical instrument, etc., attention matters on medical care life guidance, treatment of bedsore, etc., operating support and management of mounting medical instrument, etc., method for coping with absent time, and special mention matters [the visiting nursing instruction document]. The patient information also includes monthly past visiting day, disease situation, nursing contents, situation of the helper, etc. [the visiting nursing plan document and the visiting nursing report]. The patient information further includes other inputted information such as classification of insurance.

This operation supporting system reorganizes these data items. For example, these data items are classified into "basic information" common to each document (patient ID, name, the distinction of sex, address, telephone number, the date of birth, main injury disease names, disease situation, medical treatment state, etc., present disease history), "assessment" mainly inputted by a nurse (life history, family construction and its situation, main helper, living environment, request object, ADL situation, classification of insurance), "doctor's instructions" (disease situation, medical treatment state, given medicine, dementia situation, bedridden degree, mounting medical instrument, etc., attention matters on medical care life guidance, treatment of bedsore, etc., operating support and management of mounting medical instrument, etc., method for coping with absent time, and special mention matters), "summary" (past monthly visiting day, disease situation, nursing contents, situation of the helper), and "communication destination" (information of a family doctor, etc., communication method at emergency time, communication destinations of related organs). Further, "synthesis" includes a general opinion and information which should be transferred for recording contents which are not included in the above classified data. The basic information corresponds to a header portion in the patient information work sheet.

FIGS. 6A through 6D show an example of the structure of the visiting record work sheet.

Required information recorded at each time in the normal visiting nursing is based on contents of the visiting nursing record document II. The visiting nursing record document II includes items of "visiting date," "patient state" (body temperature, pulsation, breath, blood pressure and others), "contents of executed nursing and rehabilitation," "others" and "remarks."

In this operation supporting system, the "patient state" is divided into two states composed of a "body state" and a "mental state." The "body state" includes vital data (numeric values) of body temperature, pulsation, breath and blood pressure, and a disease observation. The "mental state" is divided into a degree of stable state, taste, troubles, etc. Further, "family state" is added. In this family state, physical and mental fatigue degrees of a family, etc. are inputted. The "contents of executed nursing and rehabilitation" are shortened to "contents of treatment" and are divided into items of cleaning-wiping, hair washing, sheet exchange, assistance of meal, assistance of excretion, body position conversion, treatment of bedsore, rehabilitation, taking medicine, inspection assistance, environmental maintenance, guidance of a family in helping the patient, management of catheter and bladder washing, management relative to home-based oxygen medical treatment, other diagnosis and treatment assistance, and others, etc. The "others" and "remarks" are summarized as "comments."

Further, patient ID, patient's name, visiting recorder's name or ID (logging-in user ID), visiting date and visiting time are included in a header.

When a rotation system of plural nurses is used, it is necessary to input matters, etc. judged to be transmitted to the next visiting nurse, doctor or the like as matters which should be transferred. Therefore, this item is added as "transference." These classifications are set to be changed at any time by wishes of a user or the like.

When the fixed type information made as a menu as mentioned above is stored in a data base, as shown in FIGS. 5 and 6, numeric value data of the body temperature, etc. are inputted as they are. Degrees (e.g., a stage degree of bedsore) or the like in the respective items are inputted by selecting numbers. Treatments, etc. are inputted to respective corresponding cells. For example, 1 is inputted to a corresponding cell when a treatment is taken, and 0 is inputted to the corresponding cell when no treatment is taken. When plural items are selected, cells are given to all the items and 1 or 0 is similarly inputted to each of these cells. For example, when the number of selectable items is limited to 5, the respective item numbers are inputted to five prepared cells. All of these cells are data cells having fixed lengths.

The "comment" and the "transference" will now be described.

Various forms of the "comment" and the "transference," are considered in view of a file format, an input picture, a method of designating the destination of the transference, etc. Processing on the server device side is slightly changed in a shape corresponding to these forms.

Here, a certain one example will be described and two different examples (second and third embodiments) will be respectively described later.

In this embodiment, information unable to cope with such a fixed type menu is inputted as arbitrary information in shapes of the "comment" and the "transference." The comment and the information which should be transferred are added to all items (all hierarchies and items) of the "patient information" and the "visiting record."

In this case, keys for the comment and the transference are displayed at any time on the screen of the PDA 2. The key of the item intended to be inputted is selected so that an input picture corresponding to each of these items is displayed. Text data is set by using handwriting character recognition, or a bit map area is opened so that the comment or the information which should be transferred is freely inputted and written into the text data or the bit map area. The written comment or information which should be transferred is recorded as an image as it is. As an alternative to this, image (photograph) data may be inputted and a bit map, such as illustrations and characters, may be written onto these image data items. Further, voice data may be recorded onto these image data items.

For example, a patient's face (expression) photographed by a digital still camera or the like and a photograph of a state of the diseased part, such as bedsore, are inputted to the PDA 2 as the image data. Comments may be additionally written to these image data items or voice may be recorded to these image data items. As an alternative to this when, for example, a bedsore position, a mental state of the patient, etc. are graphically inputted as information into a fixed type data input term, corresponding graphic data (fixed type data is already inputted) may be inputted as a bit map to write a detailed opinion about this information and comments may be freely inputted to these graphic data items.

For example, when comments are intended to be written in addition to numeric values of the body temperature or the like, a displayed picture itself is temporarily formed into the bit map and is further inputted and these comments may be manually written. This operation is similarly performed in the case of a graph or the like.

As an alternative to this, the operation supporting system may be used in combination with the above function. For example, a text is inputted as character data by using character recognition and may be written to the bit map on which illustrations, etc. are written with the text as an object. Conversely, the illustrated bit map may be linked to the text and may be displayed. Further, character data and bit map data may be overlapped and displayed and can be inputted by switching these data items.

FIGS. 7 and 8 respectively show examples of data structures of the comment file and the file which should be transferred. As shown in each of these figures, each of these files has a header portion and a data portion.

Serial number, patient ID, patient name, input person name, input date, input time, corresponding item address, classification of data and data size are inputted to the header portion of the comment file. The serial number is numbered in a making order of the comment file in a corresponding item. The patient name and the input person name are automatically inputted from each data base. As for the input date and time, an opening time of each file is set to be automatically written.

In addition to the above data, the header portion of the file which should be transferred is set to have a designated destination ID (destination information). In this embodiment, the destination can be designated for each file which should be transferred.

For example, when a corresponding item is the patient name, the patient name in FIG. 5A is written on a second line in basic information of the patient information. Accordingly, the corresponding item address is represented as (01. 01. 02) by combining patient information address (01), basic information address (01) and second line (02).

When the comment file is then opened, an address in the designated item is automatically detected and information is written to its cell.

As for the classification of data, selection is performed whether data stored into the data portion is a bit map, an image (color, black and white or gray scale), a voice or a text. In the file format, for example, the numbers of longitudinal and transversal bits are recorded for each data classification if the stored data is a bit map. When the color image is recorded in a general format such as GIF, TIFF or PCT, a classification of this format is recorded. As for the voice, only the time of sampling is recorded if a sampling frequency, a quantized bit, etc. are fixed for the device.

Then, text data recognized as characters, the bit map data (including inputted picture data), image data and voice data externally inputted by a digital still camera or the like are recorded to the subsequent data portion as the contents of comments.

Data in each separate item can be collected by retrieving the header portion and can be referred (retrieved) by arranging these data items in a time order from the input date and time.

A fixed data area may be provided for the text data and its file may be extended at any time when the text data is written. As for the image data and the bit map, one file is set in page unit and a page order is recognized in accordance with the serial number. As for the voice, a file size may be varied by inputting all data during a recording time (e.g., during an inputting operation with a pen). Further, the recording time and the file size may be fixed.

A multilink setting operation of the comment and the transference will now be described.

There is a case in which contents of the comment and the information which should be transferred are required to be linked to each other over plural items. In such a case, if information can be divided on the bit map for example, this information is divided and the respective items are again designated. In contrast to this, when this information cannot be easily divided, plural attributes are additionally set. In this case, some kinds of cells (e.g., up to five cells) are additionally provided for a corresponding item number of the header and the plural attributes are added to these cells.

Figure 9:
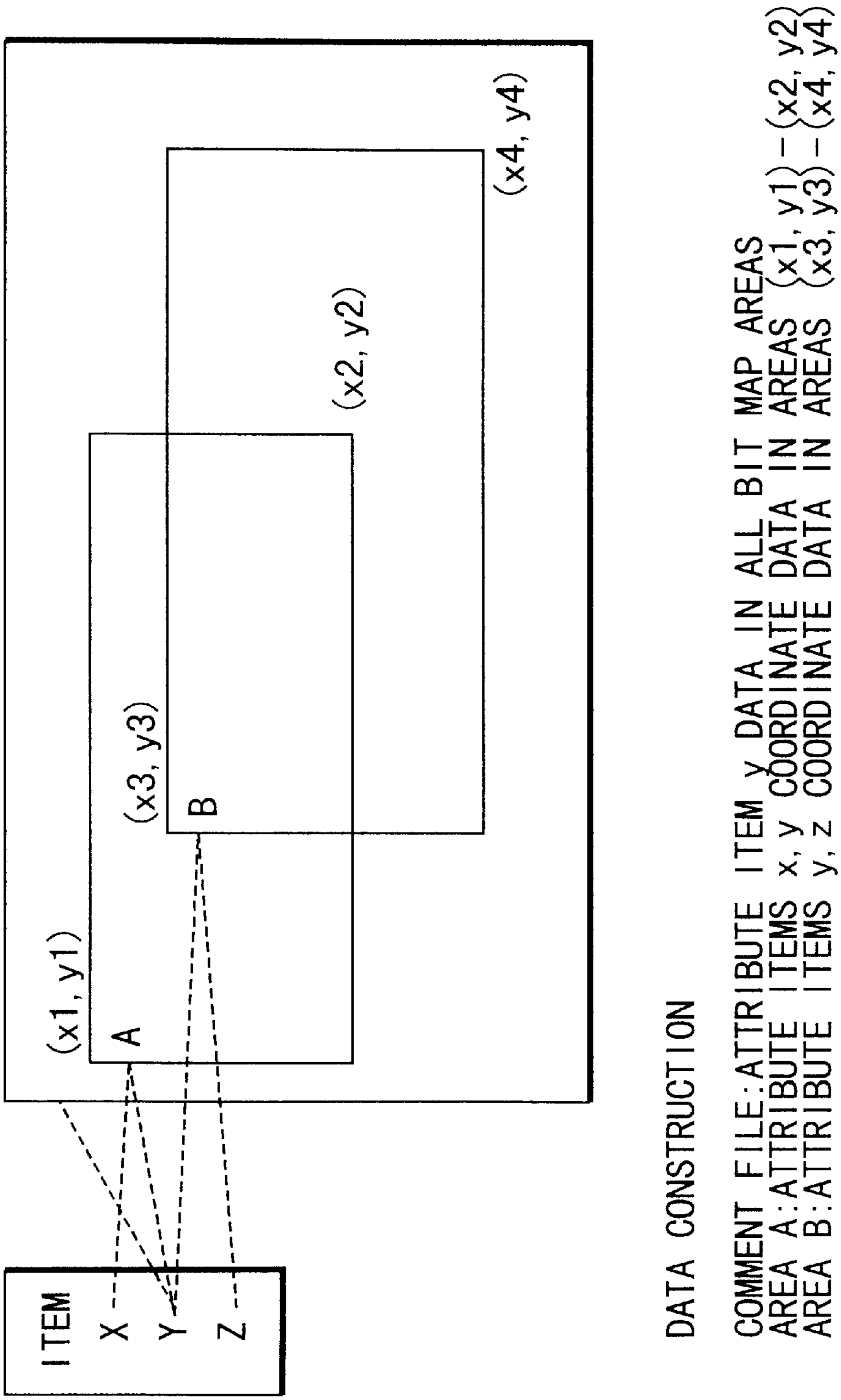
FIG. 9 is a diagram for explaining the concept of a composite attribute of the comment (which should be transferred) file.

FIG. 9 shows the concept of a composite attribute of the comment file or the file which should be transferred.

If the comment file (an item belonging to this comment file at present is set to y) having already written comments is opened, the comments of contents relative to plural items are shown in this comment file. In FIG. 9, an upper area A relates to items x and y and a lower area B relates to items y and z. Contents of these areas are set to be displayed.

In this case, after an area designating key has been selected initially, the area A is designated with a rectangular shape (coordinates: left-hand upper position (x1, y1) and right-hand lower position (x2, y2)) with a pen.

Thereafter, when x and y are selected by an item key, bit map data is newly cut in the designated area A (coordinates: left-hand upper position (x1, y1) and right-hand lower position (x2, y2)) so that a new comment file is made. Then, 1 is inputted to a cell of items x and y as the attributes in this new comment file. As an alternative to this, coordinate data and the file name of an original comment file may be recorded and set to an attribute item so that a new file (a dummy comment file) is made. Similarly, after the area B has been designated, the attribute items y and z are inputted.

When the item y is designated at a reference time (retrieving time), the original comment file and all of data items in the areas A and B are referred. Data only in the area A is referred in the item x and data only in the area B is referred in the item z.

When an attribute item is designated, a designated area is moved to the attribute item with the pen, or the attribute item is conversely moved to this area so that the designating operation is easily performed.

A disease situation, treatment contents, etc. are closely related to each other and treatment contents, etc. expected by a patient are limited. When all the items are displayed, a considerable amount of data is displayed so that the data is displayed in detail, but cannot be seen well. Further, when data is input, it takes time to select items so that there is a possibility that it is complicated to input these data items. Therefore, for example, the item of "contents of treatment" displayed on the PDA 2 can also be limited in accordance with a disease situation and a previous illness of the patient, etc. In this case, a data base for relating the item of the disease situation, etc. to the item of the contents of treatment may be separately prepared. For example, when data is inputted by the PDA 2, only the item of the contents of treatment related to an item selected in "disease situation, medical treatment state, etc." is displayed when the item of the "contents of treatment" is displayed as a list. As an alternative to this, all of the items of the contents of treatment are not given to the PDA 2, but only the related item is linked to patient data and is transferred to the PDA 2 when the patient data is transmitted from the PDA 2 to the server device 3 or the computer 5. This method can be similarly applied if items are related to each other except for the contents of treatment.

A function including each display will now be described along the actual flow of PDA utilization.

Figures 23, 25:
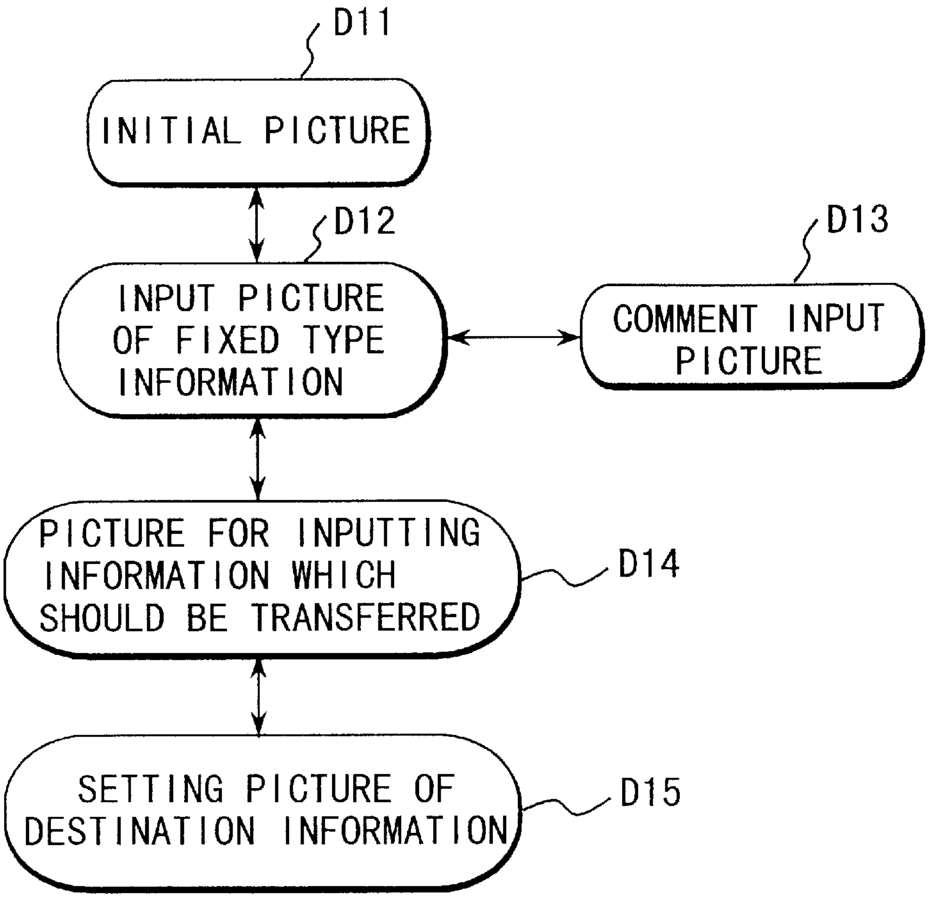
FIG. 23 is a diagram for explaining a basic transitional relation between pictures.
FIG. 25 is a diagram showing one example of correspondence of destination designation and a code.

FIG. 23 is a diagram for showing a basic transitional relation between pictures described later.

Various pictures for input/reference of fixed type information can be transitionally changed from an initial picture. A comment input picture and a transference input picture can be transitionally changed from each fixed type information input picture. A destination information setting picture can be transitionally changed from the transference input picture. In this embodiment, inputting and referring operations are performed in the same picture as an example.

Figure 10:
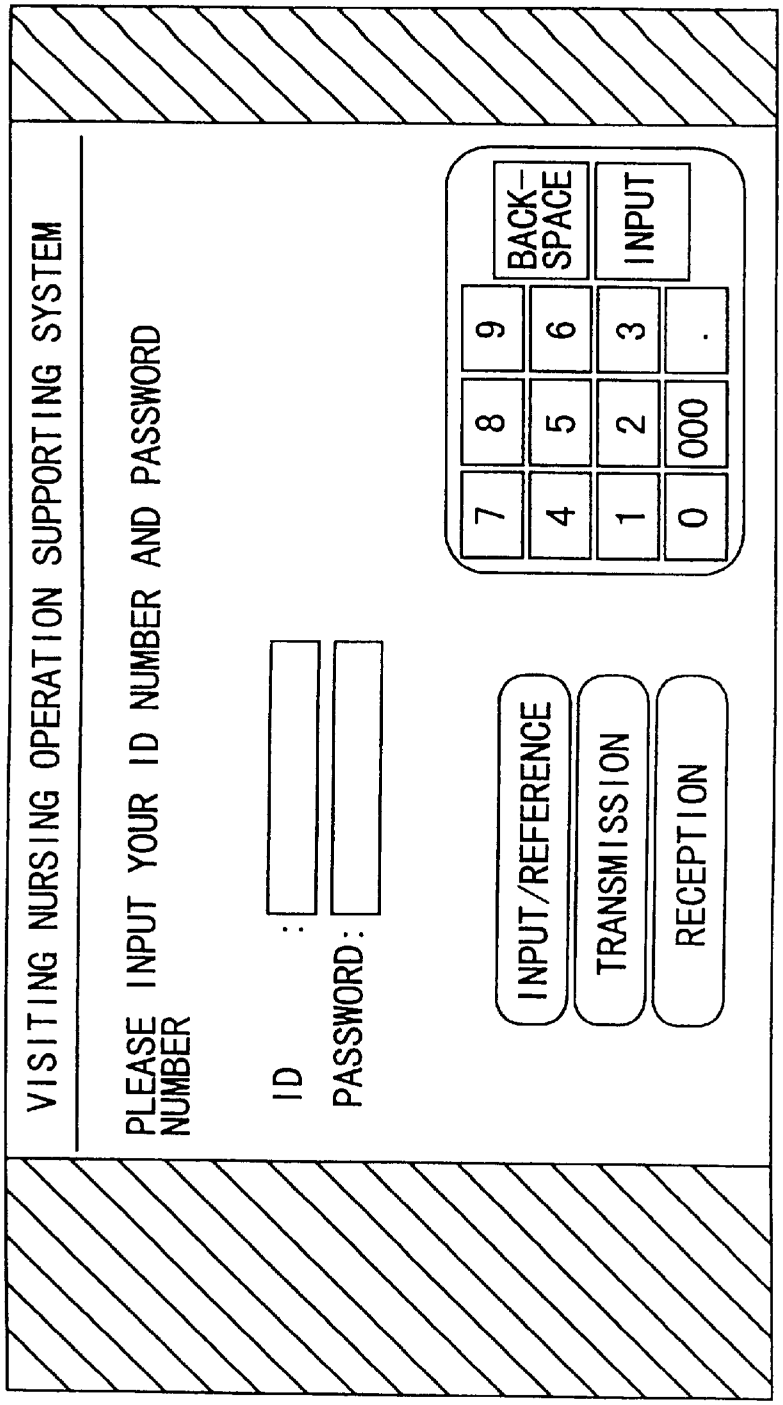
FIG. 10 is a diagram showing a display example of an initial picture of a PDA.

FIG. 10 shows one example of the initial picture of the PDA 2.

This initial picture becomes an input picture of a user ID number and a password (e.g., a number or a combination of alphabets and numbers) of a user (e.g., a visiting nurse). Here, the PDA 2 can be used if the user ID number and the password number as a pair coincide with registered ones. The PDA 2 can also be used even when the user himself is certified by inserting the ID card carried by this user into a card slot. When the user succeeds in log-in, three buttons of "input/reference," "transmission" and "reception" displayed on a left-hand lower side of the screen can be selected.

For example, before a visiting nurse visits a patient's house, the visiting nurse downloads required data from a patient data base of the server device 3 in the visiting nursing station through a communication line using a PHS or the like from her own house or the like. At this time, when the "reception" button is pushed in the initial picture of FIG. 10, her own data of the PDA 2 up to that time are uploaded to the server device 3 and are compared with data of the server device 3. Then, a changing amount of her own data is updated. Thereafter, all patients (only information in which reference of the user is allowed) or the data of plural patients in her charge are downloaded again. This operation may be automatically performed. Before transmitting and receiving operations are performed, a confirmation message of "Is transmission (reception) right?" may be displayed.

When the "transmission" button is pushed, only the above uploading operation is performed.

In this embodiment, the uploading and downloading operations are performed only by selecting the transmission and reception buttons without providing a setting picture for the transmitting and receiving functions. However, a transmitted data file and a data file to be received can be set by forming a transmitting picture and a receiving picture.

Figure 11:
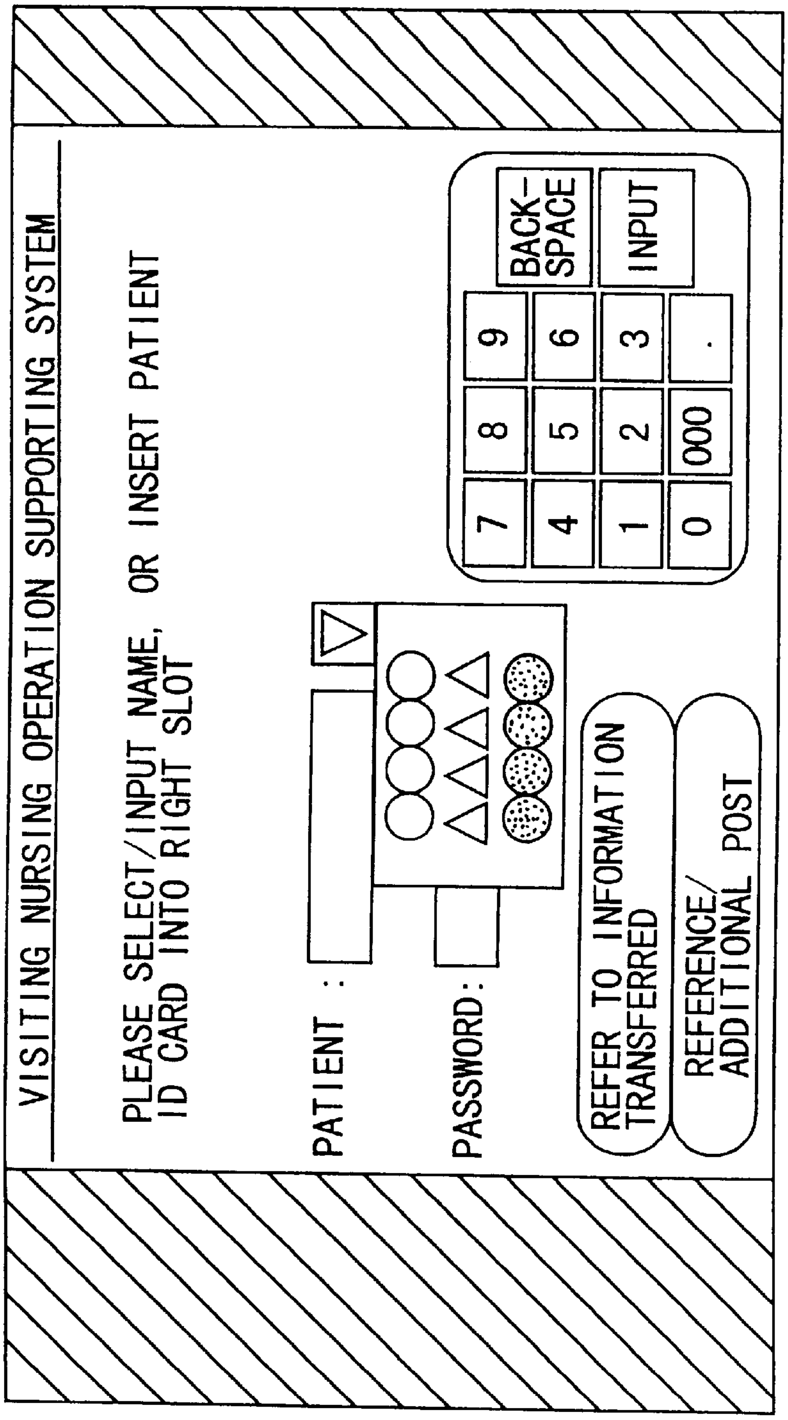
FIG. 11 is a diagram showing a display example of a picture of patient selection and collation in the PDA.

When the "input/reference" button is pushed at a visiting time or the like, a picture as shown in FIG. 11 is displayed. Here, a patient is first selected. When a right-hand key in an input area of the "patient" is pushed, a patient list is pulled down and displayed as shown in FIG. 11 (oooo, etc.). A name is then clicked and selected from this patient list with a pen. When an ID card is sent to the patient, this ID card is inserted into the card slot so that an ID number of the patient is read and a patient data file may be automatically read.

When the patient is selected from the patient list, a password number input area is displayed as shown in FIG.

11 (this area is displayed on the front face when no patient list is displayed). Here, the patient may be collated by inputting the password number by the patient. This means that the collation of the patient also becomes an operating certification.

No patient is collated when only reference of data is required to be performed except for the visiting nursing operation such as a time prior to the visit, and when data is required to be added and written again after the completion of the visiting nursing operation. Accordingly, a "reference/additional writing" key is pushed instead of the input of the password so that a data input/reference picture is displayed. No data can be basically written (corrected and deleted) to files except for the file of the patient to which the visiting nurse makes a visit. However, comments and information which should be transferred (including, for example, questions about data) may be treated such that only addition of data is permitted to any patient file by respectively pushing the "comment" or "transference" keys.

A data input/reference initial picture as shown in FIG. 12 is displayed as one example by making the reference of the patient or pushing the "reference/additional writing" key. First, one of "patient information" and "visiting record" is selected from a menu thereof.

When the "patient information" is selected, a main menu as shown in FIG. 13 is displayed as one example. Data of the patient information is previously inputted at the first and a monthly first registrations. These data items are basically inputted by using a keyboard of the server device 3 disposed in the visiting nursing station or the like or the computer 5 disposed at home. The visiting nurse can input/correct only data of the patient in main nurse's charge.

For example, when "basic information" is selected, name, age, the distinction of sex, the date of birth, address, telephone number, main injury-disease names, disease history, disease situation, medical treatment state, etc., including their contents are displayed as a submenu as shown in FIG. 13. Items subsequent to the address are further inputted in the submenu. When data is corrected, a cursor is moved to a portion to be corrected and these data items are inputted again. There are many contents about "assessment," "indication of doctor" and "summary." Therefore, here, only a menu is displayed and is switched to dedicated pictures for respective items by reselection.

When the "visiting record" is selected in the data input/reference initial picture as shown in FIG. 12, a new work sheet corresponding to that visiting time is opened. First, the input of a visiting date is performed such that the date and hour at a use starting time (patient password number/ID card inputting time) is read from an internal clock of the PDA 2, or is inputted by a ten key pad. Then, a number position is clicked with a pen and black and white inversion is turned on and off. Thereafter, a number inputted by the pad is inputted to the number position. The patient name, the visitor name and the visiting date are displayed at any time.

Figure 14:
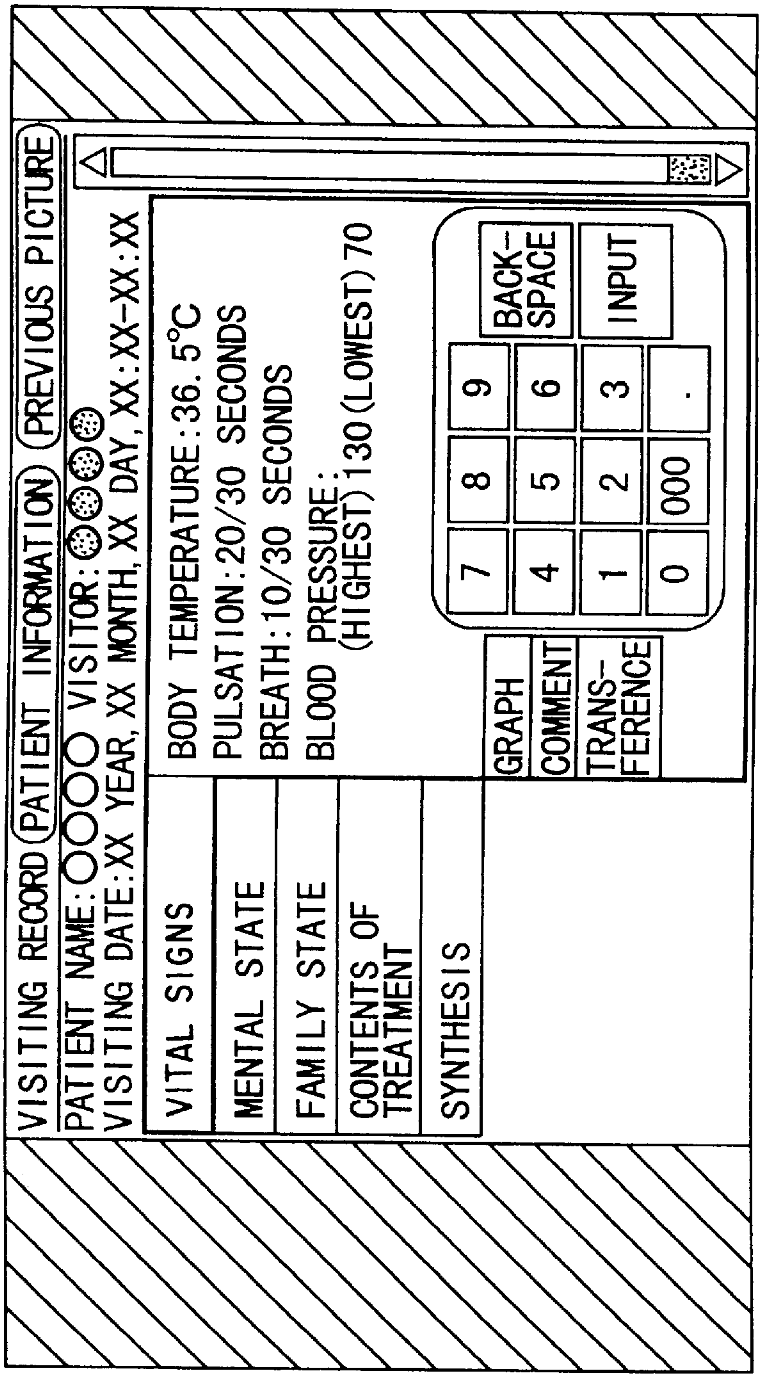
FIG. 14 is a diagram showing a display example of a basic picture of item "visiting record."

For example, the "body state" is displayed on, for example, a display picture as shown in FIG. 14. Body temperature, pulsation, breath and blood pressure are inputted by using the ten key pad and by designating these items by the pen. As an alternative to this, numbers may be manually written by using handwriting character recognition and may be converted to codes so that these items are inputted.

Here, a display portion in a required item is clicked and its characters are inverted to black and white. Further, a display portion of "comment" or "transference" is clicked. In this case, a bit map area capable of performing the handwriting inputting operation is opened. In addition to this, for example, "mental state" may be inputted by graphically displaying and selecting models in which some kinds of man's expressions are typically shown in conformity with stable mental states.

The following description relates to a case in which "comment" or "transference" is added to each of the items. Here, the case of an inputting operation of "treatment of bedsore" in "contents of treatment" will be described as an example. Destination designation of the "transference," etc. will be described later in detail.

First, for example, the "contents of treatment" key is clicked and selected in the display picture as shown in FIG. 14 (the display picture is set to be inverted to black and white). Thus, an item list of the contents of treatment is displayed. Then, a required item is selected from the displayed items by a key. Here, when a "treatment of bedsore" key is selected, a typical map of the body is displayed and a treatment method can be set to be selected from subitems and inputted for each body part. A treated position is set to be colored in black.

Figure 15:
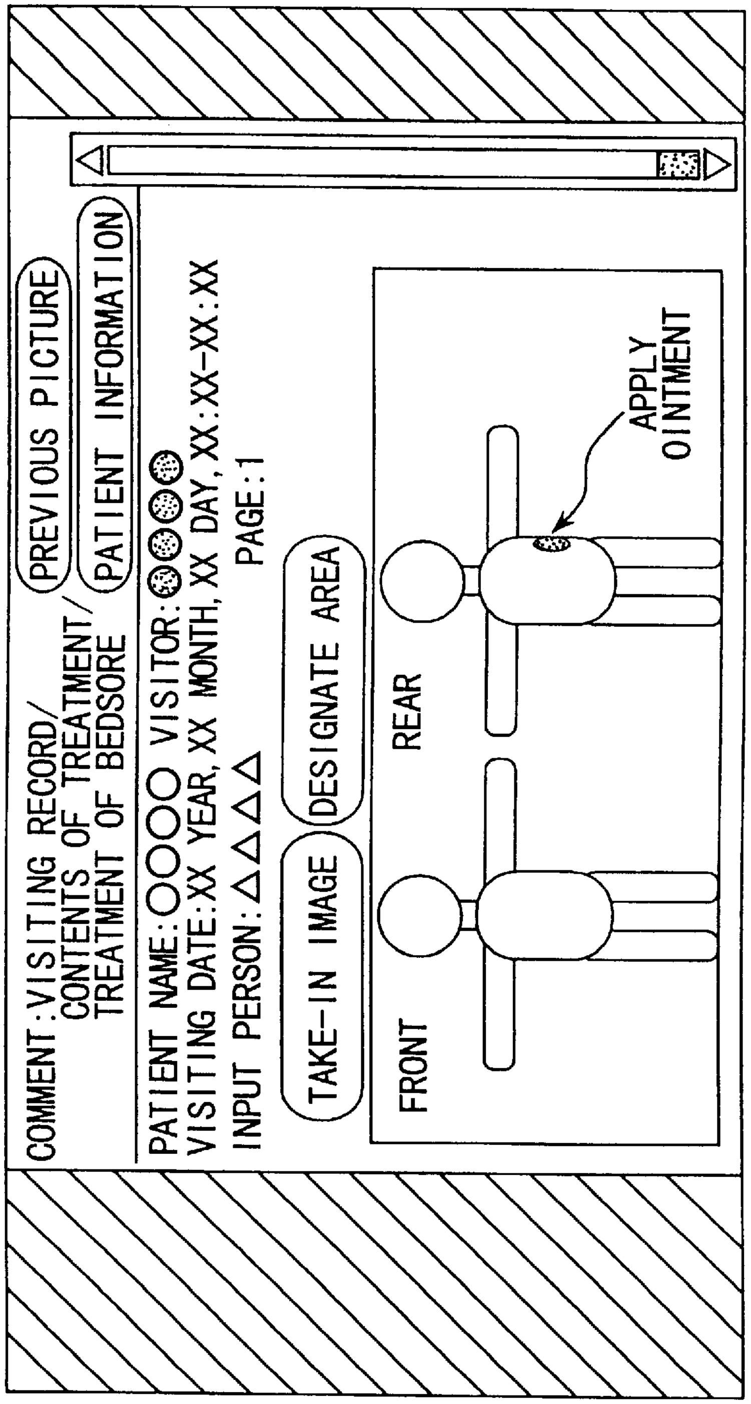
FIG. 15 is a diagram showing a display example of a picture at a comment inputting time.

Further, when unfixed type information, such as comments, or information which should be transferred about these treatments is required to be inputted, the "comment" or "transference" key is selected. FIGS. 15 and 16 show one example of these input pictures.

As shown in FIGS. 15 and 16, hierarchies and items are displayed at an uppermost stage so that the present position and item are seen at a look. For example, FIGS. 15 and 16 show a case in which comments or information which should be transferred is inputted with respect to the "treatment of bedsore" in the "contents of treatment." At this time, "comment: contents of treatment/treatment of bedsore," or "transference:contents of treatment/treatment of bedsore" is displayed at the uppermost stage. Further, the display can be moved (returned) to an upper hierarchy by performing a clicking operation on these characters. For example, the display is returned to a fixed type input picture of the "treatment of bedsore" by performing the clicking operation on characters of the "treatment of bedsore," or clicking a "previous picture" key. The display is returned to the picture of an item list of the "contents of treatment" and a basic item list of the "visiting record" by performing the clicking operation on characters of the "contents of treatment."

With respect to the transference, keys are set to be allocated with respect to destinations often used such as a cooperated doctor, all members of a team giving rotation care, all persons in charge, the next person in charge, persons and all related members. The other destinations are set to be pulled-down and selected. A destination is designated at any time until data is stored (completely written). When a file is closed, the destination is also designated.

Figure 17:
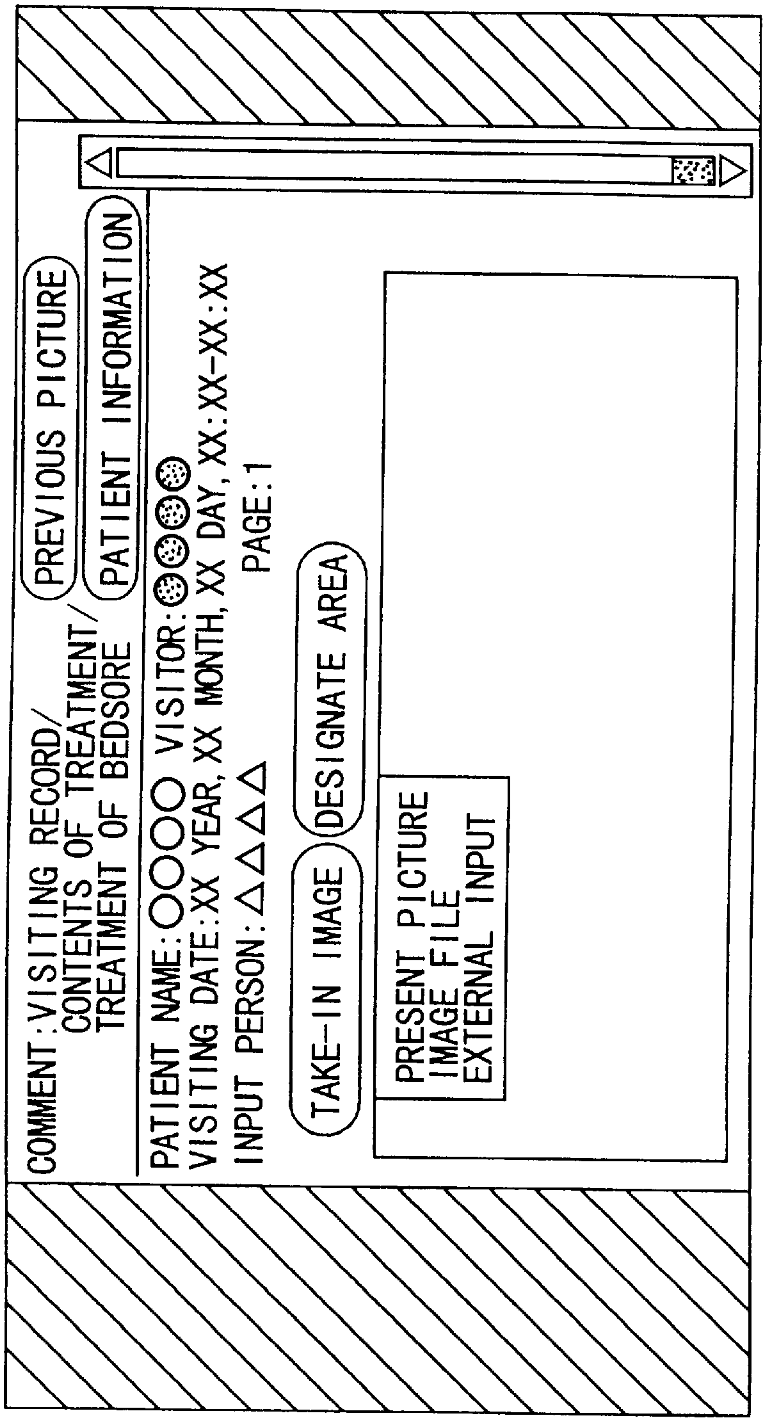

An image input key is prepared in the comment or transference picture. When this key is clicked, a submenu as shown in FIG. 17 is opened. When read image data is selected, the image data is opened and data can be written onto these image data items.

In this embodiment, an input picture is set to be basically used as it is at an information referring time. First, newest data is downloaded from the server device 3 in the visiting nursing station to obtain newest information. When the reception button in the initial picture shown in FIG. 10 is pushed, similar to a taking-out time of data at a visiting time, data is automatically uploaded and downloaded. With respect to a default, for example, a past one month data amount of a patient in user's charge is set to be downloaded. At this time, "patient name" and "period" can be inputted prior to the download so that the patient and period requiring data is set.

For example, past one month data of the patient in charge are set to be downloaded. When these data items are referred, as mentioned above, the patient name is, similarly to the visiting time, designated and the reference/additional writing button is pushed. Thus, the input/reference picture as shown in FIG. 12 is displayed. Reference of fixed type data (fixed type information) and comment (arbitrary information) may be set to be similar to that in a picture at an input time. Thereafter, similar to the input time, a menu key is clicked so that required data is displayed in the same format as the input time.

A new data input picture is set to be displayed at a patient visiting time (at a patient ID card inserting time, or a password number inputting time) in an initial state of data. At a referring time (when no patient is collated), latest visiting data with respect to the patient is set to be displayed.

When data is retroactively referred in a reverse visiting order, for example, a scroll bar displayed rightward is scrolled upward so that the number of visiting times is skipped at one time. In contrast to this, when data is required to be fed for each page, triangular keys located above and below the scroll bar are clicked so that pages is turned one by one. Further, if a concrete date is known, the patient data can be selected by inputting a numeric value to a date display column.

When data not downloaded from the server device 3 to the body of the PDA 2 are accessed, a line is connected at any time and required data is downloaded when a data communication means is constructed by a portable telephone or wireless such as a PHS. In the case of wire or the like, "there is no data" is displayed. At this time, the PDA is connected to a nearest telephone line or the like and the above data is downloaded.

Each item is also selected with respect to comments and data which should be transferred. Further, newest data is displayed (or a new data input picture is displayed) by selecting the "comment" or "transference" key so that dates are retroactively displayed by the scroll bar. When the "comment" or "transference" key is selected in a raised hierarchy state (e.g., "state of body"), all comments or data which should be transferred below this hierarchy are arranged and displayed in the visiting order.

Figure 18:
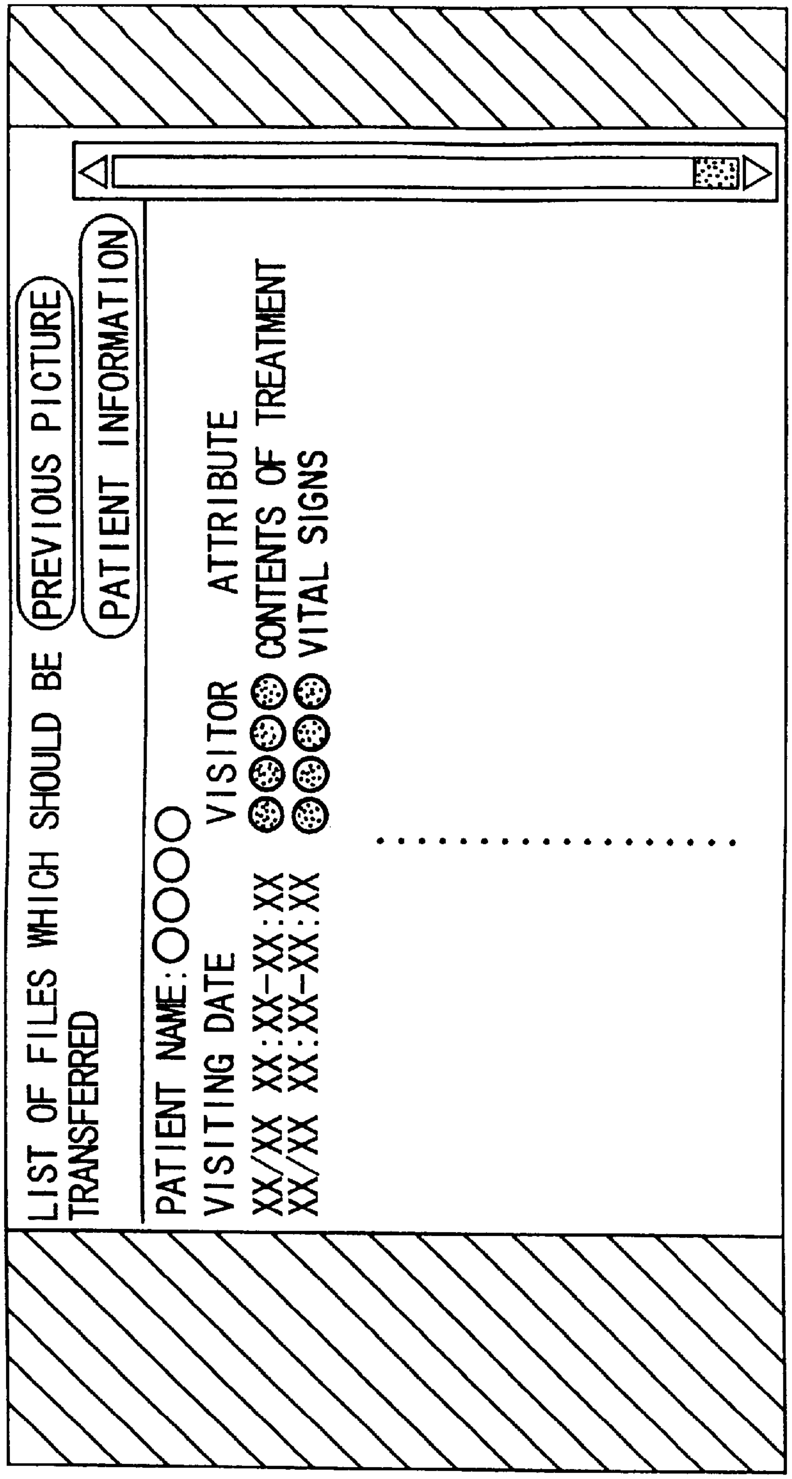
FIG. 18 is a diagram showing a display example of a list display of data which should be transferred.
Figure 19:
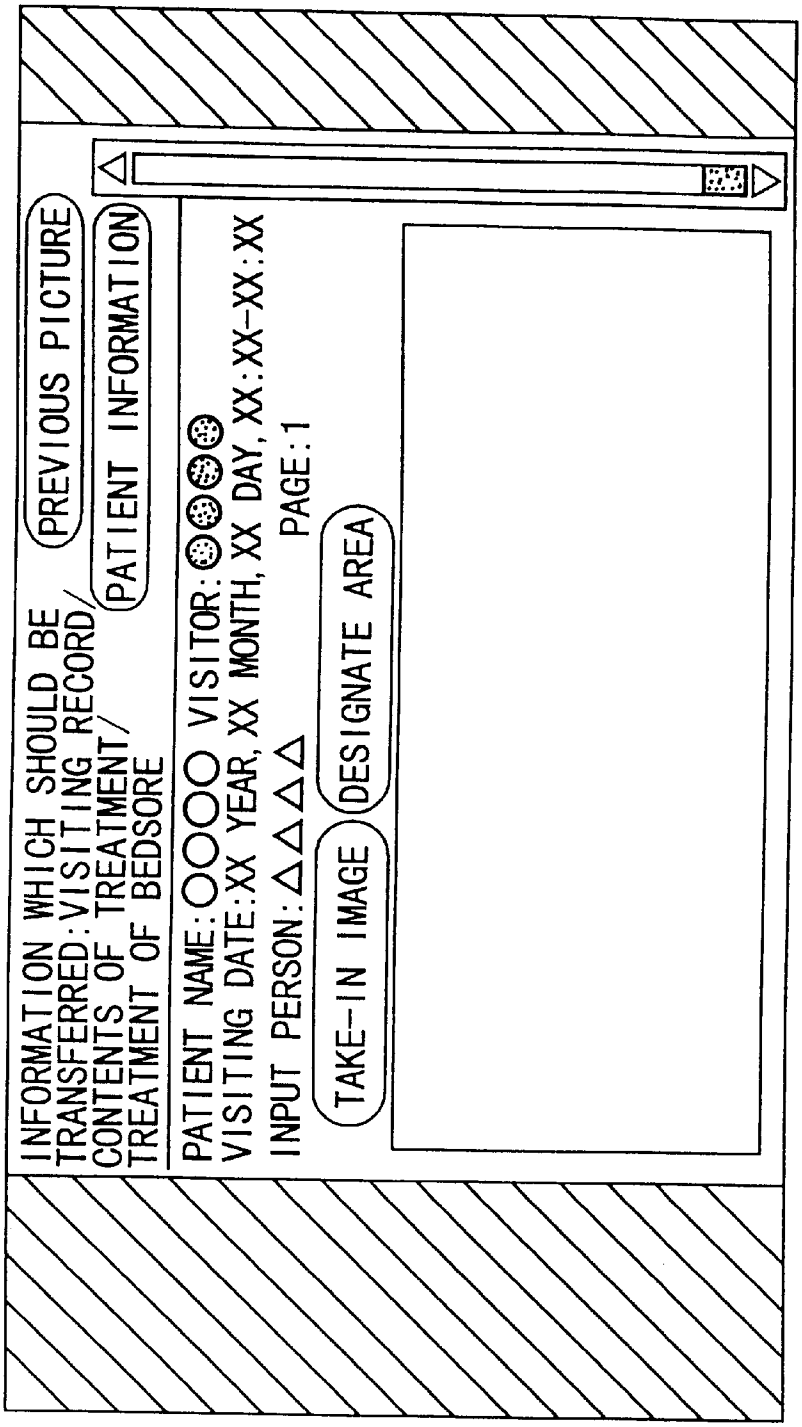
FIG. 19 is a diagram showing a display example of a picture at a transference referring time.

Since destinations are particularly designated with respect to the data which should be transferred, data which should be transferred at one's own destination can be preferably checked together at a rising time of the PDA 2. For example, as shown in FIG. 11, a transference reference key is clicked in a picture opened after one's own password number is inputted. Thus, for example, as shown in FIG. 18, all of unread information items transferred to one's own destination are displayed as a list. A transference picture for a display as shown in FIG. 19 is opened by pushing the reference key so that data is arranged in a reverse visiting order.

Information showing that there is data which should be transferred may be displayed as shown in FIG. 12.

The data which should be transferred can be separately limited and referred for each item. At this time, the item is selected from a menu and the transference key is clicked. In this case, newest data which should be transferred is displayed. Further, similar to the above explanation, the data which should be transferred can be retroactively displayed in the visiting order by the right-hand scroll bar.

Figure 20:
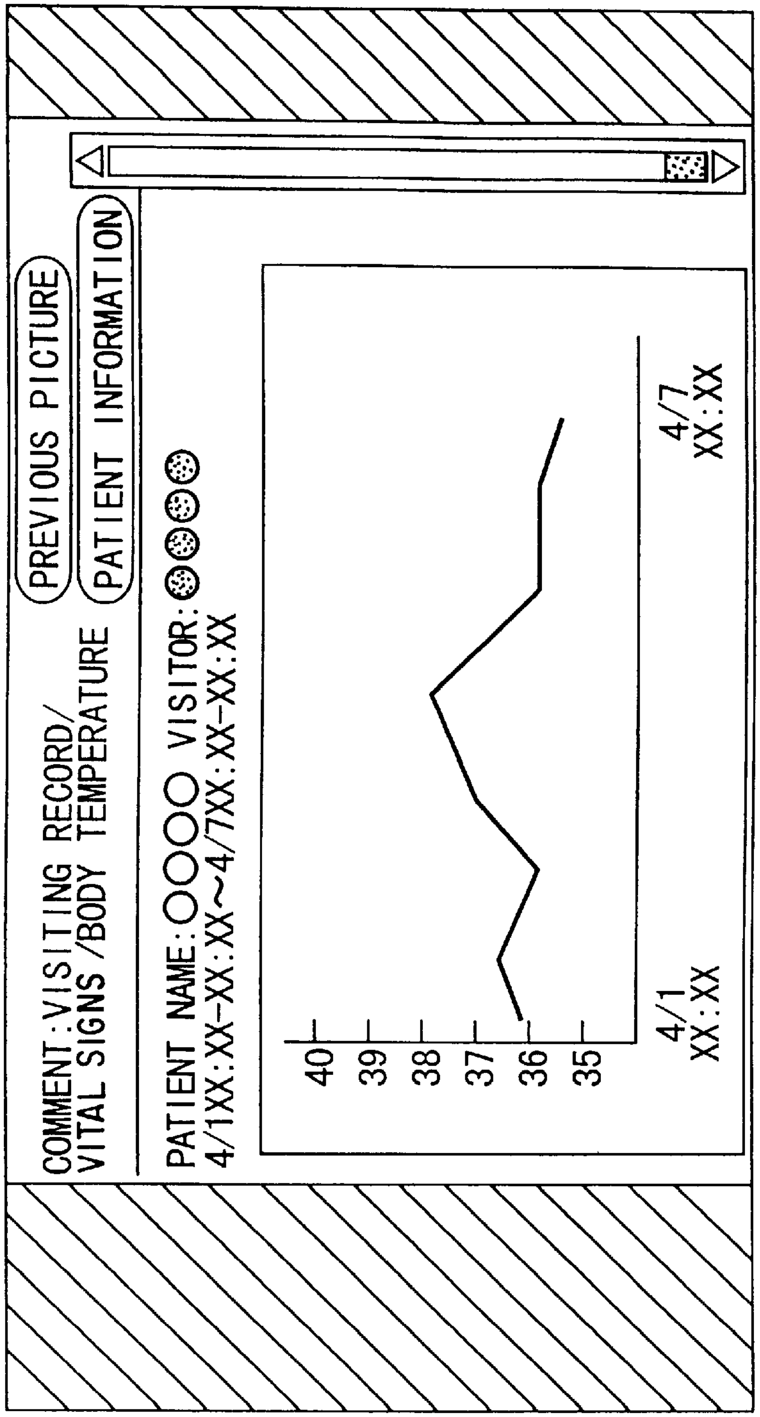
FIG. 20 is a diagram showing a display example of a graph display of vital data.

For example, a latest tendency of various vital data items is preferably displayed by a table and a graph so as to visually know a patient tendency. For example, when the graph of a body temperature is required to be seen, "patient information/basic information/body temperature" is selected. The picture shown in FIG. 14 is set to a state in which characters of the body temperature are inverted to black and white. Here, when a "graph" key is selected, for example, a graph shown in FIG. 20 is displayed. Here, a change in body temperature for past one week is set to be displayed. However, this change in body temperature can also be set to, for example, past one month by changing the setting period. When the axis of abscissa in the graph is clicked, a picture for a setting condition on this axis is opened and the period may be set in this picture.

Figure 21:
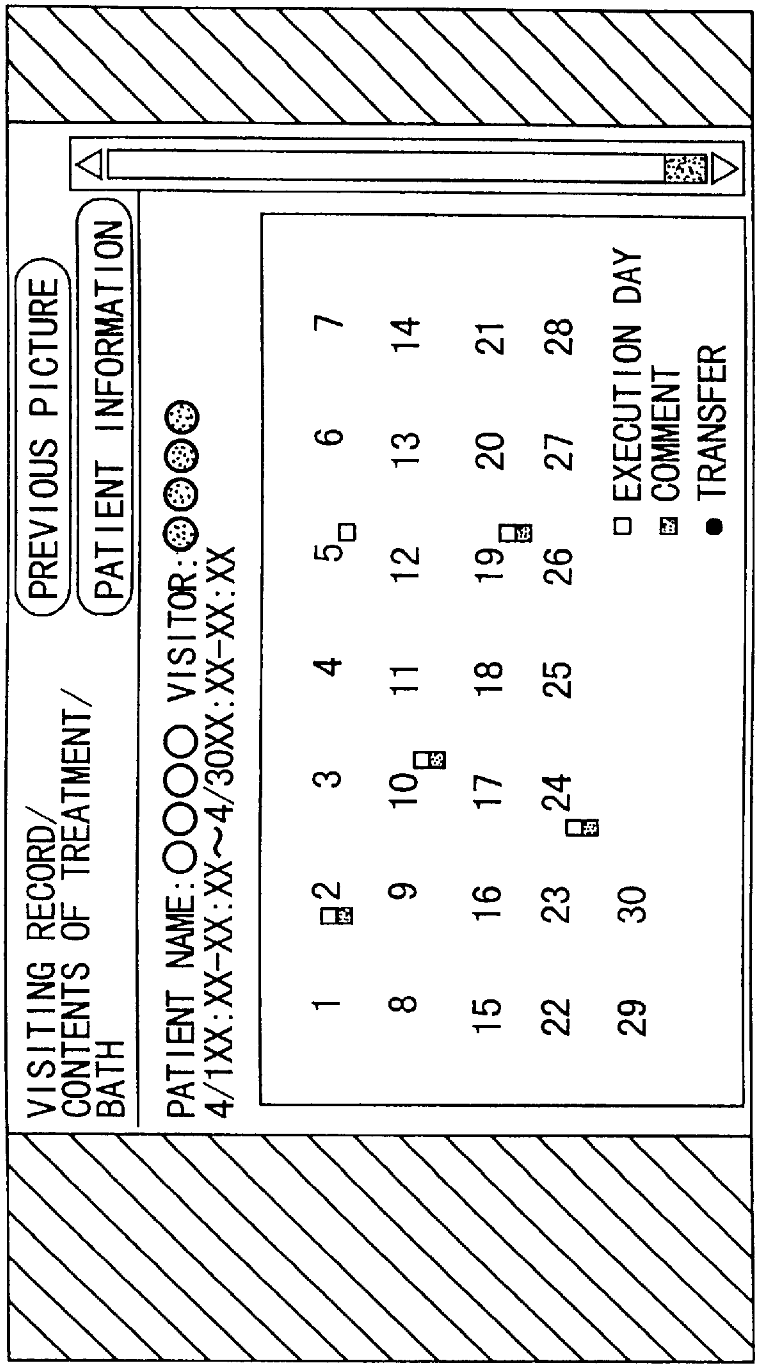
FIG. 21 is a diagram showing a display example in which a past treatment history is graphically displayed.

The contents of treatments, etc. can particularly be displayed as a list for each month or each week as to whether the treatments are taken for each item. For example, a calendar is displayed as shown in FIG. 21 and is automatically colored with a marker on a treated day, or a number showing a date is displayed in inversion. There is a case in which there are plural visits on one day. At this time, positions of the marker are changed (here, the left-hand side shows the morning and the right-hand side shows the afternoon) so that the plural visits are discriminated from each other. Further, some kinds of markers may be arranged. In this case, for example, the input of comment/data which should be transferred is displayed below a treatment marker as shown in FIG. 21. When this treatment marker is clicked, the comment and data which should be transferred can be set to be respectively referred.

Categorization of unfixed type information will now be described.

In the above explanation, the comment and the data which should be transferred correspond to any one of items. However, a new classification (item) can be set in the comment and the data which should be transferred. In the following example, a column of "nursing record" is newly formed in a visiting record file.

FIG. 22 shows one example of a nursing record input picture (one portion of this picture). A "nursing record" button is provided on the left-hand side of the visiting record picture in FIG. 14. When this button is clicked, the nursing record input picture portion is displayed.

The nursing record is basically inputted by a free description (comment file), but can be inputted in a shape describable for each theme (here, the theme is set to a problem point with respect to its patient). Namely, at least a theme number is written to the "nursing record" in the visiting record file. Each theme number and the freely described comment file are linked to each other. Here, a file constructed by a combination of the theme number, a sentence showing contents in the theme number, its setting day (generating day) and a releasing day (a solving day) is independently formed for each patient ID. Both the PDA 2 and the server device 3 are set to hold this file. FIG. 22 displays the theme number on the left-hand side of a picture and its contents (here a problem point) and the generating and solving days on the right-hand side as a list.

These themes can also be set to arbitrarily be registered to the PDA 2. Here, when a blank column is clicked, a board for inputting characters is opened and the themes can be set to be registered by characters using handwriting character recognition and a soft keyboard.

When an inputted problem point display cell is selected in FIG. 22 and a comment key is pushed down, the comment input picture is opened. Accordingly, similar to the above explanation, comments with respect to these problem points can be inputted. At this time, for example, this picture also displays the contents of a problem point such as "#4 helper is wife at advanced age." in a picture title. Here, when destination information is set, the destination information can be set to data which should be transferred with respect to a certain problem point. When these data items are transmitted, the problem point itself is preferably added and transmitted.

A display cell of the generating and solving days is formed on the right-hand side of the problem point display cell. With respect to the generating day, when the problem point is registered, the date of visiting record data opened at that time is registered as a generating day and is displayed in this cell. This generating day can be edited by a ten key pad or the like. With respect to the solving day, when the contents listed as the problem point are solved, the solved problem point is selected and a right-hand upper solving key is then selected. Thus, the date of visiting record data opened at that time is registered as a solving day and is displayed in this cell.

The themes can also be set to be registered at any time on a side of the server device 3.

In the above description, an icon is displayed and the clicking operation is performed on this icon so that input/reference is enabled. However, each document name, etc. may be numbered and selected by inputting this number. Further, an "initial picture" key may be provided so that the display is returned to a basic picture at any time. Further, a "patient information" key may be provided at a visiting record display time and a "visiting record" key may be provided at a patient information display time so that both these keys are switched at any time and information can be referred. Further, when comments or data which should be transferred are referred in an upper hierarchy, it is possible to select whether a lower hierarchy is also referred, or reference is limited to only this upper hierarchy.

Keys used at any time, such as keys for a graph, comments, data which should be transferred, an image input, or ten key pad, may be externally made and disposed in hardware instead of a virtual key arrangement on a liquid crystal. In this case, the number of functions can be increased even when the size of a liquid crystal screen is reduced.

Processes for formation of the data which should be transferred, designation of destination, transmission of the data which should be transferred in the server device, etc. will now be described in detail.

In a visiting nursing operation, no data which should be transferred can be directly transmitted between a visiting nurse and a doctor, or between plural visiting nurses when the plural visiting nurses give care to one patient. Therefore, in this embodiment, a transference distribution function is provided so as to support such a situation.

FIG. 27 shows an entire sequential procedure when a file including the data which should be transferred is transmitted to a designated destination from the server device by a facsimile machine (or an electronic mail for a wide use).

FIG. 28 shows a schematic processing flow to be performed from data input through the PDA 2 to the transmission of the file including the data which should be transferred or a message showing that the data which should be transferred are transmitted by the server device 3.

As mentioned above, the visiting nurse first inputs data to the PDA 2. Fixed type information (step S11), comments (step S12) and data which should be transferred (step S13) are repeatedly inputted to the PDA 2 by a required amount in an arbitrary order.

When a required item (e.g., body temperature) is clicked and a transference button is clicked in an input picture of the fixed type information (e.g., FIG. 14), a bit map area capable of performing a handwriting inputting operation is opened. For example, when the contents of treatment are selected in the visiting record picture and the treatment of bedsore is selected as an item, a bit map area capable of performing the handwriting inputting operation as shown in FIG. 16 is opened.

Here, when input of the transference of information has been completed by describing the information, which should be transferred, or by fetching the image as described above, a destination is next set (step S14). In this embodiment, the destination is set for each file which should be transferred.

An operation for setting the destination is performed by an operating method on a bit map input picture as shown in FIG. 16 and a method in which a destination setting picture is opened when a destination setting button within the bit map input picture is clicked. However, the operation for setting the destination may be performed by using any method.

Here, the following various methods are considered as a designating method of the destination. (1) The destination is abstracted and set. Each destination is coded. A destination ID of the file which should be transferred is set by this code on the PDA side and is uploaded to the server device. The server device retrieves a data base and extracts a concrete destination (information of a recipient's name and a receiver) corresponding to the designated code.

Figure 24:
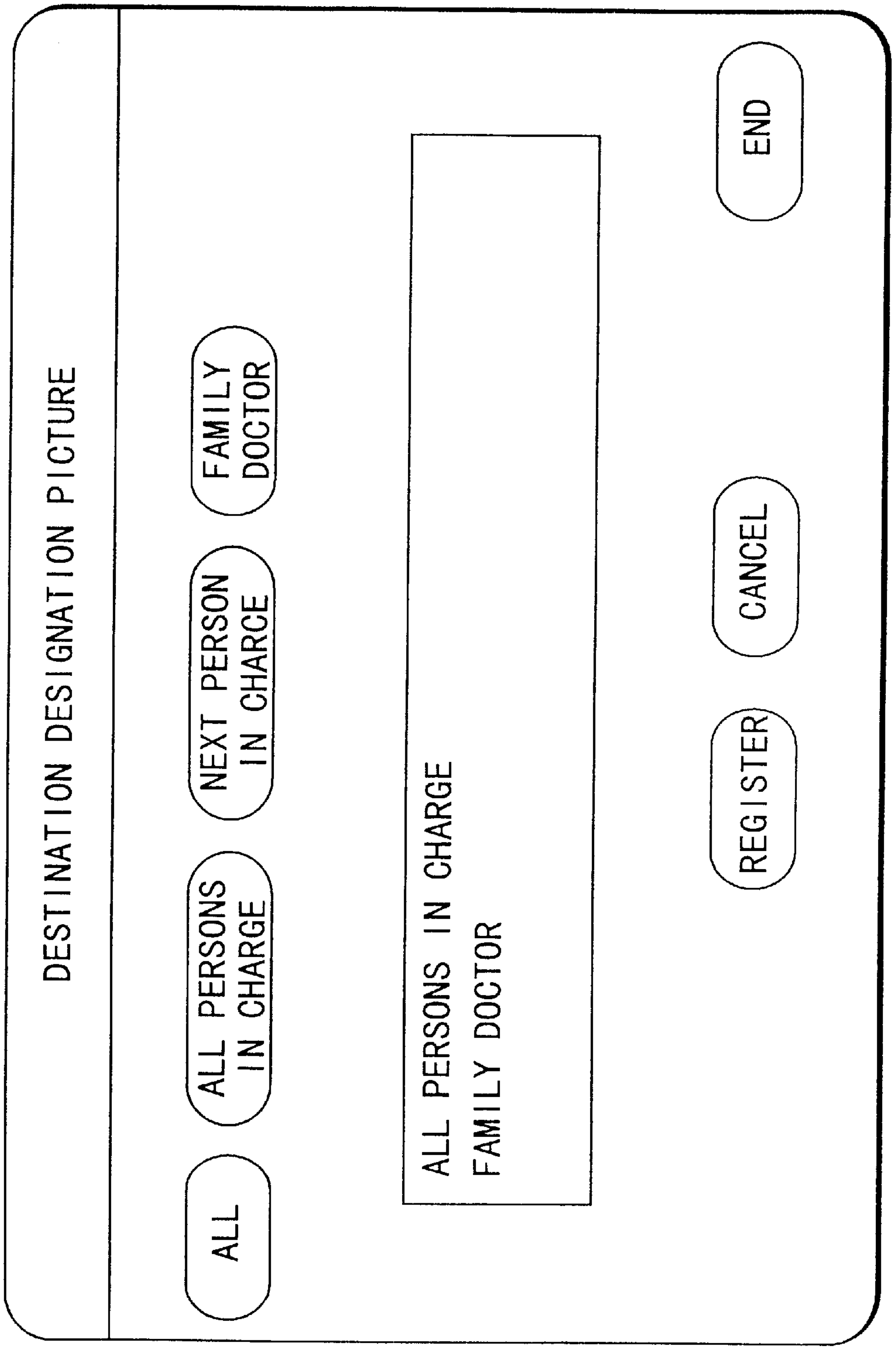
FIG. 24 is a diagram showing one example of a destination designating picture.

For example, as shown in one example of FIG. 25, the destination of all members (all registered members) is set to code 1. The destination of all persons in charge of that patient is set to code 2. The destination of the next person in charge of that patient at the next visiting time is set to code 3. The destination of a family doctor is set to code 4. Further, the destination of all members within a team giving rotation care is set to code 5, and the destination of all cooperated doctors is set to code 6. As shown in FIG. 24, an abstracted destination is selected as a button. When a person in charge clicks a required button and the destination is selected, a selected destination name is displayed. FIG. 24 shows a state in which all the persons in charge and the family doctor are selected. In this case, codes 2 and 4 are set in the destination ID of the file which should be transferred.

(2) In the above method (1), a personal name can be set to be individually selected. For example, as shown in one example of FIG. 26, when a person button is pushed, a list of personal names is displayed and required name is selected from these personal names. In this case, an abstracted code and a personally allocated ID are set in a mixed shape in a destination ID of the file which should be transferred.

In this case, it is necessary to check an overlap-designated person by the abstracted code and the personally allocated ID on the server device side such that no data is doubly transferred.

(3) In the above method (2), only an individual selection of the personal names can be set to be made. [0176]

(4) In the above method (1), an inputting operation is performed at an abstracted destination and this abstracted destination is developed to the personally allocated ID on the PDA side and is uploaded to the server device.

(5) In the above method (2), the destination ID is developed to the personally allocated ID on the PDA side and is uploaded to the server device. In this case, the PDA checks the overlap-designated person by the abstracted code and the personally allocated ID so as not to doubly register this person. Further, when the destination is this person in charge himself, namely, when a logged-in user ID exists, it is necessary to remove this user ID.

(6) It is also considered that destination information designated on the PDA side is developed to information at a concretized level such as information (a recipient name, a user ID, etc.) with respect to a person at this destination, information of its receiver (e.g., the receiver is a facsimile machine and the number of the facsimile machine) by using the above input methods (1) to (3) and is uploaded to the server device. When the destination is this person in charge himself, namely, when a logged-in user ID exists, it is necessary to remove this user ID.

The development of the destination information made in the above methods (4) to (6) is the same as the development of destination information made on the server device side in the above methods (1) to (3) as described later in detail.

Next, a data file including various inputted information items is transferred from the PDA 2 to the server device 3 through a predetermined data communication means 4 by giving commands of signal transmission on the screen (step S15). This situation is shown by reference number 1 surrounded by a circle and shown in FIG. 27.

Thus, the operation on the side of the PDA 2 is terminated.

Next, when the server device 3 receives the transferred data file (step S16), the server device 3 writes this data file to a data base. This situation is shown by reference number 2 surrounded by a circle and shown in FIG. 27.

Next, the server device 3 retrieves a file which should be transferred from the data file written to the data base (step S17).

When there is no file which should be transferred, the processing is terminated with respect to this upload.

In contrast to this, when there are files which should be transferred, destination information is extracted from each file which should be transferred and a concrete destination is determined with respect to each file which should be transferred (step S18).

The determination of the destination is changed in accordance with the designating methods of the destination.

(a) A case using the above destination designating method (1), i.e., a method for setting a code showing the abstracted destination to a destination ID will now be described.

In this case, the following data bases are first prepared on the server device side.

(i) A data base in which correspondence of a patient ID and the IDs (user IDs) of all persons in charge of this patient is recorded.

(ii) A data base in which correspondence of the patient ID and the ID of a family doctor of this patient is recorded.

(iii) A data base in which correspondence of the patient ID, a predetermined visiting date of this patient for a constant period (e.g., a month) and the ID (user ID) of a person in charge of this patient at that visiting time is recorded.

(iv) A data base in which correspondence of IDs of a person in charge and a doctor, etc., a number of its receiver (e.g., the number of the facsimile machine), etc. is recorded.

In this embodiment, a user ID for treating the PDA is allocated to the person in charge, i.e., the visiting nurse. However, when classifications such as doctors, are different from each other, unoverlapping IDs are allocated and managed such that such different classifications can be equally treated in the above data base (iv) or the like with respect to the destination. It is preferable that the classifications whether the visitor is the visiting nurse or the doctor can be discriminated from each other by IDs.

As an alternative to this, a code or the like representing the person in charge or the doctor may be made in the above data base (iv).

The server device 3 specifies the ID of a person at the destination from the destination ID.

For example, when the destination ID is set to 2, the user IDs of all persons in charge can be known from the above data base (i). When the destination ID is set to 3, a user ID at the next visiting time can be known from the above data base (iii). When the destination ID is set to 4, the user ID at the next visiting time can be known from the above data base (ii).

When the destination ID is set to 1, user IDs of all the persons in charge registered in advance, IDs of the doctor, etc. are extracted.

For example, when it is difficult to make the above data base (iii), no designation such as the next person in charge can be made on the PDA side.

Thus, the user ID of a person at one or plural destinations, etc. are determined with respect to each file. When the destination is this person in charge himself, namely, when a logged-in user ID exists (e.g., when all the persons in charge are designated), it is necessary to remove this user ID.

Next, the ID (or a set of this ID and a code representing the person in charge or a doctor) of the person at the destination extracted as mentioned above is set to a key and its receiver number (e.g., a facsimile machine number), etc. are retrieved from the above data base (iv).

Thus, concrete destination information with respect to the person at one or plural destinations can be obtained with respect to each file.

Each of specifications of the above prepared data bases is one example. Accordingly, a data base having another form may also be used. For example, the above contents of the data base (iv) may also be dispersed to plural data bases.

(b) In the above methods (3) to (5), namely, when an ID allocated to a person is set to the destination ID, the data base (iv) is retrieved as mentioned above so that the concrete destination information (e.g., a facsimile machine number) with respect to the person at one or plural destinations is extracted with respect to each file.

(c) In the case of the above method (2), the ID of a person designated by the code of an abstracted destination is extracted. If there is an overlapping portion between this extracted ID and the ID allocated to the person and set as the destination ID, this overlapping portion is removed. Thereafter, as mentioned above, the above data base (iv) is retrieved. Thus, the concrete destination information (e.g., a facsimile machine number) with respect to the person at one or plural destinations is extracted with respect to each file. When the destination is this person in charge himself, namely, when a logged-in user ID exists (e.g., when all the persons in charge are designated), it is necessary to remove this user ID.

(d) In this case, no processing is required here since the concrete destination information (e.g., a facsimile machine number) is designated.

Thus, the concrete destination information such as a receiver number (e.g., a facsimile machine number) is obtained with respect to each file which should be transferred.

With respect to a user (having the PDA) belonging to this system at destinations, patient data is downloaded together as mentioned above and data which should be transferred are referred from these patient data items in one form. In another form, it is considered that a mail server function is provided in this system and a signal is transmitted to this system and the patient data is downloaded together with a mail (the data which should be transferred) at a downloading time.

Next, a file for transmission is made on the basis of the extracted receiver number (e.g., a facsimile machine number), the file which should be transferred to be transmitted, etc. (step S20).

Then, the made file for transmission is transmitted to the designated destination (step S20).

Reference number 3 surrounded by a circle and shown in FIG. 27 shows a situation in which the file which should be transferred from a person #i in charge is transmitted to the facsimile machine of a person #j in charge (or, through an electronic mail for a wide use).

When there are plural file which should be transferred, it is expected that there are file which should be transferred having the same destination. In such a case, the file which should be transferred may be separately transmitted for each file which should be transferred with respect to the same destination. However, it is desirable to transmit the file which should be transferred having the same destination together.

In the above description, after an uploaded file is written to a data base, the data base is retrieved and existence or nonexistence of the file which should be transferred is checked. However, the existence or nonexistence of the file which should be transferred may be checked before the uploaded file is written to the data base.

Further, the existence or nonexistence of the file which should be transferred is checked before the uploaded file is written to the data base. Furthermore, when the file which should be transferred exists, the file which should be transferred may be copied to a predetermined memory area to use this file in processing after a step S19.

In the above description, the file which should be transferred is transmitted at each time at which one data file is uploaded. However, processing after the step S18 may be performed in batches at each predetermined time or whenever a set number of data files is uploaded. In this case, it is necessary to store whether the processing after the step S18 has been performed or not with respect to each data file. For example, each data file can be specified by a set of a patient ID and a visiting date. Accordingly, the system prepares a table of the set of a patient ID and a visiting date in the uploaded data file, and information showing whether the processing after the step S18 has been performed or not. As an alternative to this, the system prepares a list of sets of a patient ID and a visiting date in the uploaded data file in which no processing after the step S18 is performed.

The above description relates to an example in which the contents of information which should be transferred are transmitted. Instead of this, a message showing that the contents of information which should be transferred are sent can also be transmitted.

Figure 29:
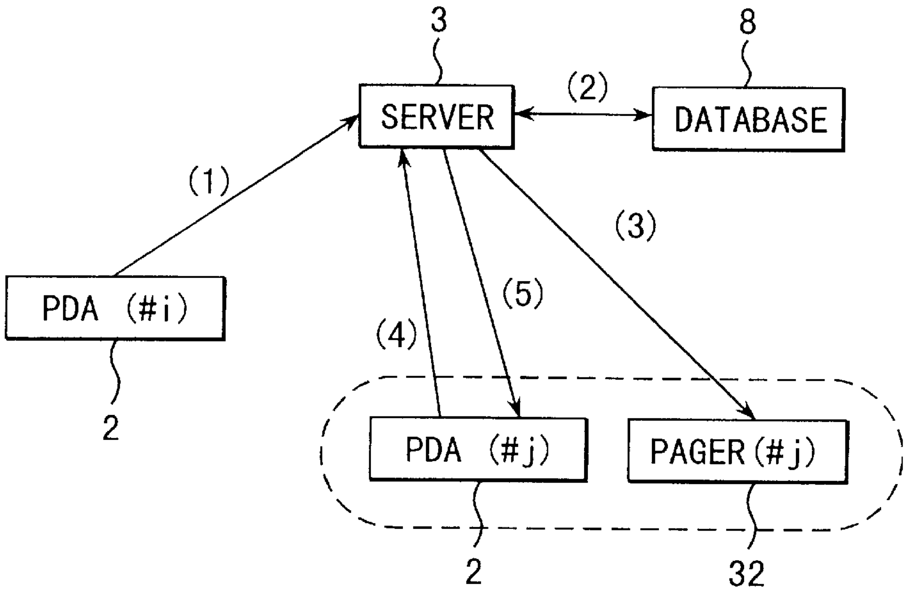
FIG. 29 is a diagram for explaining message communication for the data which should be transferred by a pager.

For example, as shown in FIG. 29, when the contents of information which should be transferred are sent from a person #i in charge to a person #j in charge, a message showing that the contents of information which should be transferred are sent is transmitted instead of the contents of information which should be transferred to a pager carried by the person #j in charge as shown by reference number 3 surrounded by a circle and shown in this figure.

In this case, the person #j in charge knows the existence of transference by communication using the pager. This person #j in charge then downloads new patient data to the PDA in the above-mentioned procedure (reference numbers 4 and 5 each of which is surrounded by a circle and which are in FIG. 29) so that the contents of information which should be transferred included in these patient data items are read in the above-mentioned procedure.

Figure 30:
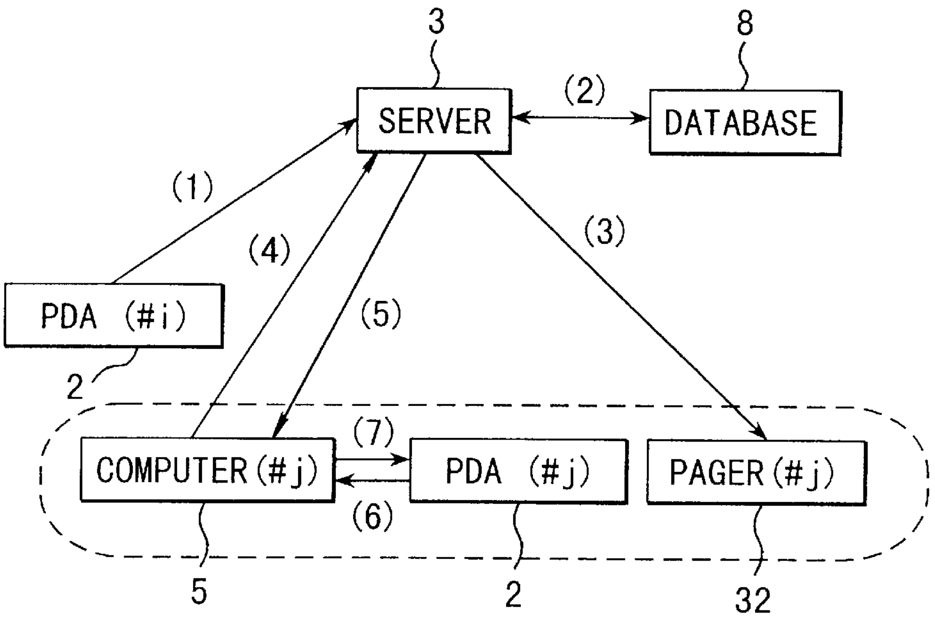
FIG. 30 is a diagram for explaining message communication for the data which should be transferred by the pager.

In this case, the patient data can be downloaded through a computer 5 as shown in FIG. 30 (reference numbers 4 to 7 each of which is surrounded by a circle and which are shown in FIG. 30).

The above transfer means shown in FIG. 27, 29 or 30 may be fixed as one unit on the system, or arbitrary transfer means may be combined and used.

The transfer means can be set and separately used for each person at a destination.

For example, a data base structure as shown in FIG. 32 is prepared as the above-mentioned data base (iv). Here, users h to m correspond to user IDs (or a set of a user ID and a code showing classifications of a visiting nurse, a doctor, etc.).

Here, in an operation for obtaining the concrete destination information from the above ID of the person at a destination, the ID of the person at a destination is set to a key and the data base as shown in FIG. 32 is retrieved so that a device used for the destination and its number are retrieved.

For example, when the destination is j in FIG. 32, it is shown that the receiver is a pager and its number is a number Pj. When the destination is m, it is shown that the receiver is a pager, a facsimile machine and an electronic mail for a wide use and their numbers or addresses are respectively numbers Pm, Fm and address m.

Figure 31:
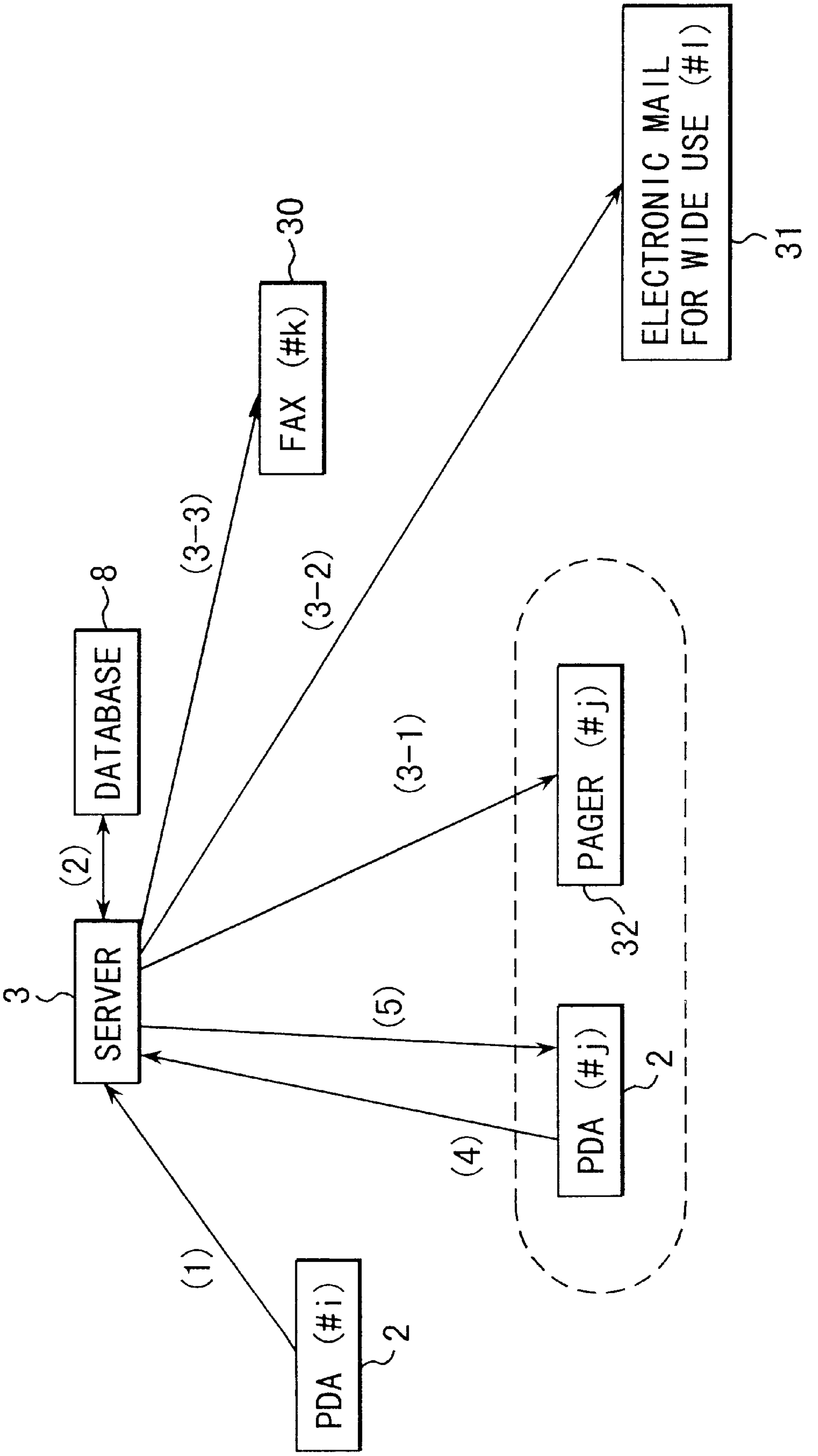
FIG. 31 is a diagram for explaining the distribution of transference using the facsimile machine and the electronic mail for a wide use and the message communication for the data which should be transferred using the pager.

FIG. 31 shows a situation in which the contents of information which should be transferred are transmitted from the person #i in charge to the person #j in charge and doctors #K and #L.

A data file is uploaded from the PDA 2 to the server device 3 (reference number 1 surrounded by a circle and shown in FIG. 31). This data file is written to a data base 8 (reference number 2 surrounded by a circle and shown in FIG. 31). Further, a message showing that there are data which should be transferred is transmitted to the pager of the person #j in charge (reference number 3-1 surrounded by a circle and shown in FIG. 31). Further, information including the contents of information which should be transferred is transmitted to a facsimile machine of the doctor #K (reference number 3-2 surrounded by a circle and shown in FIG. 31). Information including the contents of information which should be transferred is transmitted to the doctor #1 through an electronic mail (reference number 3-2 surrounded by a circle and shown in FIG. 31). Further, the message showing that there are data which should be transferred is transmitted to a pager of the doctor #1 (unillustrated).

Then, the person #j in charge can read the contents of information which should be transferred by downloading patient data to the PDA 2 (reference numbers 4 and 5 each of which is surrounded by a circle and which are shown in FIG. 31). The doctor #K can rapidly read a facsimile document. The doctor #1 can read the contents of information which should be transferred by the electronic mail.

For example, it is possible to separately use devices and numbers used in accordance with a predetermined condition uniformly or for each person at a destination.

For example, in FIG. 33, a time zone and a facsimile machine number used in this time zone are registered as a set to a facsimile column of the data base in FIG. 32 so that the facsimile machine number is separately used in accordance with the time zone.

For example, it is possible to designate a facsimile machine at home in a certain time zone, and designate a facsimile machine in one's place of employment in another certain time zone, and designate both the facsimile machine at home and the facsimile machine in one's place of employment in another certain time zone.

In another setting method, a facsimile machine is designated in a certain time zone and a pager and an electronic mail for a wide use are designated in another certain time zone. Thus, various setting methods are considered.

Predetermined information (e.g., a visiting nursing record document II or values in items linked to the contents of information which should be transferred) may be added to the contents of information which should be transferred, and instructions showing that this information and the contents of information which should be transferred are simultaneously sent may be inputted on the side of the PDA 2. Further, the server device 3 may transmit predetermined information in addition to the contents of information which should be transferred in accordance with such instructions.

(Second Embodiment)

A second embodiment of the present invention will now be described.

As mentioned above, the second embodiment has substantially common structure to that of the first embodiment. Accordingly, here, different portions will mainly be described.

FIG. 34 shows one example of the data structure of a comment file (or a file which should be transferred) in this embodiment.

In the first embodiment, the comment file and the file which should be transferred are separately made. However, in the second embodiment, the comment file and the file which should be transferred are shared. If data is set to a destination ID, these data items are set to be treated as the file which should be transferred. If the destination ID is a predetermined code such as null, 0 or the like, data is set to be treated as the comment file.

Figure 39:
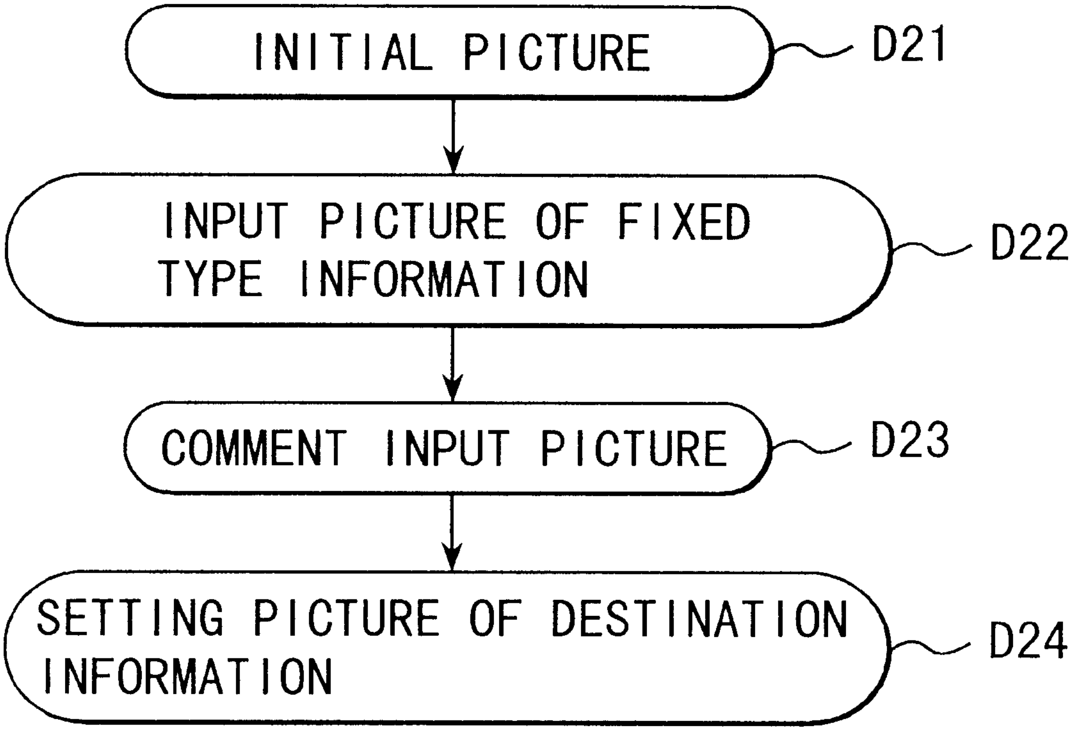
FIG. 39 is a diagram for explaining a basic transitional relation between pictures.

FIG. 39 shows a basic transitional relation between pictures in this embodiment.

In an input picture, the transference button is basically removed from the first embodiment. For example, the pictures shown in FIGS. 13 and 14 are respectively changed to those shown in FIGS. 35 and 36.

Figure 37:
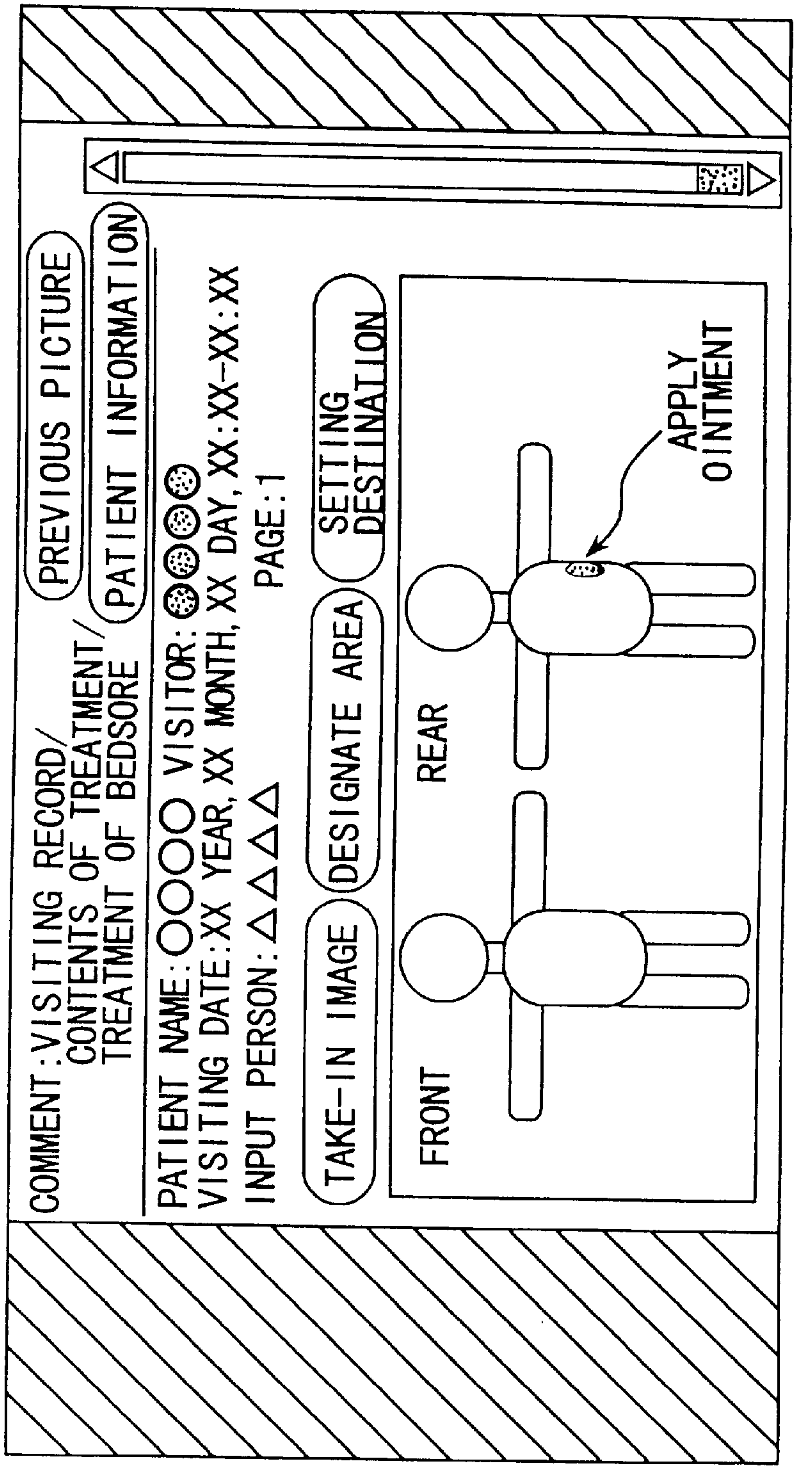
FIG. 37 is a diagram showing a display example of a picture at a comment inputting time.
Figure 38:
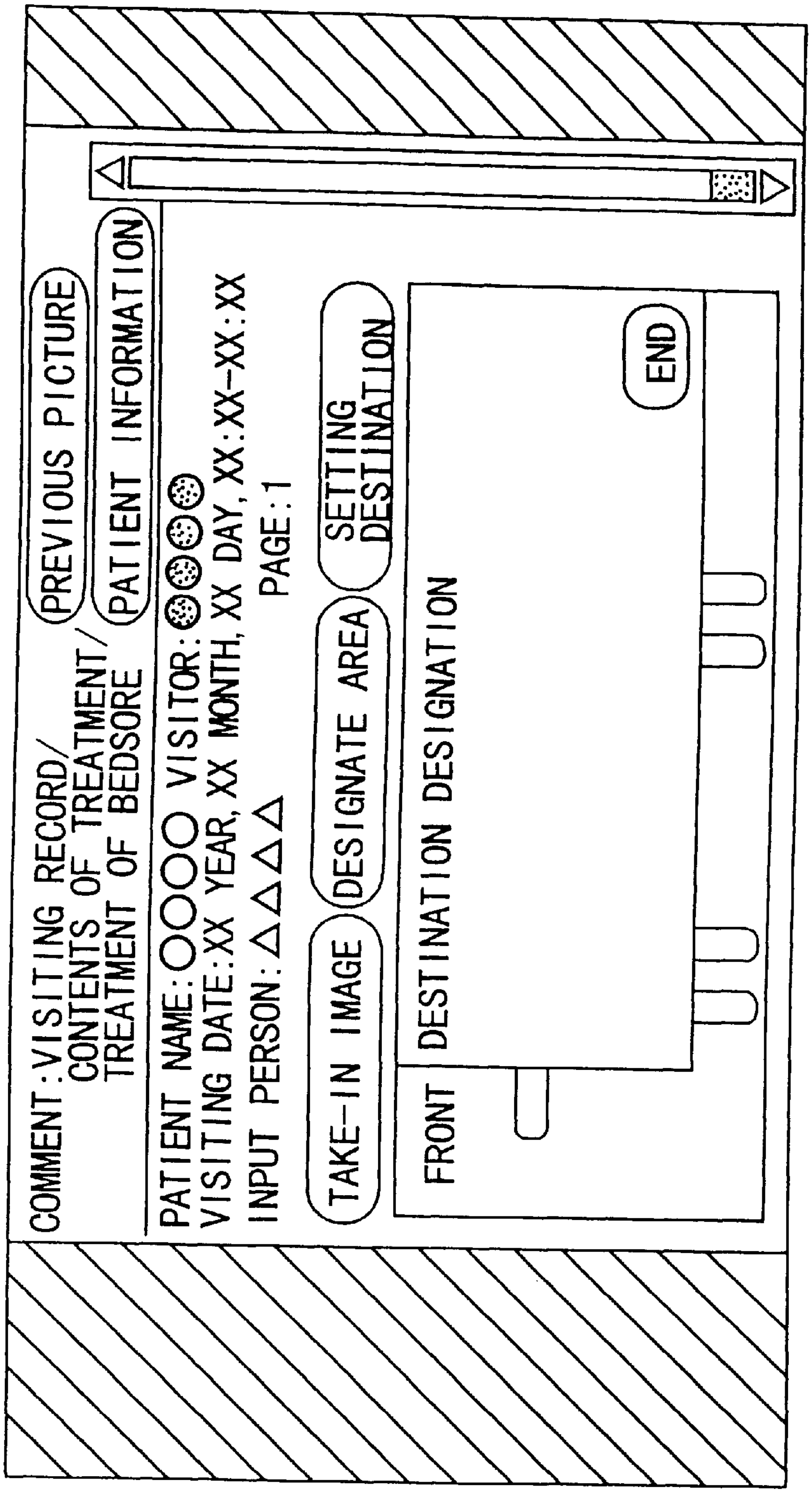
FIG. 38 is a diagram showing a display example of a destination designating picture.

Instead of this, in this embodiment, a destination setting button is provided for a comment input picture as shown in FIG. 37. When this button is clicked, for example, a destination setting picture is opened as shown in FIG. 38. Thus, similar to the first embodiment, a destination is set.

Set destination information is written to the column of a destination ID of the file of FIG. 34. This file is treated as a file which should be transferred.

Figure 40:
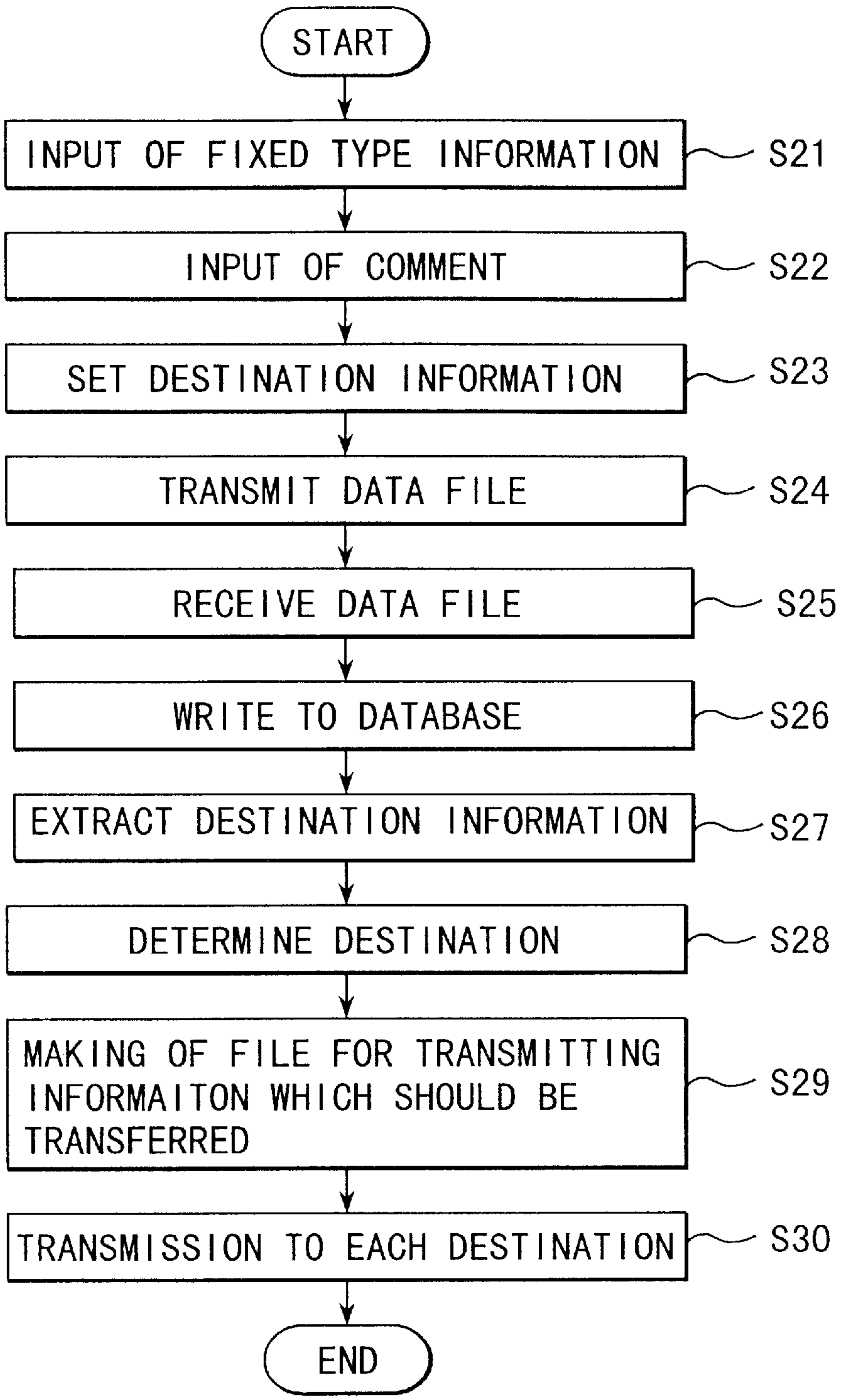
FIG. 40 is a flow chart showing a processing flow from a data file input to transference of information.

FIG. 40 shows a schematic processing flow to be performed from data input in the PDA 2 to the transmission of a file including data which should be transferred or a message showing that the data which should be transferred are sent by the server device 3.

In addition to the above different points, the existence or nonexistence of the file which should be transferred is checked in the step S18 in the first embodiment, but is judged by checking whether destination information is set in the column of a destination ID in a comment file as an object in a step S27 in FIG. 40 in this embodiment.

(Third Embodiment)

A third embodiment of the present invention will now be described.

As mentioned before, the third embodiment has a substantially common structure to that of the first embodiment. Accordingly, here, different portions will be mainly described.

Initially, in FIG. 41, one example of the data structure of a comment file (or a file which should be transferred) according this embodiment is shown.

In the first embodiment, the comment file and the file which should be transferred are separately made. In the second embodiment, the comment file and the file which should be transferred are shared. Further, if data is set to a destination ID, these data items are treated as the file which should be transferred. If the destination ID is a predetermined code such as null, 0, or the like, data is treated as the comment file. However, in the third embodiment, the comment file and the file which should be transferred are shared and a transference setting flag is formed. If this flag is turned on, data is set to be treated as the file which should be transferred. In contrast to this, if this flag is turned off, data is set to be treated as the comment file. For example, when the transference setting flag is 1, data is treated as the file which should be transferred. In contrast to this, if the transference setting flag is a predetermined code such as null, 0, or the like, data is treated as the comment file. The destination information is separately made as a destination information file. When there are no data which should be transferred, the destination information file is not transferred or is transferred with its contents as null.

In the first and second embodiments, the destination is set for each file which should be transferred. However, in the third embodiment, the destination is set with respect to unification of all file which should be transferred.

Figure 43:
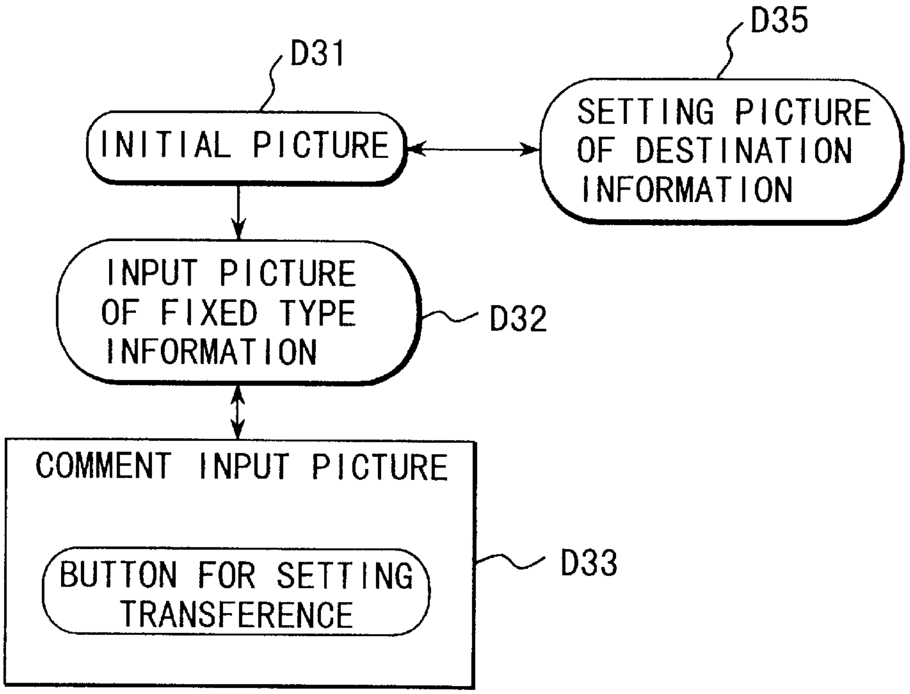
FIG. 43 is a diagram for explaining a basic transitional relation between pictures.

Next, FIG. 43 shows a basic transitional relation between pictures in this embodiment.

Figure 35:
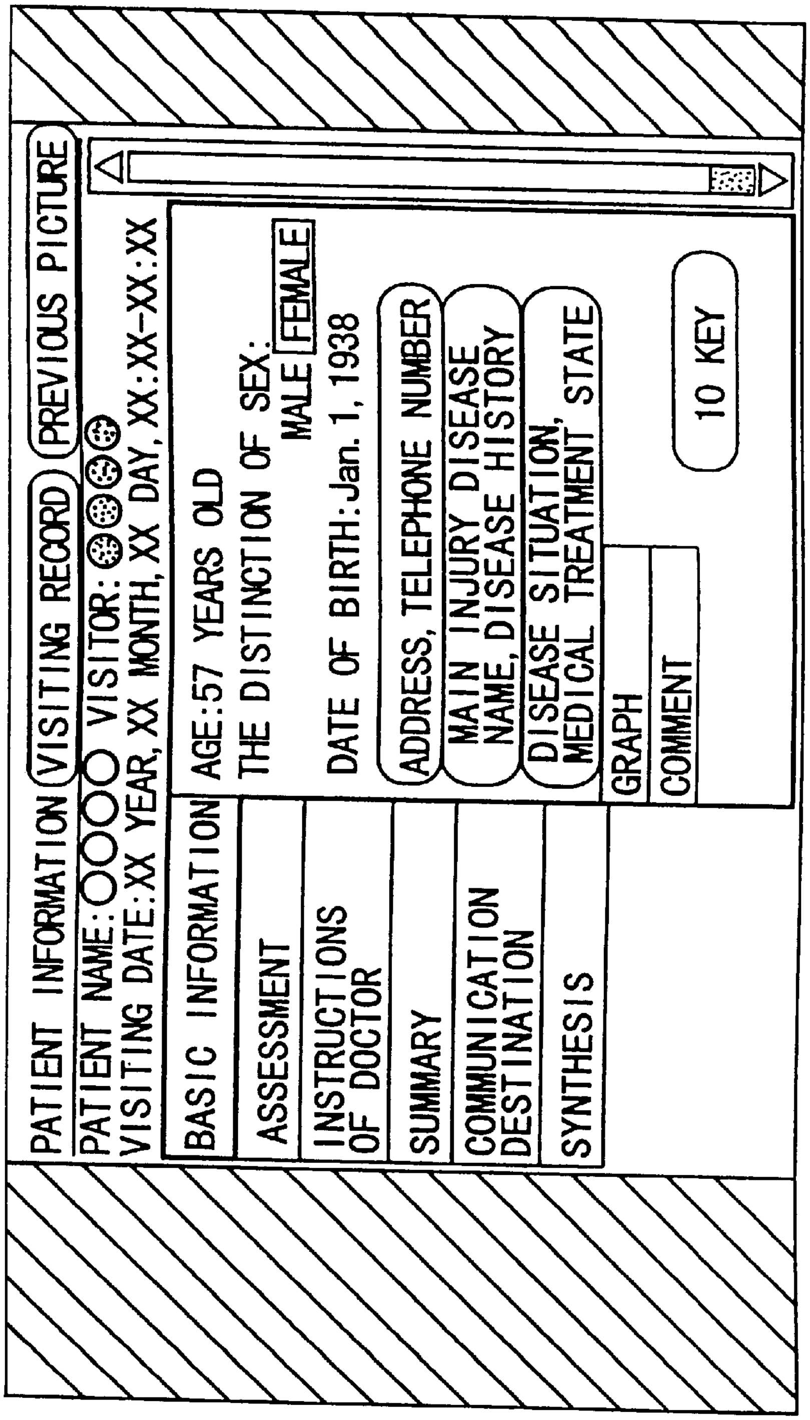
FIG. 35 is a diagram showing a display example of a basic picture of item "patient information."
Figure 36:
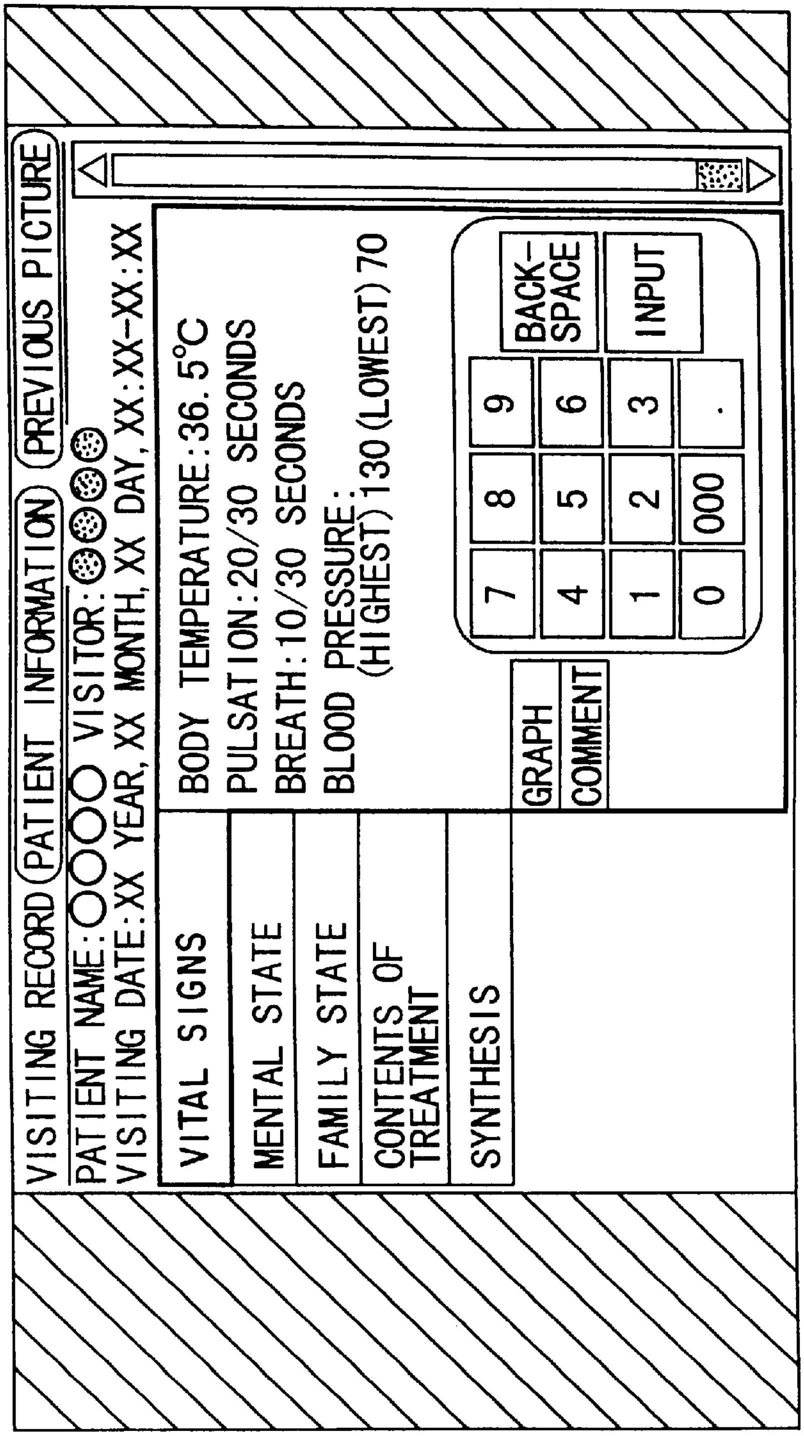
FIG. 36 is a diagram showing a display example of a basic picture of item "visiting record."

In an input picture, the transference button is basically removed from the first embodiment. For example, the pictures of FIGS. 13 and 14 are respectively displayed as shown in FIGS. 35 and 36.

Figure 42:
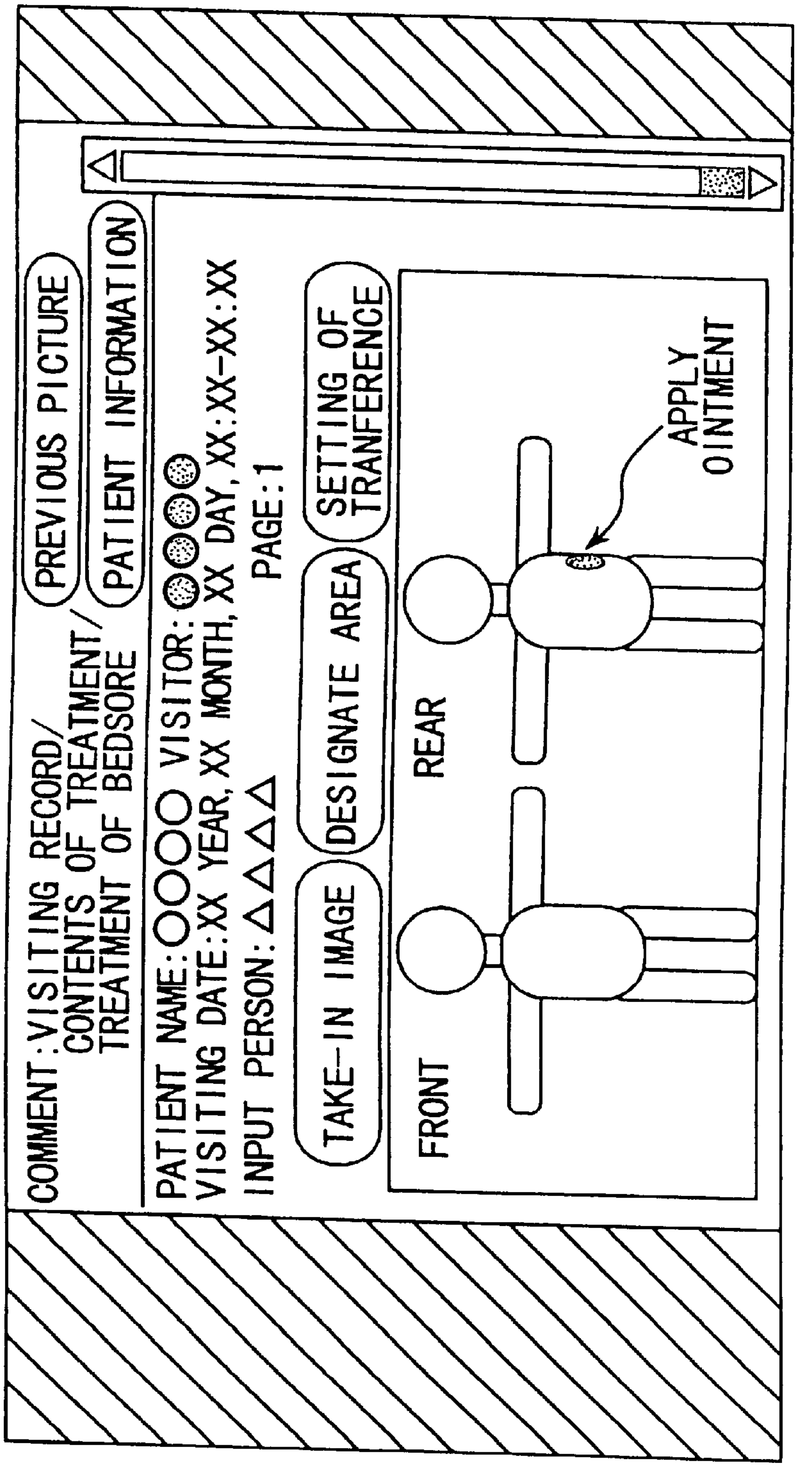
FIG. 42 is a diagram showing a display example of a picture at a comment inputting time.

Instead of this, a transference setting button is formed in a comment input picture as shown in FIG. 42 in this embodiment. When this button is clicked, a transference setting flag is set to 1 or the like so that data is treated as a file which should be transferred.

Figure 26:
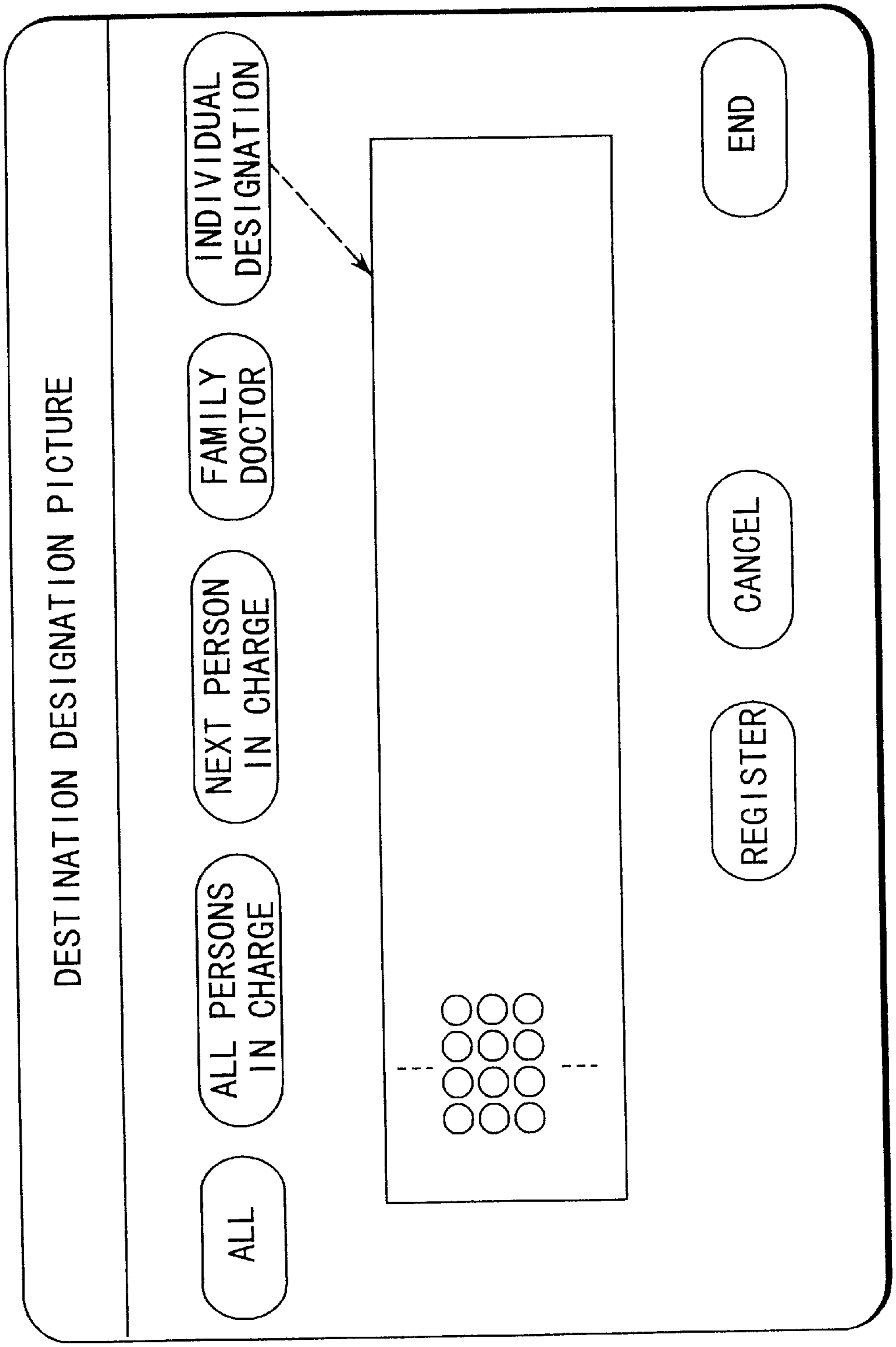
FIG. 26 is a diagram showing another example of the destination designating picture.

In this embodiment, an initial picture is transitionally changed to a destination setting picture as shown in FIG. 24 or 26. Thus, similar to the first embodiment, a destination is set.

The set destination information is uploaded together with other data as a separate file.

Figure 46:
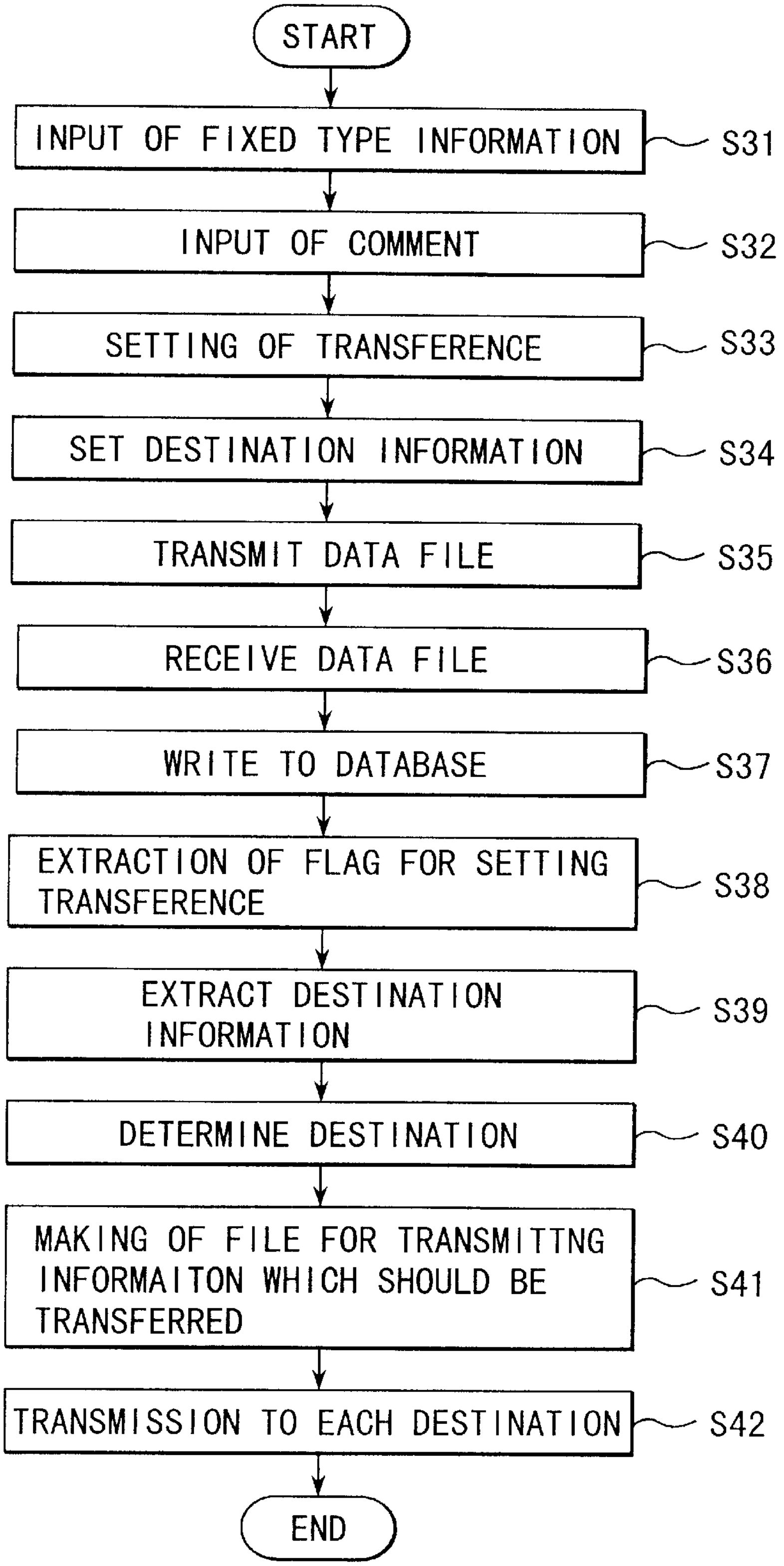
FIG. 46 is a flow chart showing a processing flow from a data file input to transference of information.

FIG. 46 shows a schematic processing flow from a data input in the PDA 2 to the transmission of a file including data which should be transferred or a message showing that the data which should be transferred are sent by the server device 3.

In addition to the above different points, the existence or nonexistence of the file which should be transferred is checked in the step S18 in the first embodiment, but is judged by checking whether a code showing the file which should be transferred is set in the column of a transference setting flag in a comment file as an object in a step S38 in this embodiment. As an alternative to this, the existence or nonexistence of the file which should be transferred can also be judged by checking the existence or nonexistence of a destination information file or whether contents of the destination information file are null.

In this embodiment, the transference setting button may also be formed in the input picture of fixed type information so that data which should be transferred is also be set with respect to the fixed type information. In this case, contents of the fixed type information may be simultaneously transmitted together with the data which should be transferred.

A modified example of the third embodiment will now be described.

In the above description, the destination is set with respect to unification of all file which should be transferred. However, when the transference setting flag is turned on, a classification can be set and the destination can be set with respect to the unification of file which should be transferred having the same classification.

Figure 44:
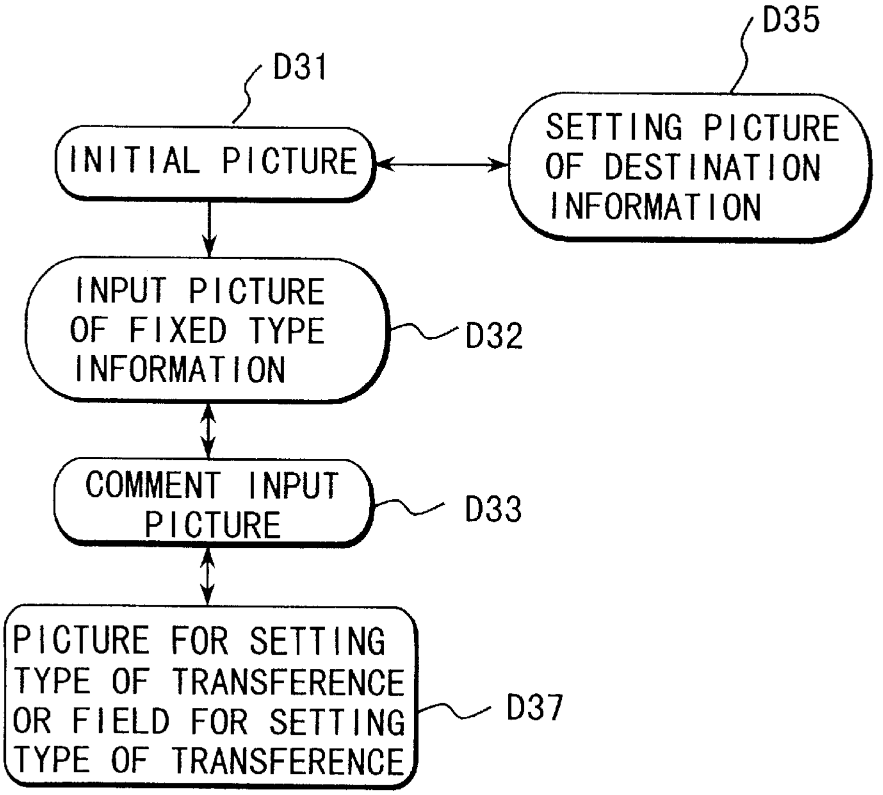
FIG. 44 is a diagram for explaining a basic transitional relation between pictures.

FIG. 44 shows a basic transitional relation between pictures in this case.

Here, when the transference setting button in the comment input picture of FIG. 42 is clicked, a picture for setting a transference classification is opened and the transference classification is set in this picture. As an alternative to this, the transference classification is set in a field for setting the transference classification within the comment input picture of FIG. 42.

A setting method of the transference classification is constructed by a method for selecting a required classification from predetermined classifications, a method for inputting a numeric value showing a classification, etc. In the former method, for example, a button for transference 1 or 2 is displayed. When the button for transference 1 is clicked, 1 is set to the transference setting flag. When the button for transference 2 is clicked, 2 is set to the transference setting flag. In the latter method, 1 as an inputted numeric value is set to the transference setting flag. Accordingly, in the latter method, when a specific numeric value (e.g., 0) is used as a code showing that no transference is set, this specific numeric value cannot be set to be inputted.

Figure 45:
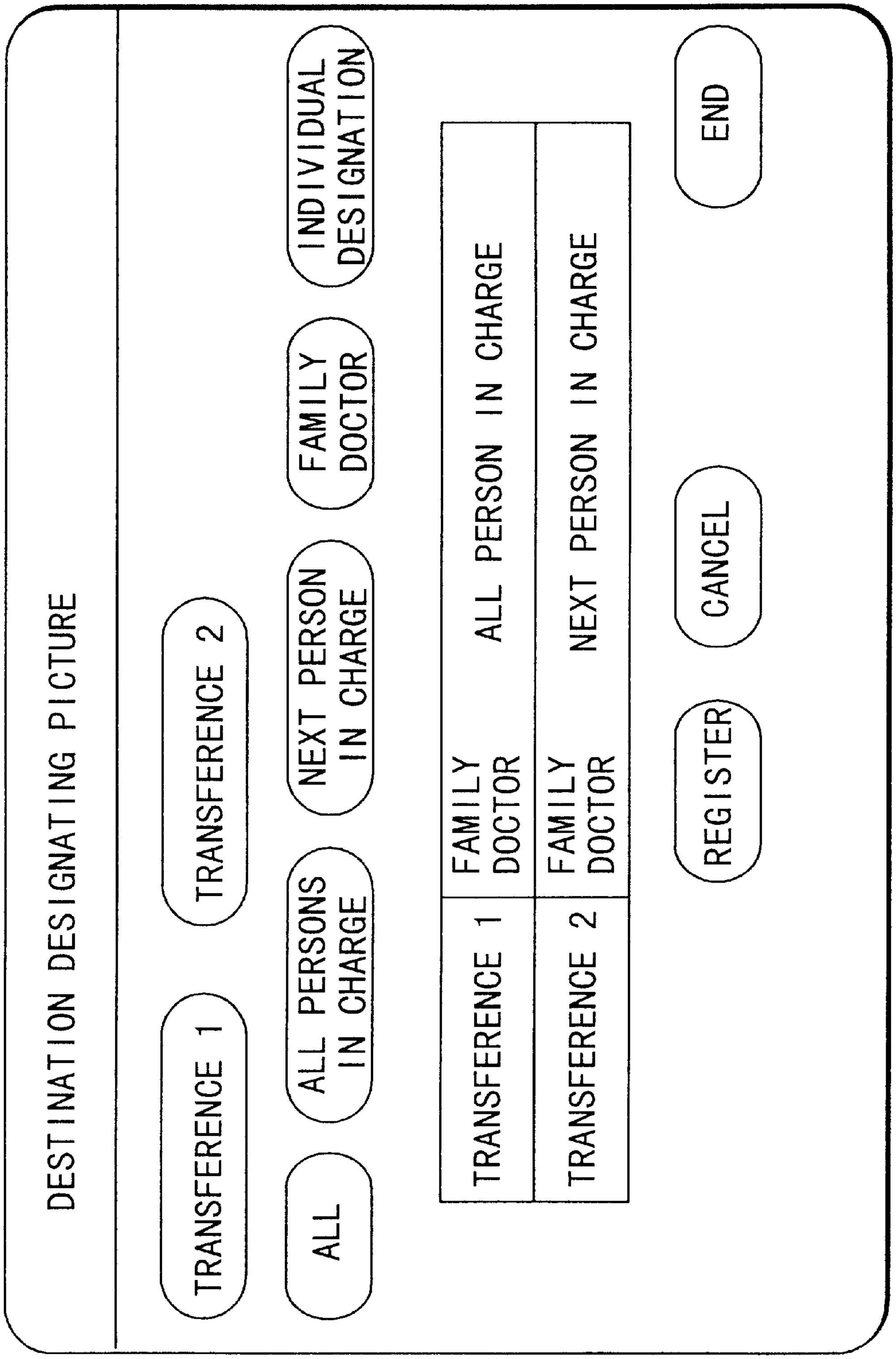
FIG. 45 is a diagram showing one example of a destination designating picture.

As shown in FIG. 45, the destination can be set for each transference classification in a destination setting picture in this case.

Destination information may be set for each master of the PDA in addition to a case in which the destination information is set for each visiting record. In this case, at each data inputting time, names registered at a transference setting time are displayed and can be selected in a sequential order.

In each of the above embodiments, an access right capable of reading a file which should be transferred by only a user set at a destination may be set without making the file which should be transferred. In this case, when patient data is accessed, only the user having the access right can read the file which should be transferred.

The above information sharing system using the PDA can be applied to a system for supporting various operations in a form in which a team of persons in charge is organized and these persons in charge alternately go to a destination, such as maintenance of a plant, a maintenance service operation, a guarding operation, business and the like in addition to a home-based care operation. Similar to the home-based care operation, information to be inputted to the PDA as operations is classified into fixed type information with respect to a fixed type menu selection (the check of items determined in a daily routine operation) or a numeric value input (read and input scales of instruments), and arbitrary information with respect to unfixed type comments and data which should be transferred. The comments and the data which should be transferred, etc. can be naturally inputted by linking fixed type data to unfixed type data while the routine operation is performed. Accordingly, the comments and the data which should be transferred, etc. can be rapidly inputted and referred.

Figure 47:
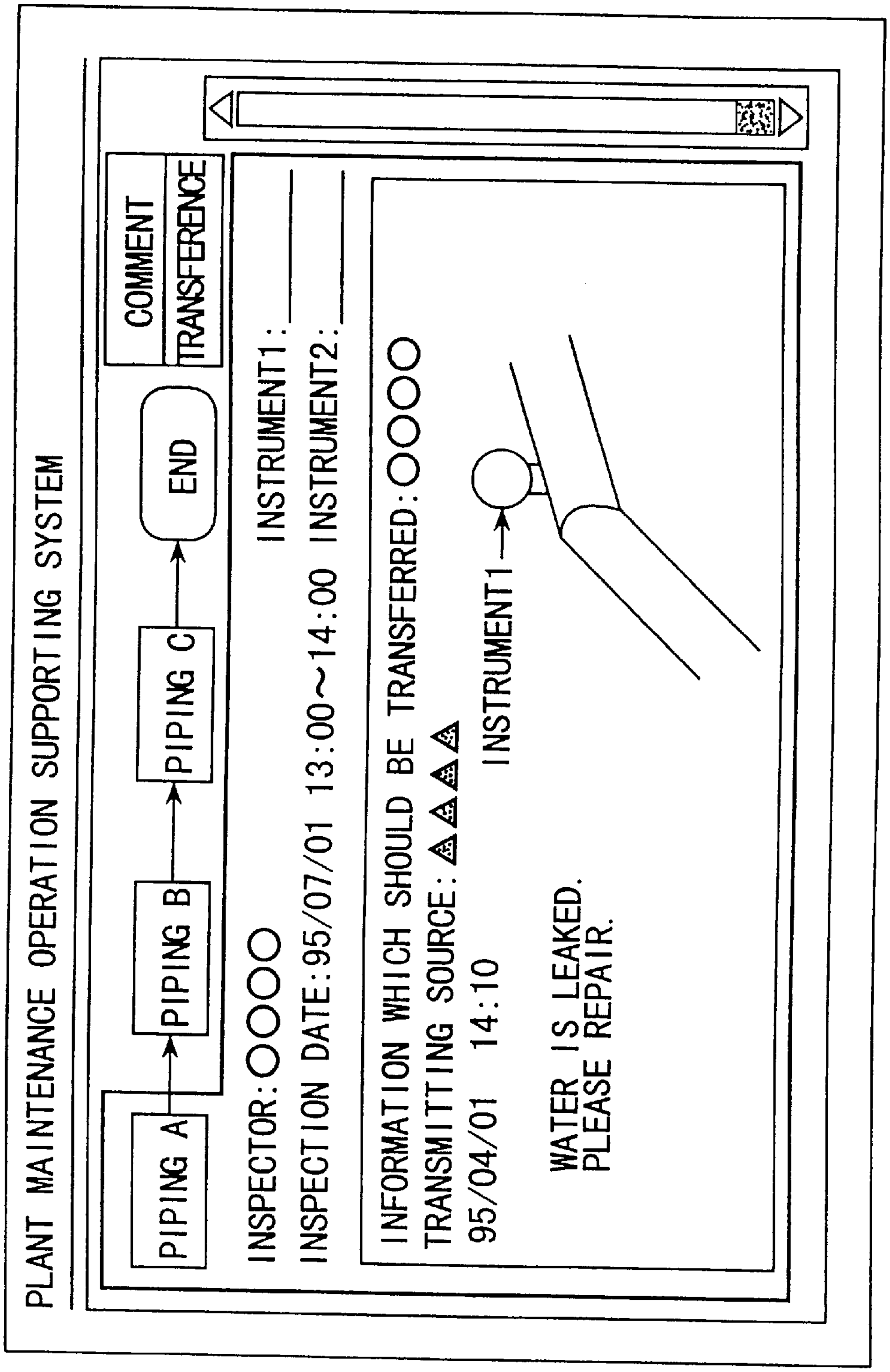
FIG. 47 is a diagram showing a display example of a work flow of a plant maintenance operation supporting system.

For example, in the case of the maintenance operation of a plant, the fixed type information is inputted to the PDA in accordance with each of the checked items (a work flow) determined in advance as shown in FIG. 47. A normal operation is confirmed at each point and numeric values of instruments, etc. are inputted at any time in accordance with a fixed type input picture. For example, there is a case in which water is slightly leaked in "piping A" at a certain time point at which these check items are inputted. In this case, a transference key is selected in a selecting state of item "piping A" and a transference input picture is opened. Further, a water-leaking portion is photographed by a digital still camera and data of this photograph are transferred to the PDA. These data items are inputted to a transference input area and a handwriting memorandum is written onto this data image and a voice comment is further added to this data image. For example, as shown in FIG. 47, "Please repair by the next inspector since water is slightly leaked." is inputted. Then, when the destination is set to "the next inspector" and a reference time limit is set to "before the next visit" and data is stored, the data which should be transferred are automatically linked to the check items (here, "piping A") at an opening time of the transference key. As an alternative to this, as shown in FIG. 48, for example, the structural diagram (map) of a plant is displayed and an inputting operation may be performed in accordance with this structural diagram.

Figure 48:
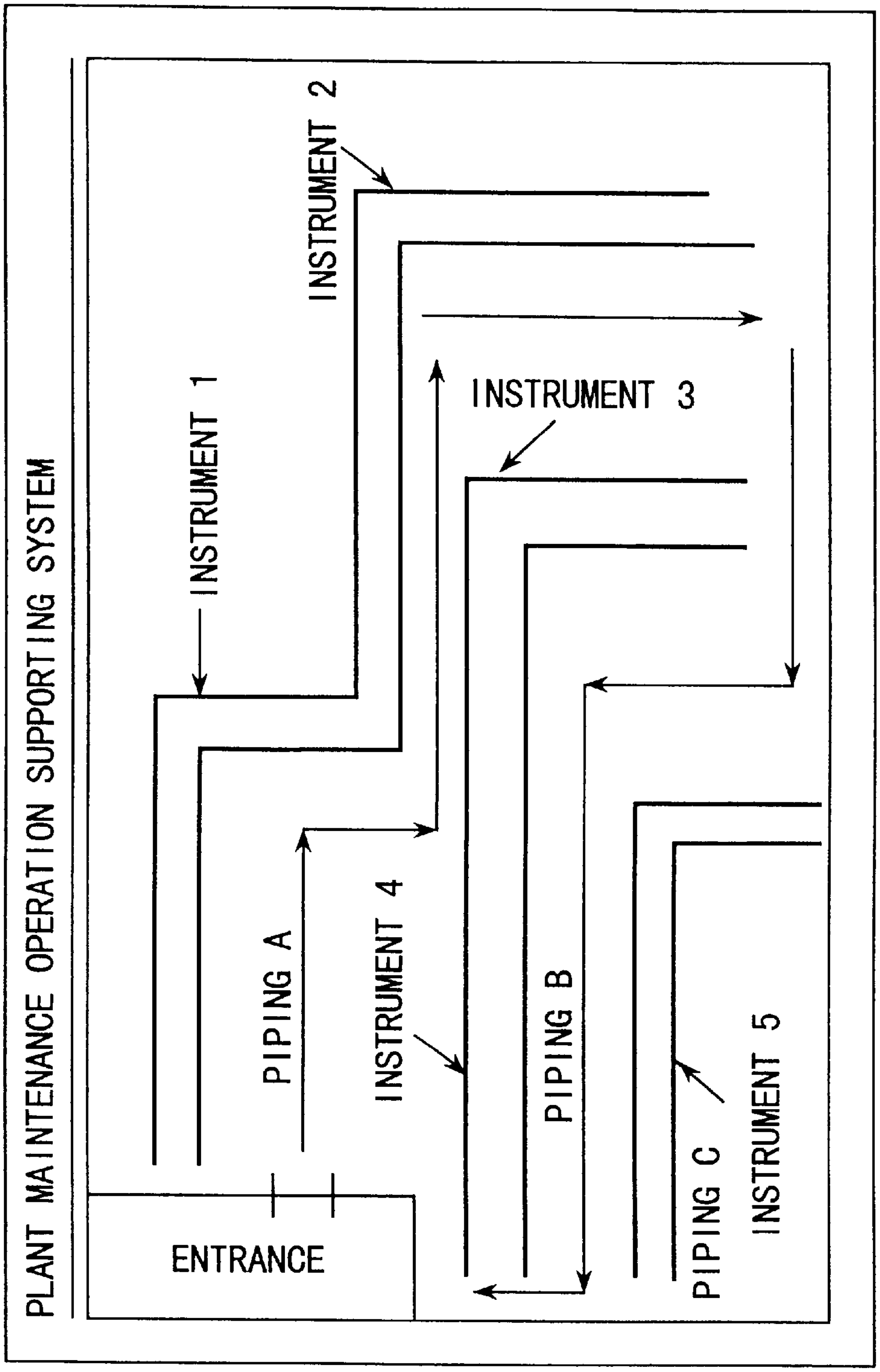
FIG. 48 is a diagram showing a display example of an input/reference picture of a map base in the plant maintenance operation supporting system.

At a referring time, a marker showing the input of comments and data which should be transferred for each place is displayed in the work flow as shown in FIG. 47 or on the map as shown in FIG. 48. For example, in this example, the marker is displayed in an A-piping portion. When this marker is clicked and the transference key is selected, completely similar to the case of the home-based care operation supporting system, past matters transferred with respect to the A-piping can be referred at once by a scroll bar. As an alternative to this, when the next visitor receives data from the server device 3 at the center before his visit and a general transference key is checked, all data items which should be transferred at his own destination are displayed as a list and can be further read at a look. As an alternative to this, the system may be set such that no inputting operation is performed when the above data is received and all files which should be transferred are not opened. With respect to an unread file which should be transferred having a reference time limit, an alarm of the PDA carried by a person in charge designated at a destination before the time limit may be sounded to make this person refer to the unread file which should be transferred. In this example, when no file which should be transferred is read before the visit, "There is a file which should be transferred. Please confirm this file." is displayed by an alarm.

Figure 49:
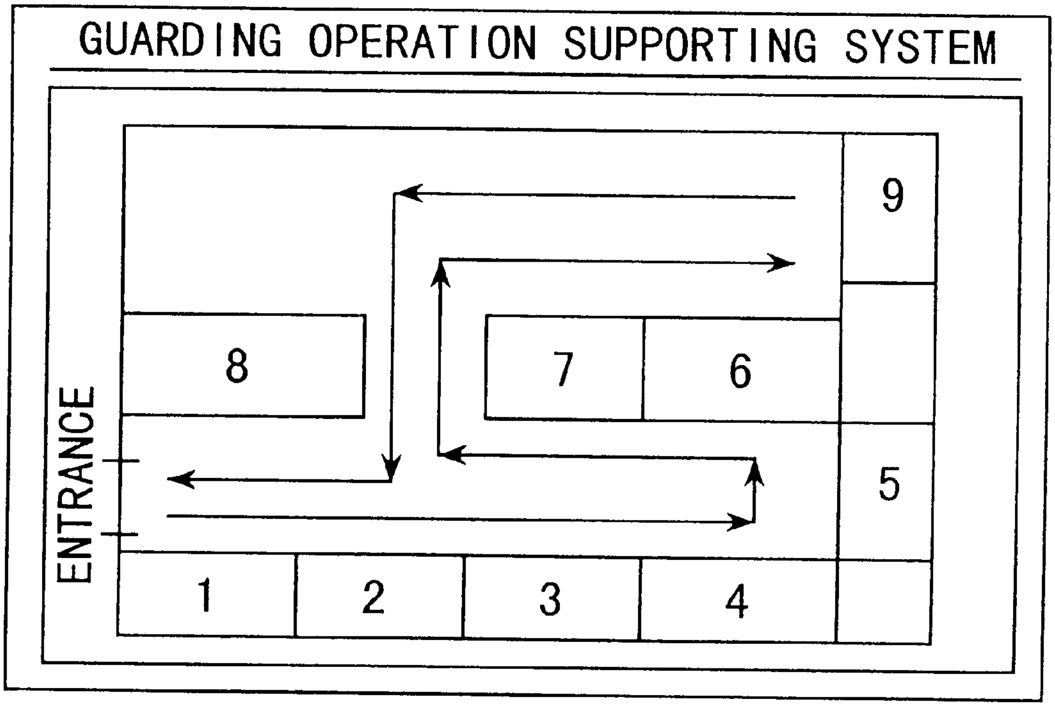
FIG. 49 is a diagram showing a display example of an input/reference picture of a guarding path map base in a guarding operation supporting system.

In the case of the guarding operation, for example, as shown in FIG. 49, the map of a building in charge and an image showing a patrol path are set to a basic picture. Further, checking place and item (this item is displayed when the place is clicked although this item is unillustrated) are presented on the map. Thereafter, similar to the maintenance of a plant, the PDA is carried at a patrol time and only a checking operation is performed if it is normal in each checking place. When a change in state is found, the place is marked (even when no emergency information is required). Thereafter, a comment or transference key is pushed and comments or data which should be transferred are inputted. A place (item) address is added to these data items and data showing confirmation of the check of this place are also inputted as fixed type data. At a referring time of these data items, a marker showing that the comment/data which should be transferred are written onto the map is displayed. When this marker is clicked, related comment/matters which should be transferred are displayed as a list and all the related comment/matters which should be transferred can also be read at a look.

The present invention is not limited to the above embodiments, but can be embodied in various modifications within a technical scope of the invention.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A data transmitting method in a system in which data inputted from an information terminal unit is transmitted through a server having a database, the method comprising the steps of:

inputting data by the information terminal unit, the inputted data constituting a data record;

arbitrarily designating specific data in the data record by a user through the information terminal unit;

appending destination address data to the designated specific data in the data record by a user through the information terminal unit, the destination address data being an address to which the server transfers the designated specific data;

transmitting the data record including the designated specific data with the destination address appended to the server by the information terminal unit;

storing the transmitted data record into the database, by the server;

automatically extracting the specific data with the destination address appended in the data record from the database by the server, using the destination address as a key for retrieval;

transmitting the extracted specific data to the appended destination address by the server.

2. The method according to claim 1, wherein the data transmitted to the server comprises predetermined fixed-form data regarding a predetermined item and arbitrary data permitted to be inputted in relation to the predetermined item, the predetermined fixed form data and the arbitrary data constituting the data record.

3. The method according to claim 1, wherein the server prepares a file of the extracted specific data.

4. A data transmitting system in which data inputted from an information terminal unit is transmitted through a server having a database, the system comprising:

the information terminal unit comprising;

means for inputting data, the inputted data constituting a data record;

means for arbitrarily designating specific data in the data record;

means for appending destination address information to the designated specific data in the data record, the destination address data being an address to which the server transfers the designated specific data; and means for transmitting the data record including the designated specific data with the destination address appended to the server; and the server comprising:

means for storing the transmitted data record in the database;

means for automatically extracting the specific data using the destination address as a key for retrieval; and transmitting means for transmitting the extracted specific data to the appended destination address.

5. The system according to claim 4, wherein the means for transmitting the data record transmits the specific data through communication means which is preliminarily determined according to a person as the destination.

6. The system according to claim 4, further comprising a receiver for receiving the specific data transmitted from the server;

wherein the means for transmitting the data record sets, as the destination, an identifier of the receiver which is preliminarily determined according to a time zone for transmitting the specific data.

7. The system according to claim 4, wherein the data transmitted to the server comprises predetermined fixed form data regarding a predetermined item and arbitrary data permitted to be inputted in relation to the predetermined item, the predetermined fixed form data and the arbitrary data constituting the data record.

8. The system according to claim 4, wherein the server prepares a file of the specific data.

* * * * *